US011135236B2

(12) United States Patent
Burridge

(10) Patent No.: US 11,135,236 B2
(45) Date of Patent: Oct. 5, 2021

(54) RETINOIC ACID RECEPTOR GAMMA AGONISTS TO ATTENUATE ANTHRACYCLINE-INDUCED CARDIOTOXICITY

(71) Applicant: Northwestern University, Evanston, IL (US)

(72) Inventor: Paul W. Burridge, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/376,392

(22) Filed: Apr. 5, 2019

(65) Prior Publication Data

US 2019/0358250 A1 Nov. 28, 2019

Related U.S. Application Data

(60) Provisional application No. 62/655,354, filed on Apr. 10, 2018.

(51) Int. Cl.

| | |
|---|---|
| *A61K 31/704* | (2006.01) |
| *A61K 31/415* | (2006.01) |
| *A61K 31/381* | (2006.01) |
| *A61P 9/00* | (2006.01) |
| *A61K 31/196* | (2006.01) |
| *A61K 31/4436* | (2006.01) |
| *A61P 35/00* | (2006.01) |
| *A61K 31/192* | (2006.01) |

(52) U.S. Cl.
CPC .......... *A61K 31/704* (2013.01); *A61K 31/192* (2013.01); *A61K 31/196* (2013.01); *A61K 31/381* (2013.01); *A61K 31/415* (2013.01); *A61K 31/4436* (2013.01); *A61P 9/00* (2018.01); *A61P 35/00* (2018.01)

(58) Field of Classification Search
CPC .. A61K 31/704; A61K 31/192; A61K 31/196; A61K 31/381; A61K 31/415; A61K 31/4436; A61P 9/00; A61P 35/00
See application file for complete search history.

(56) References Cited

U.S. PATENT DOCUMENTS

| | | |
|---|---|---|
| 2007/0117761 A1 | 5/2007 | Biadatti |
| 2009/0023811 A1 | 1/2009 | Biadatti |
| 2009/0036536 A1 | 2/2009 | Biadatti |
| 2010/0130613 A1 | 5/2010 | Dreno |
| 2010/0130614 A1 | 5/2010 | Dreno |
| 2010/0261754 A1 | 10/2010 | Biadatti-Portal |
| 2010/0273883 A1 | 10/2010 | Biadatti |
| 2012/0016031 A1 | 1/2012 | Biadatti |
| 2012/0214869 A1 | 8/2012 | Biadatti |
| 2017/0072010 A1* | 3/2017 | Gudas .................. A61K 31/203 |

OTHER PUBLICATIONS

Buzdar et al., Cancer, 1985, 55, p. 2761-2765. (Year: 1985).*
Definition of prevent, Oxford English Dictionary Online, http://dictionary.oed.com/, accessed online Mar. 27, 2010, especially definition 9a. at p. 2. (Year: 2010).*
Czeczuga-Semeniuk et al., Folia Histochem. Cytobiol., 2004, 42(4), p. 221-227. (Year: 2004).*
Supplementary Information for Aminkeng et al., Nature Genetics, 2015, 47(9), p. 1079-1084, 9 pgs. (Year: 2015).*
Craig et al., Br. J. Clin. Pharmacol., 2017, 83, p. 1141-1142. (Year: 2017).*
Aggarwal, S., et al. (2006). Nonclassical action of retinoic acid on the activation of the cAMP response element-binding protein in normal human bronchial epithelial cells. Mol Biol Cell 17, 566-575.
Aminkeng, F., et al. (2015). A coding variant in RARG confers susceptibility to anthracycline-induced cardiotoxicity in childhood cancer. Nat Genet 47, 1079-1084.
Aminkeng, F., et al. Recommendations for genetic testing to reduce the incidence of anthracycline-induced cardiotoxicity. Br. J. Clin. Pharmacol. 82, 683-695 (2016).
Berlin, V. et al (1981). Reduction of adriamycin to a semiquinone-free radical by NADPH cytochrome P-450 reductase produces DNA cleavage in a reaction mediated by molecular oxygen. J Biol Chem 256, 4747-4756.
Blanco, J.G., et al. Anthracycline-related cardiomyopathy after childhood cancer: role of polymorphisms in carbonyl reductase genes—a report from the Children's Oncology Group. J. Clin. Oncol. 30, 1415-1421 (2012).
Boyle, E.A., et al (2017). An Expanded View of Complex Traits: From Polygenic to Omnigenic. Cell 169, 1177-1186.
Burridge, P.W., et al Chemically Defined Culture and Cardiomyocyte Differentiation of Human Pluripotent Stem Cells. Curr Protoc Hum Genet 87, 21 23 21-15 (2015).
Burridge, P.W., et al. Chemically defined generation of human cardiomyocytes. Nat. Methods 11, 855-860 (2014).
Burridge, P.W., et al. Human induced pluripotent stem cell-derived cardiomyocytes recapitulate the predilection of breast cancer patients to doxorubicin-induced cardiotoxicity. Nat. Med. 22, 547-556 (2016).
Cahan, P. et al. Origins and implications of pluripotent stem cell variability and heterogeneity. Nat. Rev. Mol. Cell Biol. 14, 357-368 (2013).
Canon, E., et al. (2004). Rapid effects of retinoic acid on CREB and ERK phosphorylation in neuronal cells. Mol Biol Cell 15, 5583-5592.
Chen, G., et al. Chemically defined conditions for human iPSC derivation and culture. Nat Methods 8, 424-429 (2011).
Cheng, H., et al. (2011). A novel preclinical strategy for identifying cardiotoxic kinase inhibitors and mechanisms of cardiotoxicity. Circ Res 109, 1401-1409.

(Continued)

*Primary Examiner* — Jonathan S Lau
(74) *Attorney, Agent, or Firm* — Quarles & Brady LLP

(57) ABSTRACT

Disclosed are methods, pharmaceutical compositions, kits, and systems for treating or preventing cardiotoxicity in a subject undergoing treatment with an anthracycline chemotherapeutic agent. The methods, pharmaceutical compositions, kits, and systems typically include or utilize an agonist of the retinoic acid receptor gamma (RARG).

20 Claims, 56 Drawing Sheets

Specification includes a Sequence Listing.

(56) References Cited

OTHER PUBLICATIONS

Chou, B.K., et al. A facile method to establish human induced pluripotent stem cells from adult blood cells under feeder-free and xeno-free culture conditions: a clinically compliant approach. Stem Cells Transl Med 4, 320-332 (2015).

Chu, V.T., et al. Increasing the efficiency of homology-directed repair for CRISPR-Cas9- induced precise gene editing in mammalian cells. Nat. Biotechnol. 33, 543-548 (2015).

Delacroix, L., et al. (2010). Cell-specific interaction of retinoic acid receptors with target genes in mouse embryonic fibroblasts and embryonic stem cells. Mol Cell Biol 30, 231-244.

Doench, J.G., et al. Optimized sgRNA design to maximize activity and minimize offtarget effects of CRISPR-Cas9. Nat. Biotechnol. 34, 184-191 (2016).

Fajardo, G., et al. beta2-adrenergic receptors mediate cardioprotection through crosstalk with mitochondrial cell death pathways. J Mol Cell Cardiol 51, 781-789 (2011).

Fryer, R.M., et al. (2001). Differential activation of extracellular signal regulated kinase isoforms in preconditioning and opioid-induced cardioprotection. J Pharmacol Exp Ther 296, 642-649.

Fusaki, N., et al. Efficient induction of transgene-free human pluripotent stem cells using a vector based on Sendai virus, an RNA virus that does not integrate into the host genome. Proc. Jpn. Acad. Ser. B Phys. Biol. Sci. 85, 348-362 (2009).

Granger, C.B. (2006). Prediction and prevention of chemotherapy-induced cardiomyopathy: can it be done? Circulation 114, 2432-2433.

Hasan, S., et al. (2004). Doxorubicin cardiotoxicity in African Americans. J Natl Med Assoc 96, 196-199.

Hudson, M.M., et al. Clinical ascertainment of health outcomes among adults treated for childhood cancer. JAMA 309, 2371-2381 (2013).

Ichikawa, Y., et al. Cardiotoxicity of doxorubicin is mediated through mitochondrial iron accumulation. J. Clin. Invest. 124, 617-630 (2014).

Ichiki, T. (2006). Role of cAMP response element binding protein in cardiovascular remodeling: good, bad, or both? Arterioscler Thromb Vasc Biol 26, 449-455.

Iulianella, A. et al. (2002). Chimeric analysis of retinoic acid receptor function during cardiac looping. Dev Biol 247, 62-75.

Izumi, M., et al. (2006). Cross-talk between bone morphogenetic protein 2 and leukemia inhibitory factor through ERK 1/2 and Smad1 in protection against doxorubicin-induced injury of cardiomyocytes. J Mol Cell Cardiol 40, 224-233.

Khiati, S., et al. Mitochondrial topoisomerase I (top1mt) is a novel limiting factor of doxorubicin cardiotoxicity. Clin. Cancer Res. 20, 4873-4881 (2014).

Krischer, J.P., et al. Clinical cardiotoxicity following anthracycline treatment for childhood cancer: the Pediatric Oncology Group experience. J. Clin. Oncol. 15, 1544-1552 (1997).

Lalevee, S., et al. Genome-wide in silico identification of new conserved and functional retinoic acid receptor response elements (direct repeats separated by 5 bp). J. Biol. Chem. 286, 33322-33334 (2011).

Lefrak, E.A., et al. (1973). A clinicopathologic analysis of adriamycin cardiotoxicity. Cancer 32, 302-314.

Lek, M., et al. Analysis of protein-coding genetic variation in 60,706 humans. Nature 536, 285-291 (2016).

Liao, Y., et al. The Subread aligner: fast, accurate and scalable read mapping by seed-and-vote. Nucleic Acids Res. 41, e108(2013).

Lim, C.C., et al. Anthracyclines induce calpain-dependent titin proteolysis and necrosis in cardiomyocytes. J. Biol. Chem. 279, 8290-8299 (2004).

Love, M.I., et al. Moderated estimation of fold change and dispersion for RNA-seq data with DESeq2. Genome Biol. 15, 550 (2014).

Lyu, Y.L., et al. Topoisomerase IIbeta mediated DNA double-strand breaks: implications in doxorubicin cardiotoxicity and prevention by dexrazoxane. Cancer Res. 67, 8839-8846 (2007).

Magdy, T., et al. (2016). Validating the pharmacogenomics of chemotherapy-induced cardiotoxicity: What is missing? Pharmacol Ther 168, 113-125.

Minotti, G., et al. (2004). Anthracyclines: molecular advances and pharmacologic developments in antitumor activity and cardiotoxicity. Pharmacol Rev 56, 185-229.

Mulrooney, D.A., et al. Cardiac outcomes in a cohort of adult survivors of childhood and adolescent cancer: retrospective analysis of the Childhood Cancer Survivor Study cohort. BMJ 339, b4606 (2009).

Musunuru, K., et al. (2018). Functional Assays to Screen and Dissect Genomic Hits: Doubling Down on the National Investment in Genomic Research. Circ Genom Precis Med 11, e002178.

Oceguera-Yanez, F., et al. Engineering the AAVS1 locus for consistent and scalable transgene expression in human iPSCs and their differentiated derivatives. Methods 101, 43-55 (2016).

Ochoa, W.F., et al. (2002). Additional binding sites for anionic phospholipids and calcium ions in the crystal structures of complexes of the C2 domain of protein kinase calpha. J Mol Biol 320, 277-291.

Oeffinger, K.C., et al. Chronic health conditions in adult survivors of childhood cancer. N. Engl. J. Med. 355, 1572-1582 (2006).

Peterson, S.E., et al. (2014). Genomic instability in pluripotent stem cells: implications for clinical applications. J Biol Chem 289, 4578-4584.

Ran, F.A., et al. Genome engineering using the CRISPR-Cas9 system. Nat. Protoc. 8, 2281-2308 (2013).

Schmittgen, T.D. et al. (2008). Analyzing real-time PCR data by the comparative C(T) method. Nat Protoc 3, 1101-1108.

Schneider, B. P., et al. Genome Wide Association Study for Anthraycyline-Induced Congestive Heart Failure. Clin Cancer Res. Jan. 1, 2017; 23(1): 43-51.

Simoncikova, P., et al. (2008). The effect of chronic doxorubicin treatment on mitogen-activated protein kinases and heat stress proteins in rat hearts. Physiol Res 57 Suppl 2, S97-S102.

Singal, P.K., et al. (1998). Doxorubicin-induced cardiomyopathy. N Engl J Med 339, 900-905.

Su, H.F., et al. (2006). Oleylethanolamide activates Ras-Erk pathway and improves myocardial function in doxorubicin-induced heart failure. Endocrinology 147, 827-834.

Swain, S.M., et al. (2003). Congestive heart failure in patients treated with doxorubicin: a retrospective analysis of three trials. Cancer 97, 2869-2879.

Van Dalen, E.C., et al. (2014). Treatment including anthracyclines versus treatment not including anthracyclines for childhood cancer. Cochrane Database Syst Rev, CD006647.

Van Der Pal, H.J., et al. High risk of symptomatic cardiac events in childhood cancer survivors. J. Clin. Oncol. 30, 1429-1437 (2012).

Volonte, D., et al. (2008). Caveolin-1 and caveolin-3 form heterooligomeric complexes in atrial cardiac myocytes that are required for doxorubicin-induced apoptosis. Am J Physiol Heart Circ Physiol 294, H392-401.

Von Hoff, D.D., et al. Risk factors for doxorubicin-induced congestive heart failure. Ann. Intern. Med. 91, 710-717 (1979).

Wojnowski, L., et al. NAD(P)H oxidase and multidrug resistance protein genetic polymorphisms are associated with doxorubicin-induced cardiotoxicity. Circulation 112, 3754-3762 (2005).

Xiang, P., et al. (2009). Dexrazoxane protects against doxorubicin-induced cardiomyopathy: upregulation of Akt and Erk phosphorylation in a rat model. Cancer Chemother Pharmacol 63, 343-349.

Yang, F., et al. Doxorubicin, DNA torsion, and chromatin dynamics. Biochim. Biophys. Acta 1845, 84-89 (2014).

Yang, L., et al. (2016). All-trans retinoic acid protects against doxorubicin-induced cardiotoxicity by activating the ERK2 signalling pathway. Br J Pharmacol 173, 357-371.

Zhang, S., et al. Identification of the molecular basis of doxorubicin-induced cardiotoxicity. Nat. Med. 18, 1639-1642 (2012).

* cited by examiner

C

| Targeted modification | CRISPR/Cas9 gene editing strategy | Isogenic |
|---|---|---|
| Indels by gRNA1 | gRNA1+gRNA2 | 1/11 (9.1%) |
| Indels by gRNA2 | gRNA1+gRNA2 | 7/11 (63.6%) |
| Indels by both | gRNA1+gRNA2 | 1/11 (9.1%) |
| *RARG* insertion | gRNA-T2+*RARG* cDNA | 2/3 (66.7%) |

| Targeted modification | CRISPR/Cas9 gene editing strategy | Isogenic |
|---|---|---|
| Indels | gRNA3 | 7/20 (35%) |

Figure 8 (continued)

RETINOIC ACID RECEPTOR GAMMA AGONISTS TO ATTENUATE ANTHRACYCLINE-INDUCED CARDIOTOXICITY

CROSS-REFERENCE TO RELATED PATENT APPLICATIONS

This application claims the benefit of priority under 35 U.S.C. § 119(e) to U.S. Provisional Application No. 62/655,354, filed on Apr. 10, 2018, the contents of which are incorporated herein by reference in their entireties.

STATEMENT REGARDING FEDERALLY SPONSORED RESEARCH OR DEVELOPMENT

This invention was made with government support under HL121177 awarded by the National Institutes of Health. The government has certain rights in the invention.

BACKGROUND

The field of the invention relates to cardiotoxicity and the use of retinoic acid receptor gamma (RARG) agonists for treating and/or preventing cardiotoxicity induced by chemotherapeutic agents administered in cancer therapy. In particular, the field of the invention relates to the use of RARG agonists for treating and/or preventing anthracycline-induced cardiotoxicity, specifically doxorubicin-induced cardiotoxicity (DIC).

Anthracycline chemotherapy agents are widely used for treating a wide range of malignancies. Commonly administered anthracycline agents include doxorubicin and daunorubicin among others. Unfortunately, anthracycline agents have a well-established dose-dependent cardiotoxicity that can lead to heart failure. At present, it is not possible to predict which patients will be affected by anthracycline-induced cardiotoxicity, including doxorubicin-induced cardiotoxicity (DIC). Only one drug to protect against doxorubicin-induced cardiotoxicity is currently approved by the Federal Drug Administration (Dexrazoxane™), which has a number of undesirable side-effects itself and concerns over efficacy.

We have used a human induced pluripotent stem cells-cardiomyocyte model (hiPSC-CM model) to discover that RAR subtype specific orally-available small molecule agonists of RARG are suitable cardioprotectants. The identified RARG agonists are capable of attenuating sensitivity to doxorubicin both in vitro and in vivo. As such, treatment with RARG agonists has the potential to protect cancer patients, including childhood cancer patients from DIC.

SUMMARY

Disclosed are methods, pharmaceutical compositions, kits, and systems for treating or preventing cardiotoxicity in a subject undergoing treatment with an anthracycline chemotherapeutic agent. The methods, pharmaceutical compositions, kits, and systems typically include or utilize an agonist of the retinoic acid receptor gamma (RARG).

DETAILED DESCRIPTION

Figure 1:
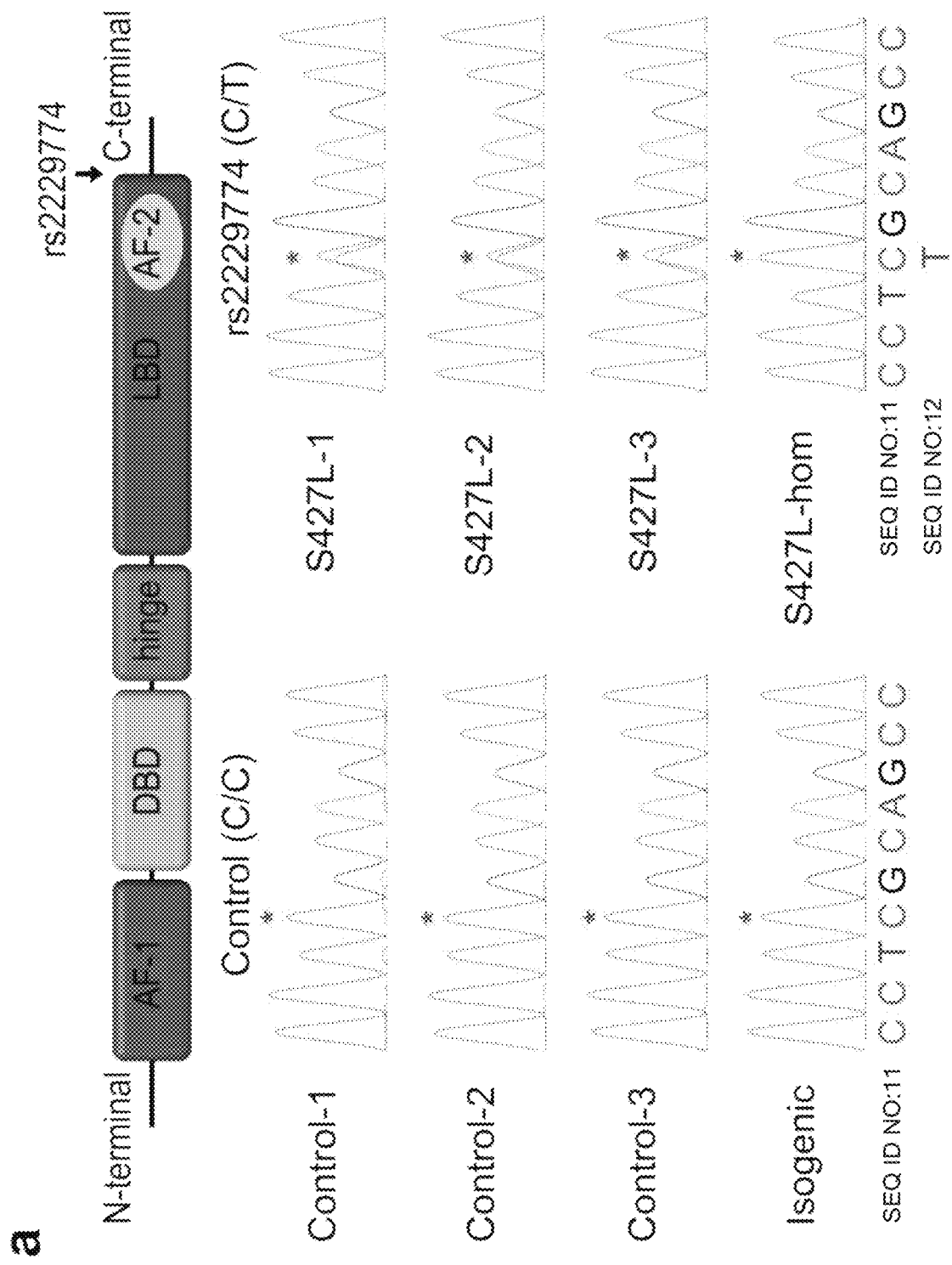
FIG. 1. Patient-specific hiPSC-CMs with the RARG variant recapitulate increased risk of doxorubicin-induced cardiotoxicity. Comparison of hiPSC-CMs from control patients and patients harboring the heterozygous (S427L) rs2229774 variant in RARG, after 24 h or 72 h of doxorubicin treatment. Derived from three Control and three S427L patient hiPSC lines. (a) Upper: RARG is composed of a ligand independent activation function (AF-1) domain, a DNA binding domain, and a ligand binding domain that a ligand-dependent AF-2 domain to recruit coactivators. Arrow indicates relative location of the RARG SNP. Lower: Sanger sequencing of the Control (C/C, major allele) and S427L (C/T, minor allele) hiPSC lines. Asterisk indicates SNP locus. (b) Representative images for sarcomeric organization in hiPSC-CMs after 24 h of doxorubicin treatment at the indicated concentrations, as assessed by immunofluorescence staining for α-actinin (ACTN2) and cardiac troponin T (TNNT2). (c) Effect of doxorubicin (72 h) on hiPSC-CM viability. (d) Effect of doxorubicin (24 h) on caspase 3 and 7 activity in hiPSC-CMs. (e) Representative images for immunofluorescent staining of γH2AX in hiPSC-CMs after 24 h of doxorubicin treatment at the indicated concentrations. (f) Quantification of γH2AX staining in hiPSC-CMs by flow cytometry. Throughout, data are represented as mean±s.e.m. unpaired two-tailed Student's t-test of mean log $LD_{50}$ extracted from best fit variables (c and d) or unpaired two-tailed Student's t-test (f). Scale bars, 25 μm.
Figure 1:
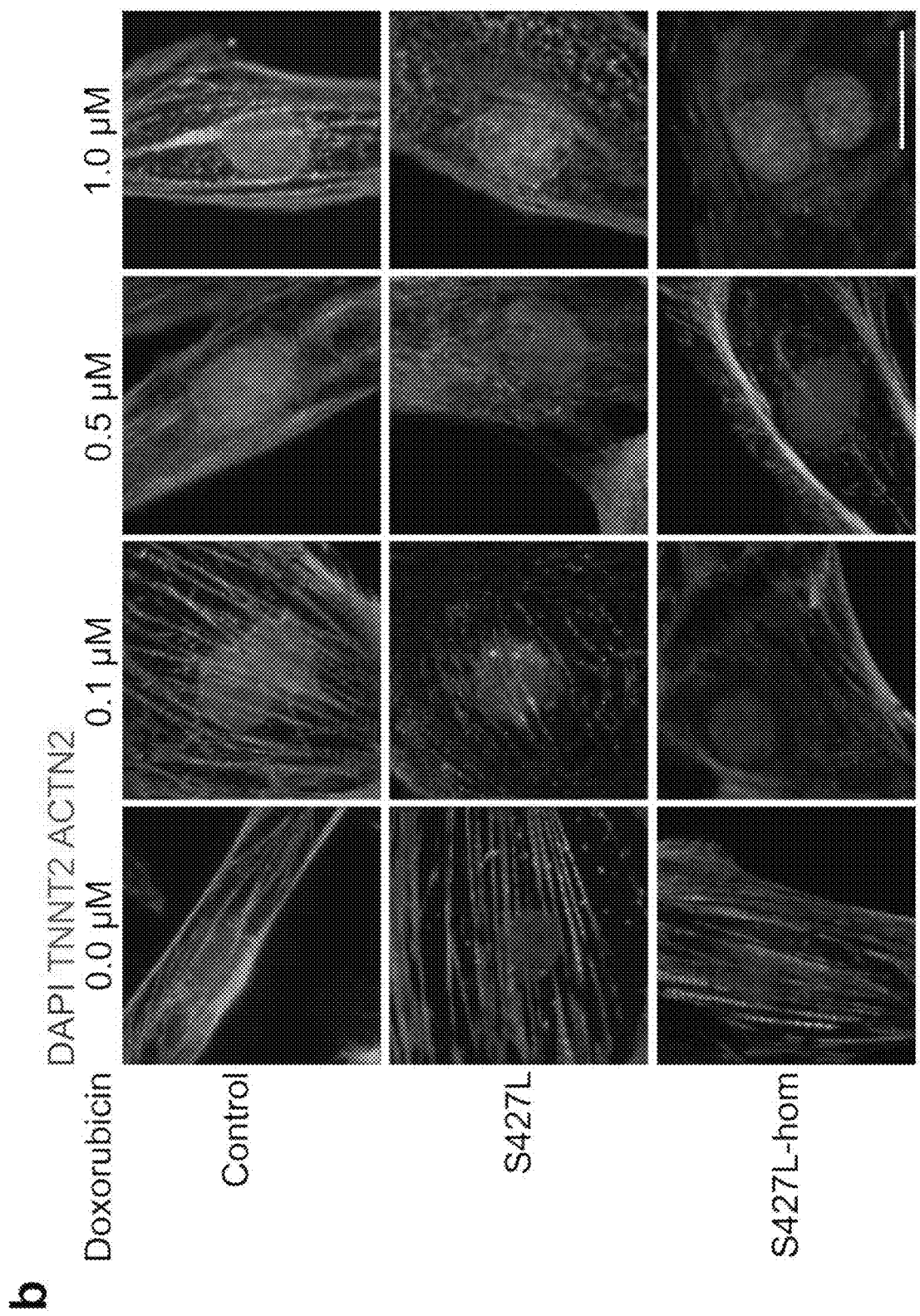
Figure 1:
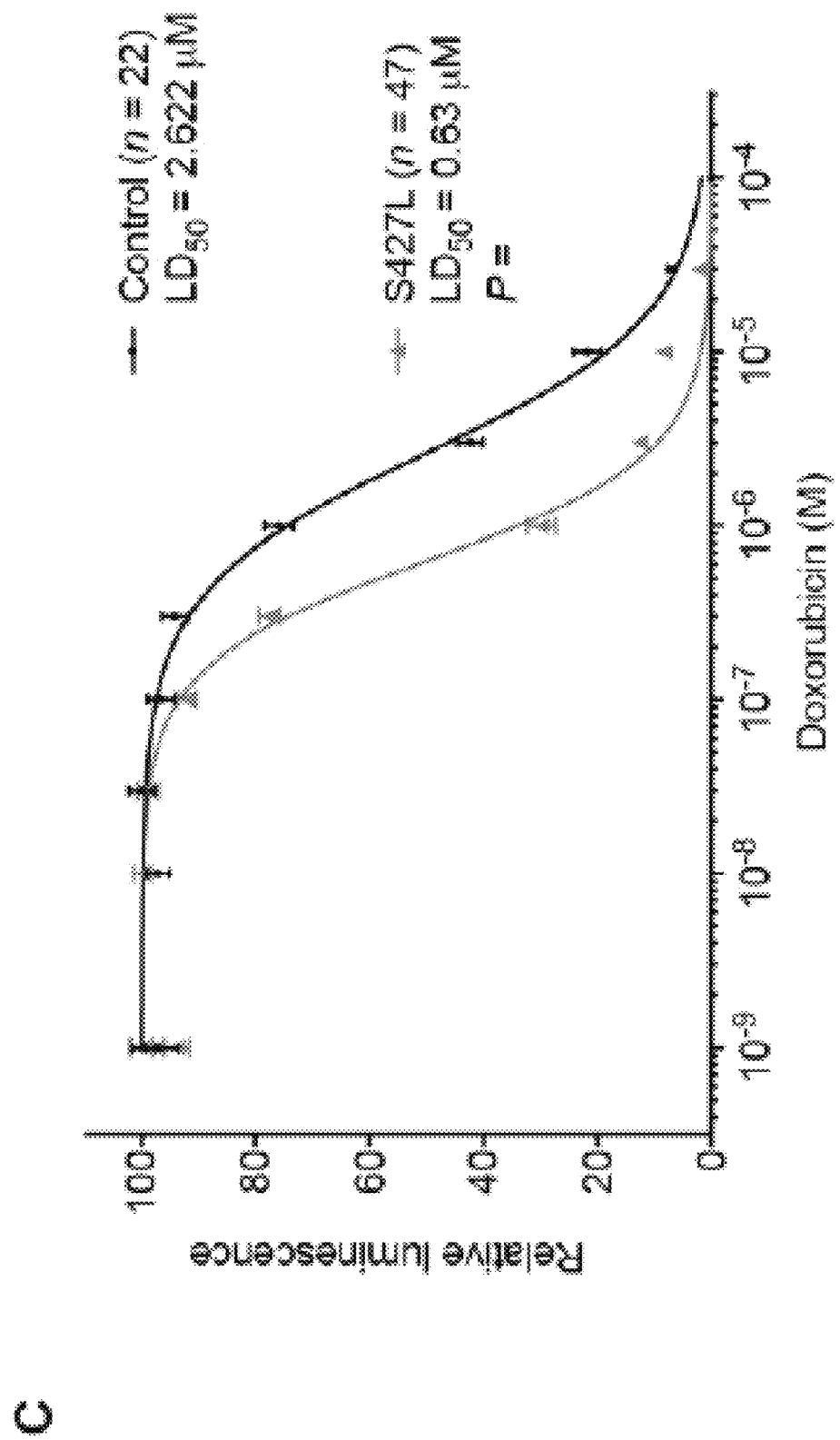
Figure 1:
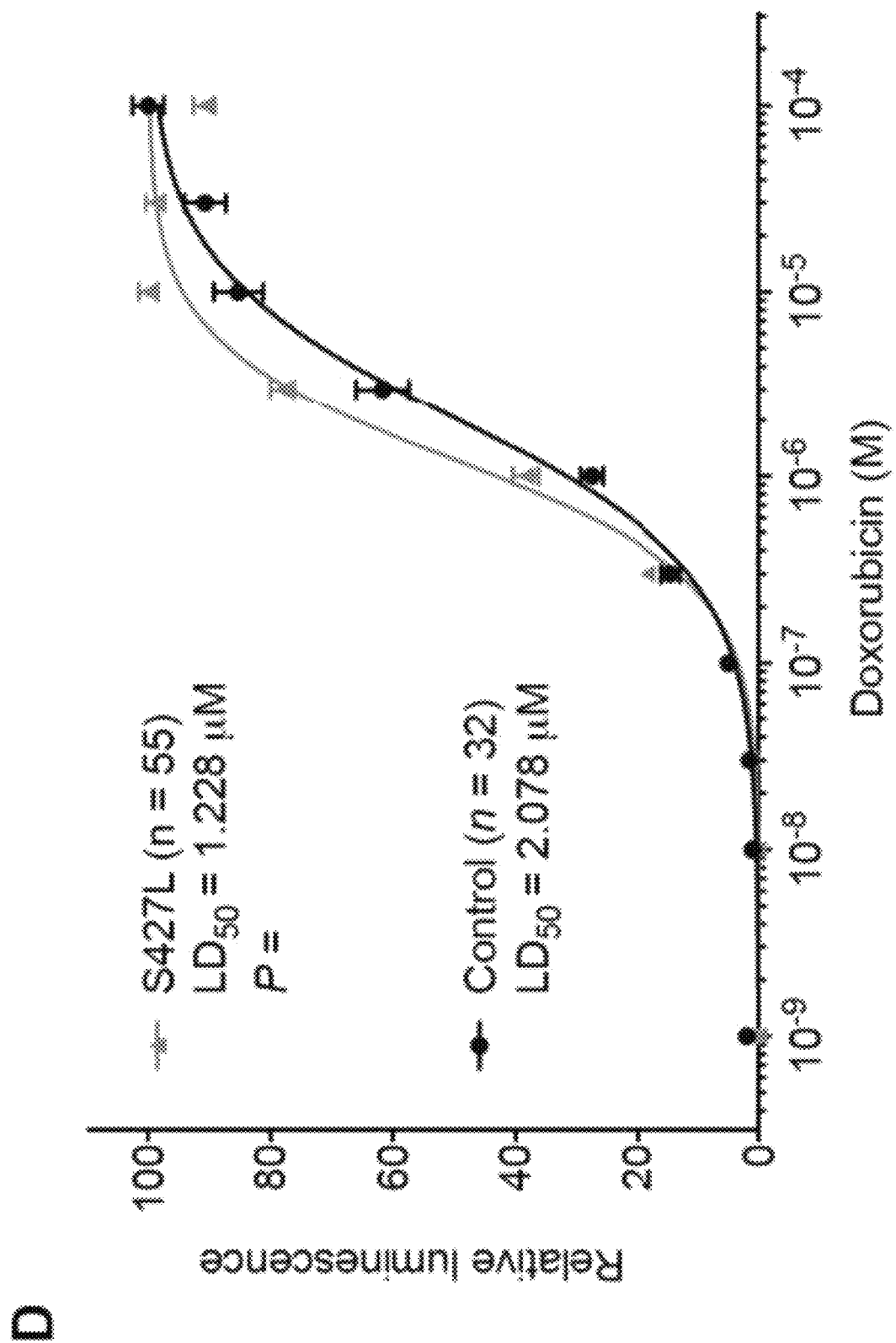
Figure 1:
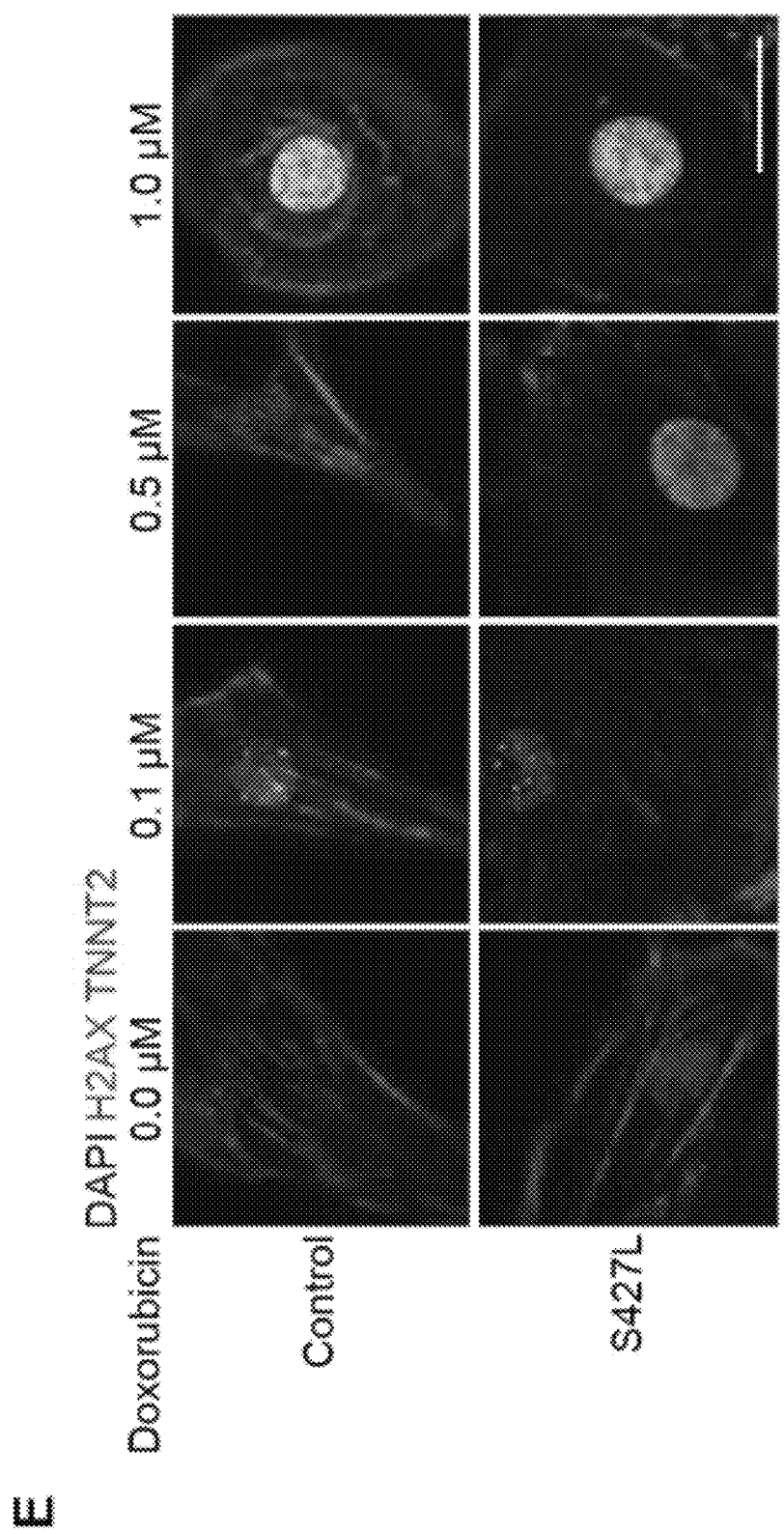
Figure 1:
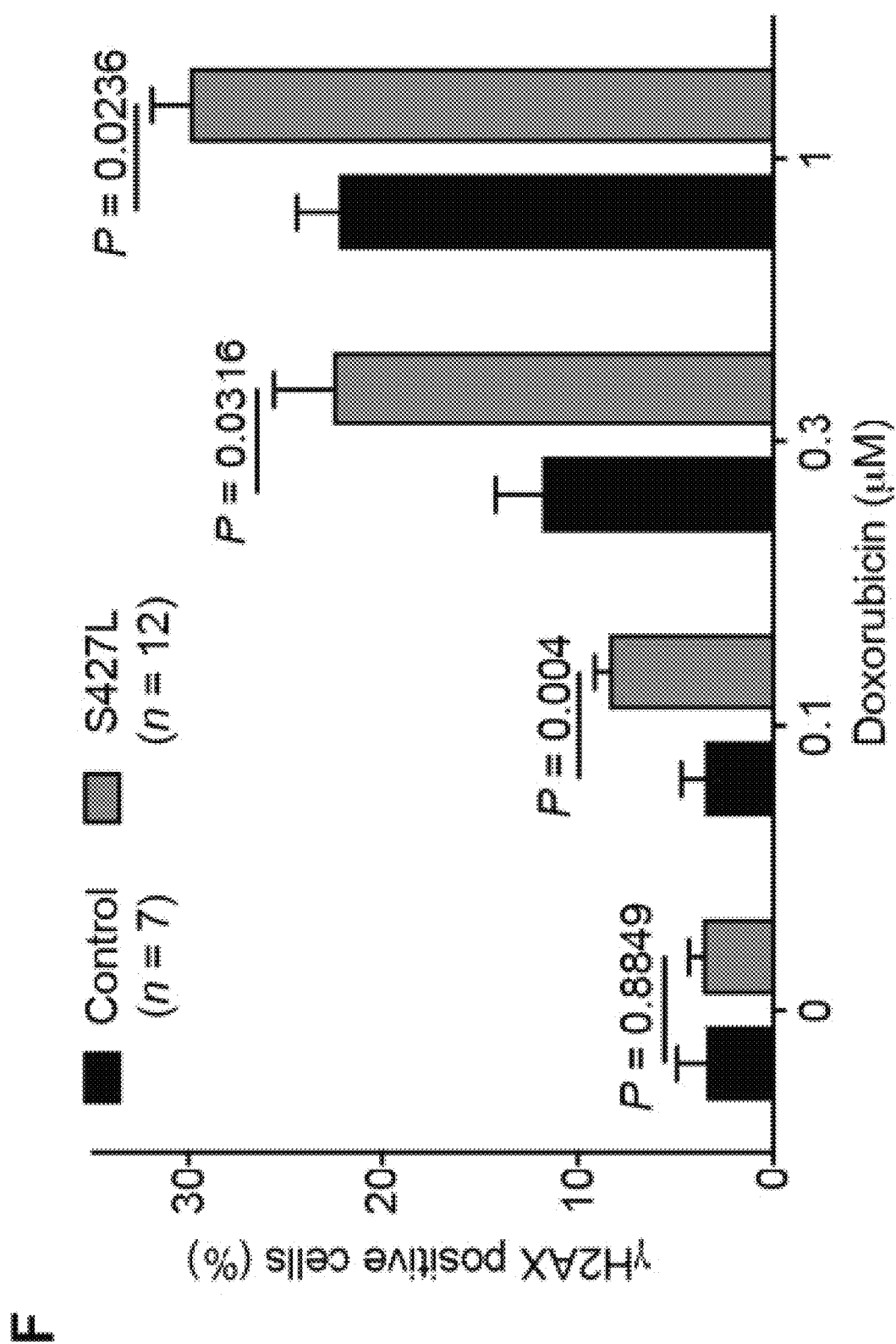

The present invention is described herein using several definitions, as set forth below and throughout the application.

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

Unless otherwise specified or indicated by context, the terms "a", "an", and "the" should be interpreted to mean "one or more." For example, "an RARG agonist" or "an anthracycline" should be interpreted to mean "one or more RARG agonist's" and "one or more anthracycline's," respectively As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" should be interpreted to mean plus or minus 510% of the particular term and "substantially" and "significantly" should be interpreted to mean plus or minus >10% of the particular term.

As used herein, the terms "include" and "including" should be interpreted to have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, a "subject" may be interchangeable with "patient" or "individual" and means an animal, which may be a human or non-human animal, in need of treatment. A subject may include a subject of any age. In some embodiments, the subject in need thereof is not an adult (e.g., where the subject is a child).

A "subject in need of treatment" may include a subject having a disease, disorder, or condition that can be treated by administering to the subject one or more therapeutic agents as disclosed herein. A subject in need thereof may include a subject having or at risk for developing a cell proliferative disease or disorder such as cancer where the subject has been selected for treatment with an anthracycline chemotherapeutic agent. A subject in need thereof may include, but is not limited to, a subject having or at risk for developing any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus) where the subject has been selected for treatment with an anthracycline chemotherapeutic agent. As such, methods of treating cancers are contemplated herein, including methods of treating cancers selected from, but not limited to any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus), where the subject is administered an anthracycline chemotherapeutic agent and a retinoic acid receptor gamma (RARG) agonist.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, the term "pharmaceutical composition" may include be defined as a composition that includes a therapeutically effective amount of a therapeutic agent(s) and a pharmaceutically acceptable carrier for delivering the therapeutic agent(s) to target cells or target tissue. As used herein, the term "pharmaceutically acceptable carrier" refers to a carrier for administration of a therapeutic agent which facilitates the delivery of the therapeutic agent to target cells or target tissue. Pharmaceutically acceptable carriers may include solid carriers and liquid carriers, optionally where the therapeutic agents are dissolved in the liquid carriers. As used herein, the term "therapeutically effective amount" refers to that amount of a therapeutic agent that provides a therapeutic benefit in the treatment, prevention, or management of a disease, disorder, or side-effects of treating a diseases or disorder (e.g., side-effect of treating cell proliferation diseases or disorders with anthracycline chemotherapeutic agents).

As used herein, the term "kit" or "system" refers to a combination of components, which may be utilized to achieve a specific purpose. For example, disclosed herein are kits and therapeutic systems that include an agent for treating cancer (e.g., an anthracycline chemotherapeutic agent) and a retinoic acid receptor gamma (RARG) agonist. In the disclosed kits or systems, the components may be packaged together or separately.

Retinoic Acid Receptor Gamma (RARG) Agonists to Attenuate Anthracycline-Induced Cardiotoxicity Disclosed are methods, pharmaceutical compositions, kits, and systems for treating or preventing cardiotoxicity in a subject undergoing treatment with an anthracycline chemotherapeutic agent. The methods, pharmaceutical compositions, kits, and systems typically include or utilize an agonist of the retinoic acid receptor gamma (RARG).

In the disclosed methods, the subject has a cell proliferative disease or disorder such as cancer and is undergoing or has been selected to undergo treatment with an anthracycline chemotherapeutic agent. In some embodiments of the disclosed methods, the subject has a cell proliferative disease or disorder selected from the group consisting of bladder cancer, breast cancer, glioblastoma, lymphoma, leukemia, lung cancer, ovarian cancer, pancreatic cancer, soft tissue sarcoma, and thyroid cancer.

In the disclosed methods, the subject has a cell proliferative disease or disorder such as cancer and further has a genotype that renders the subject as highly sensitive to side-effects of treatment by an anthracycline chemotherapeutic agent, such as cardiotoxicity. In some embodiments, the subject has the T-allele (i.e., the minor allele) of the single nucleotide polymorphism (SNP) rs2229774 (p.Ser427Leu). The subject may be heterozygous for the T-allele or homozygous for the T-allele.

In the disclosed methods, the subject is undergoing or has been selected to undergo treatment with an anthracycline chemotherapeutic agent. The anthracycline chemotherapeutic agent typically is an anthracycline that intercalates within DNA and prevents the release of topoisomerase 2 β (TOP2B) from DNA bound to the TOP2B. In the disclosed methods, the subject may be under going treatment with an anthracycline or has been selected to undergo treatment with an anthracycline selected from the group consisting of doxorubicin, daunorubicin, epirubicin, idarubicin, and aldoxorubicin.

In the disclosed methods, the subject that is undergoing or has been selected to undergo treatment with an anthracycline chemotherapeutic agent is administered an RARG agonist. In some embodiments, the RARG agonist treats or prevents undesirable side-effects that may be induced by the anthracycline chemotherapeutic agent, for example side-effects that may be induced by the anthracycline chemotherapeutic agent when the anthracycline chemotherapeutic agent is administered at an elevated dosage. In some embodiments, the maximum cumulative dose of the anthracycline chemotherapeutic agent that may be administered when an RARG agonist is not administered is increased when the RARG agonist is administered.

In the disclosed methods, the subject may be undergoing or may be selected to undergo treatment with doxorubicin. In clinical practice, because of side-effects such as cardiotoxicity, the maximum cumulative dose of doxorubicin that is administered is ~400-450 mg/m$^2$. In some embodiments of the presently disclosed methods, a subject may be administered a maximum cumulative dose of doxorubicin that is greater than about 400 mg/m$^2$, 450 mg/m$^2$, 500 mg/m$^2$, 550 mg/m$^2$, or 600 mg/m$^2$, when the subject is administered a RARG agonist, either before, concurrently with, and/or after doxorubicin is administered to the subject.

In the disclosed methods, the subject may be undergoing or may be selected to undergo treatment with daunorubicin. In clinical practice, because of side-effects such as cardiotoxicity, the maximum cumulative dose of daunorubicin that is administered is ~600 mg/m$^2$. In some embodiments of the presently disclosed methods, a subject may be administered a maximum cumulative dose of daunorubicin that is greater than about 500 mg/m$^2$, 550 mg/m$^2$, 600 mg/m$^2$, 650 mg/m$^2$, or 700 mg/m$^2$, when the subject is administered a RARG agonist, either before, concurrently with, and/or after daunorubicin is administered to the subject.

In the disclosed methods, the subject may be undergoing or may be selected to undergo treatment with epirubicin. In clinical practice, because of side-effects such as cardiotoxicity, the maximum cumulative dose of epirubicin that is administered is ~900 mg/m$^2$. In some embodiments of the presently disclosed methods, a subject may be administered a maximum cumulative dose of epirubicin that is greater than about 800 mg/m$^2$, 850 mg/m$^2$, 900 mg/m$^2$, 950 mg/m$^2$, or 1000 mg/m$^2$, when the subject is administered a RARG agonist, either before, concurrently with, and/or after epirubicin is administered to the subject.

In the disclosed methods, the subject may be undergoing or may be selected to undergo treatment with idarubicin intravenously. In clinical practice, because of side-effects such as cardiotoxicity, the maximum cumulative dose of idarubicin that is administered intravenously is ~150 mg/m$^2$. In some embodiments of the presently disclosed methods, a subject may be administered a maximum cumulative dose of idarubicin intravenously that is greater than about 100 mg/m$^2$, 125 mg/m$^2$, 150 mg/m$^2$, 175 mg/m$^2$, or 200 mg/m$^2$, when the subject is administered a RARG agonist, either before, concurrently with, and/or after idarubicin is administered to the subject.

In the disclosed methods, the subject may be undergoing or may be selected to undergo treatment with idarubicin orally. In clinical practice, because of side-effects such as cardiotoxicity, the maximum cumulative dose of idarubicin that is administered orally is ~400 mg/m$^2$. In some embodiments of the presently disclosed methods, a subject may be administered a maximum cumulative dose of idarubicin orally that is greater than about 300 mg/m$^2$, 350 mg/m$^2$, 400 mg/m$^2$, 450 mg/m$^2$, or 500 mg/m$^2$, when the subject is administered a RARG agonist, either before, concurrently with, and/or after idarubicin is administered to the subject.

In the disclosed methods, the subject may be undergoing or may be selected to undergo treatment with an anthracycline chemotherapeutic agent and the subject is administered a RARG agonist, either before, concurrently with, or after the subject is administered the anthracycline chemotherapeutic agent. In some embodiments, the RARG agonist represses expression of TOP2B, for example by binding to the RARG and forming a complex that binds to the promoter for TOP2B and represses transcription of TOP2B.

In the disclosed methods, the subject may be undergoing or may be selected to undergo treatment with an anthracycline chemotherapeutic agent and the subject is administered a RARG agonist. In some embodiments, the RARG agonist is selective for the RARG and is not an agonist for the retinoic acid receptor alpha (RARA) or the retinoic acid receptor beta (RARB). Optionally, the RARG agonist may be an RARA agonist or antagonist and/or an RARB agonist or antagonist.

In the disclosed methods, the subject may be undergoing or may be selected to undergo treatment with an anthracycline chemotherapeutic agent and the subject is administered a RARG agonist RARG agonists are known in the art.

In some embodiments of the disclosed methods, the subject is administered palovarotene (4-[(E)-2-[5,5,8,8-tetramethyl-3-(1H-pyrazol-1-ylmethyl)-5,6,7,8-tetrahydronaphthalen-2-yl]ethenyl]benzoic acid). Palovarotene is sold by Clementia Pharmaceuticals and has a formula:

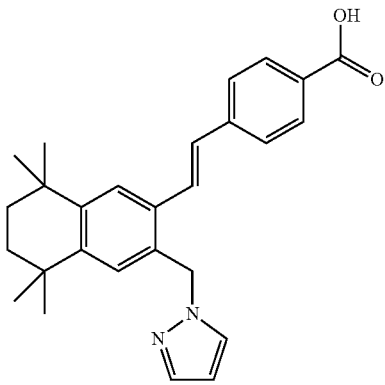 [SMILES: CC1(C)CCC(C)(C)c2cc(Cn3cccn3)c(/C=C/c3ccc(C(=O)O)cc3)cc21]

In some embodiments of the disclosed methods, the subject is administered an RARG agonist as disclosed in any of U.S. Published Application Nos. 2012/0214869; 2012/0016031; 2010/0273883; 2010/0261754; 2010/0130614; 2010/0130613; 2009/0036536; 2009/0023811; and 2007/0117761; which are assigned to Galderma Research & Development Boit, FR, and which contents of which are incorporated herein by reference in their entireties.

In some embodiments of the disclosed methods, the subject is administered an RARG agonist selected from the group consisting of, but not limited to AC 261066 (4-[4-(2-Butoxyethoxy-)-5-methyl-2-thiazolyl]-2-fluorobenzoic acid (AC 55649 (4'-Octyl-[1,1'-biphenyl]-4-carboxylic acid); adapalene (6-(4-Methoxy-3-tricyclo[3.3.1.13,7]dec-1-ylphenyl)-2-naphthalenecarboxylic acid); AM 580 (4-[(5,6,7,8-Tetrahydro-5,5,8,8-tetramethyl-2-naphthalenyl)carboxamido]benzoic acid); AM 80 (4-[[(5,6,7,8-Tetrahydro-5,5,8,8-tetramethyl-2-naphthalenyl)amino]carbonyl]benzoic acid); BMS 753 (4-[[(2,3-Dihydro-1,1,3,3-tetramethyl-2-oxo-1H-inden-5-yl)carbonyl]amino]benzoic acid); BMS 961 (3-Fluoro-4-[[2-hydroxy-2-(5,5,8,8-tetramethyl-5,6,7,8-tetrahydro-2-naphthalenyl)acetyl]amino]-benzoic acid); CD1530 (4-(6-Hydroxy-7-tricyclo[3.3.1.13,7]dec-1-yl-2-naphthalenyl)benzoic acid); CD 2314 (5-(5,6,7,8-Tetrahydro-5,5,8,8-tetramethyl-2-anthracenyl)-3-thiophenecarboxylic acid); CD437 (6-(4-Hydroxy-3-tricyclo[3.3.1.13,7]dec-1-ylphenyl)-2-naphthalenecarboxylic acid); CD55 (4-[(1E)-3-[3,5-bis(1,1-Dimethylethyl)phenyl]-3-oxo-1-propenyl]benzoic acid); isotretinoin (13-cis-retinoic acid); retinoic acid or all trans retinoic acid (ATRA) (3,7-Dimethyl-9-(2,6,6-trimethyl-1-cyclohexen-1-yl)-2E,4E,6E,8E-nonatetraenoic acid); tazarotene (6-[2-(3,4-Dihydro-4,4-dimethyl-2H-1-benzothiopyran-6-yl)ethynyl]-3-pyridinecarboxylic acid); and TTNPB (4-[(E)-2-(5,6,7,8-Tetrahydro-5,5,8,8-tetramethyl-2-naphthalenyl)-1-propenyl]benzoic acid).

In the disclosed methods, the subject may be undergoing or may be selected to undergo treatment with an anthracycline chemotherapeutic agent and the subject is administered a RARG agonist. The RARG agonist may be administered prior to, concurrently with, and/or after administering the anthracycline chemotherapeutic agent.

Children are especially sensitive to the undesirable side-effects of chemotherapy with anthracycline agents. In some embodiments of the disclosed methods, the subject is no more than 18, 17, 16, 15, 14, 13, 12, 11, 10, 9, 8, 7, 6, 5, 4, 3, 2, or 1 years of age.

Also disclosed herein are pharmaceutical compositions, kits, and therapeutic systems that comprise and/or utilize an RARG agonist. Suitable RARG agonists for the disclosed pharmaceutical compositions, kits, and therapeutic systems may include RARG agonists that repress expression of TOP2B. In some embodiments of the disclosed pharmaceutical compositions, kits, and therapeutic systems, the RARG agonist is a selective agonist for the RARG.

Suitable RARG agonists for the disclosed pharmaceutical compositions, kits, and therapeutic systems may include palovarotene (4-[(E)-2-[5,5,8,8-tetramethyl-3-(1H-pyrazol-1-ylmethyl)-5,6,7,8-tetrahydronaphthalen-2-yl]ethenyl]benzoic acid). Other suitable RARG agonists for the disclosed pharmaceutical compositions, kits, and therapeutic systems may include RARG agonists as disclosed in any of U.S. Published Application Nos. 2012/0214869; 2012/0016031; 2010/0273883; 2010/0261754; 2010/0130614; 2010/0130613; 2009/0036536; 2009/0023811; and 2007/0117761; the contents of which are incorporated herein in their entireties. Other suitable RARG agonists for the disclosed pharmaceutical compositions, kits, and therapeutic systems may include RARG agonists selected from the group consisting of, but not limited to AC 261066 (4-[4-(2-Butoxyethoxy-)-5-methyl-2-thiazolyl]-2-fluorobenzoic acid); AC 55649 (4'-Octyl-[1,1'-biphenyl]-4-carboxylic acid); adapalene (6-(4-Methoxy-3-tricyclo[3.3.1.13,7]dec-1-ylphenyl)-2-naphthalenecarboxylic acid); AM 580 (4-[(5,6,7,8-Tetrahydro-5,5,8,8-tetramethyl-2-naphthalenyl)carboxamido]benzoic acid); AM 80 (4-[[(5,6,7,8-Tetrahydro-5,5,8,8-tetramethyl-2-naphthalenyl)amino]carbonyl]benzoic acid); BMS 753 (4-[[(2,3-Dihydro-1,1,3,3-tetramethyl-2-oxo-1H-inden-5-yl)carbonyl]amino]benzoic acid); BMS 961 (3-Fluoro-4-[[2-hydroxy-2-(5,5,8,8-tetramethyl-5,6,7,8,-tetrahydro-2-naphthalenyl)acetyl]amino]-benzoic acid); CD1530 (4-(6-Hydroxy-7-tricyclo[3.3.1.13,7]dec-1-yl-2-naphthalenyl)benzoic acid); CD 2314 (5-(5,6,7,8-Tetrahydro-5,5,8,8-tetramethyl-2-anthracenyl)-3-thiophenecarboxylic acid); CD437 (6-(4-Hydroxy-3-tricyclo[3.3.1.13,7]dec-1-ylphenyl)-2-naphthalenecarboxylic acid); CD55 (4-[(1E)-3-[3,5-bis(1,1-Dimethylethyl)phenyl]-3-oxo-1-propenyl]benzoic acid); isotretinoin (13-cis-retinoic acid); retinoic acid or all trans retinoic acid (ATRA) (3,7-Dimethyl-9-(2,6,6-trimethyl-1-cyclohexen-1-yl)-2E,4E,6E,8E,-nonatetraenoic acid); tazarotene (6-[2-(3,4-Dihydro-4,4-dimethyl-2H-1-benzothiopyran-6-yl)ethynyl]-3-pyridinecarboxylic acid); and TTNPB (4-[(E)-2-(5,6,7,8-Tetrahydro-5,5,8,8-tetramethyl-2-naphthalenyl)-1-propenyl]benzoic acid).

Suitable anthracycline chemotherapeutic agents for the disclosed pharmaceutical compositions, kits, and therapeutic systems may include anthracyclines that intercalate within DNA and prevents the release of topoisomerase 2 β (TOP2B) from DNA bound to the TOP2B. In some embodiments of the disclosed pharmaceutical compositions, kits, and therapeutic systems the anthracycline is selected from the group consisting of doxorubicin, daunorubicin, epirubicin, idarubicin, and aldoxorubicin.

ILLUSTRATIVE EMBODIMENTS

Embodiment 1

A method for treating or preventing cardiotoxicity in a subject undergoing treatment with an anthracycline chemotherapeutic agent, the method comprising administering to the subject an agonist of the retinoic acid receptor gamma (RARG).

Embodiment 2

The method of embodiment 1, wherein the subject has a cell proliferative disease or disorder selected from the group consisting of bladder cancer, breast cancer, glioblastoma, lymphoma, leukemia, lung cancer, ovarian cancer, pancreatic cancer, soft tissue sarcoma, and thyroid cancer.

Embodiment 3

The method of any of the foregoing embodiments, wherein the subject has the T-allele of the single nucleotide polymorphism (SNP) rs2229774 (p. Ser427Leu).

Embodiment 4

The method of any of the foregoing embodiments, wherein the anthracycline intercalates within DNA and prevents the release of topoisomerase 2β (TOP2B) from DNA bound to the TOP2B.

Embodiment 5

The method of any of the foregoing embodiments, wherein the anthracycline is selected from the group consisting of doxorubicin, daunorubicin, epirubicin, idarubicin, and aldoxorubicin.

Embodiment 6

The method of any of the foregoing embodiment, wherein the anthracycline chemotherapeutic agent is doxorubicin and in the treatment method the subject is administered a maximum cumulative dose of doxorubicin that is greater than about 400 mg/m$^2$, 450 mg/m$^2$, 500 mg/m$^2$, 550 mg/m$^2$, or 600 mg/m$^2$.

Embodiment 7

The method of any of the foregoing embodiment, wherein the anthracycline chemotherapeutic agent is daunorubicin and in the treatment method the subject is administered a maximum cumulative dose of daunorubicin that is greater than about 500 mg/m$^2$, 550 mg/m$^2$, 600 mg/m$^2$, 650 mg/m$^2$, or 700 mg/m$^2$.

Embodiment 8

The method of any of the foregoing embodiments, wherein the anthracycline chemotherapeutic agent is epirubicin and in the treatment method the subject is administered a maximum cumulative dose of epirubicin that is greater than about 800 mg/m$^2$, 850 mg/m$^2$, 900 mg/m$^2$, 950 mg/m$^2$, or 1000 mg/m$^2$.

Embodiment 9

The method of any of the foregoing embodiments, wherein the anthracycline chemotherapeutic agent is idarubicin and in the treatment method the subject is administered intravenously a maximum cumulative dose of idarubicin that is greater than about 100 mg/m$^2$, 125 mg/m$^2$, 150 mg/m$^2$, 175 mg/m$^2$, or 200 mg/m$^2$.

Embodiment 10

The method of any of the foregoing embodiments, wherein the anthracycline chemotherapeutic agent is idarubicin and in the treatment method the subject is administered orally a maximum cumulative dose of idarubicin that is greater than about 300 mg/m$^2$, 350 mg/m$^2$, 400 mg/m$^2$, 450 mg/m$^2$, or 500 mg/m$^2$.

Embodiment 11

The method of any of the foregoing embodiments, wherein the RARG agonist represses expression of TOP2B.

Embodiment 12

The method of any of the foregoing embodiments, wherein the RARG agonist is a selective agonist for the RARG.

Embodiment 13

The method of any of the foregoing embodiments, wherein the RARG agonist is selected from the group consisting of palovarotene (4-[(E)-2-[5,5,8,8-tetramethyl-3-(1H-pyrazol-1-ylmethyl)-5,6,7,8-tetrahydronaphthalen-2-yl]ethenyl]benzoic acid); AC 261066 (4-[4-(2-Butoxyethoxy-)-5-methyl-2-thiazolyl]-2-fluorobenzoic acid); AC 55649 (4'-Octyl-[1,1'-biphenyl]-4-carboxylic acid); adapalene (6-(4-Methoxy-3-tricyclo[3.3.1.13,7]dec-1-ylphenyl)-2-naphthalenecarboxylic acid); AM 580 (4-[(5,6,7,8-Tetrahydro-5,5,8,8-tetramethyl-2-naphthalenyl)carboxamido]benzoic acid); AM 80 (4-[[(5,6,7,8-Tetrahydro-5,5,8,8-tetramethyl-2-naphthalenyl)amino]carbonyl]benzoic acid); BMS 753 (4-[[(2,3-Dihydro-1,1,3,3-tetramethyl-2-oxo-1H-inden-5-yl)carbonyl]amino]benzoic acid); BMS 961 (3-Fluoro-4-[[2-hydroxy-2-(5,5,8,8-tetramethyl-5,6,7,8,-tetrahydro-2-naphthalenyl)acetyl]amino]-benzoic acid); CD1530 (4-(6-Hydroxy-7-tricyclo[3.3.1.13,7]dec-1-yl-2-naphthalenyl)benzoic acid); CD 2314 (5-(5,6,7,8-Tetrahydro-5,5,8,8-tetramethyl-2-anthracenyl)-3-thiophenecarboxylic acid); CD437 (6-(4-Hydroxy-3-tricyclo[3.3.1.13,7]dec-1-ylphenyl)-2-naphthalenecarboxylic acid); CD55 (4-[(1E)-3-[3,5-bis(1,1-Dimethylethyl)phenyl]-3-oxo-1-propenyl]benzoic acid); isotretinoin (13-cis-retinoic acid); retinoic acid or all trans retinoic acid (ATRA) (3,7-Dimethyl-9-(2,6,6-trimethyl-1-cyclohexen-1-yl)-2E,4E,6E,8E,-nonatetraenoic acid); tazarotene (6-[2-(3,4-Dihydro-4,4-dimethyl-2H-1-benzothiopyran-6-yl)ethynyl]-3-pyridinecarboxylic acid); and TTNPB (4-[(E)-2-(5,6,7,8-Tetrahydro-5,5,8,8-tetramethyl-2-naphthalenyl)-1-propenyl]benzoic acid).

Embodiment 14

The method of any of the foregoing embodiments comprising administering the RARG agonist prior to administering the anthracycline chemotherapeutic agent.

Embodiment 15

The method of any of the foregoing embodiments comprising administering the RARG agonist concurrently with administering the anthracycline chemotherapeutic agent.

Embodiment 16

The method of any of the foregoing embodiments comprising administering the RARG agonist after administering the anthracycline chemotherapeutic agent.

Embodiment 17

The method of any of the foregoing embodiments, wherein the subject is no more than 18, 17, 16, 15, 14, 13, 12, 11, 10, 9, 8, 7, 6, 5, 4, 3, 2, or 1 years of age.

Embodiment 18

A pharmaceutical composition comprising a combination of an anthracycline chemotherapeutic agent and an agonist of the retinoic acid receptor gamma (RARG).

Embodiment 19

The pharmaceutical composition of embodiment 18, wherein the anthracycline chemotherapeutic agent intercalates within DNA and prevents the release of topoisomerase 2β (TOP2B) from DNA bound to the TOP2B.

Embodiment 20

The pharmaceutical composition of embodiment 18 or 19, wherein the anthracycline chemotherapeutic agent is selected from the group consisting of doxorubicin, daunorubicin, epirubicin, idarubicin, and aldoxorubicin.

Embodiment 21

The pharmaceutical composition of any of embodiments 18-20, wherein the RARG agonist represses expression of TOP2B.

Embodiment 22

The pharmaceutical composition of any of embodiments 18-21, wherein the RARG agonist is a selective agonist for the RARG.

Embodiment 23

The pharmaceutical composition of any of embodiments 18-22, wherein the RARG agonist is selected from the group consisting of Palovarotene™ (4 [(E)-2-[5,5,8,8-tetramethyl-3-(1H-pyrazol-1-ylmethyl)-5,6,7,8-tetrahydronaphthalen-2-yl]ethenyl]benzoic acid), AC 261066 (4-[4-(2-Butoxy-ethoxy-)-5-methyl-2-thiazolyl]-2-fluorobenzoic acid(AC 55649 (4'-Octyl-[1,1'-biphenyl]-4-carboxylic acid); adapalene (6-(4-Methoxy-3-tricyclo[3.3.1.13,7]dec-1-ylphenyl)-2-naphthalenecarboxylic acid); AM 580 (4-[(5,6,7,8-Tetrahydro-5,5,8,8-tetramethyl-2-naphthalenyl)carboxamido]benzoic acid); AM 80 (4-[[(5,6,7,8-Tetrahydro-5,5,8,8-tetramethyl-2-naphthalenyl)amino]carbonyl]benzoic acid); BMS 753 (4-[[(2,3-Dihydro-1,1,3,3-tetramethyl-2-oxo-1H-inden-5-yl)carbonyl]amino]benzoic acid); BMS 961 (3-Fluoro-4-[[2-hydroxy-2-(5,5,8,8-tetramethyl-5,6,7,8,-tetrahydro-2-naphthalenyl)acetyl]amino]-benzoic acid); CD1530 (4-(6-Hydroxy-7-tricyclo[3.3.1.13,7]dec-1-yl-2-naphthalenyl)benzoic acid); CD 2314 (5-(5,6,7,8-Tetrahydro-5,5,8,8-tetramethyl-2-anthracenyl)-3-thiophenecarboxylic acid); CD437 (6-(4-Hydroxy-3-tricyclo[3.3.1.13,7]dec-1-ylphenyl)-2-naphthalenecarboxylic acid); CD55 (4-[(1E)-3-[3,5-bis(1,1-Dimethylethyl)phenyl]-3-oxo-1-propenyl]benzoic acid); isotretinoin (13-cis-retinoic acid); retinoic acid or all trans retinoic acid (ATRA) (3,7-Dimethyl-9-(2,6,6-trimethyl-1-cyclohexen-1-yl)-2E,4E,6E,8E,-nonatetraenoic acid); tazarotene (6-[2-(3,4-Dihydro-4,4-dimethyl-2H-1-benzothiopyran-6-yl)ethynyl]-3-pyridinecarboxylic acid); and TTNPB (4-[(E)-2-(5,6,7,8-Tetrahydro-5,5,8,8-tetramethyl-2-naphthalenyl)-1-propenyl]benzoic acid).

Embodiment 24

A kit or treatment system comprising as components an anthracycline chemotherapeutic agent and an agonist of the retinoic acid receptor gamma (RARG).

Embodiment 25

The kit or treatment system of embodiment 24, wherein the anthracycline intercalates within DNA and prevents the release of topoisomerase 2 β (TOP2B) from DNA bound to the TOP2B.

Embodiment 26

The kit or treatment system of embodiment 24 or 25, wherein the anthracycline is selected from the group consisting of doxorubicin, daunorubicin, epirubicin, idarubicin, and aldoxorubicin.

Embodiment 27

The kit or treatment system of any of embodiments 24-26, wherein the RARG agonist represses expression of TOP2B.

Embodiment 28

The kit or treatment system of any of embodiments 24-27, wherein the RARG agonist is a selective agonist for the RARG.

Embodiment 29

The kit or treatment system of any of embodiments 24-28, wherein the RARG agonist is selected from the group consisting of Palovarotene™ (4 [(E)-2-[5,5,8,8-tetramethyl-3-(1H-pyrazol-1-ylmethyl)-5,6,7,8-tetrahydronaphthalen-2-yl]ethenyl]benzoic acid), AC 261066 (4-[4-(2-Butoxy-ethoxy-)-5-methyl-2-thiazolyl]-2-fluorobenzoic acid(AC 55649 (4'-Octyl-[1,1'-biphenyl]-4-carboxylic acid); adapalene (6-(4-Methoxy-3-tricyclo[3.3.1.13,7]dec-1-ylphenyl)-2-naphthalenecarboxylic acid); AM 580 (4-[(5,6,7,8-Tetrahydro-5,5,8,8-tetramethyl-2-naphthalenyl)carboxamido]benzoic acid); AM 80 (4-[[(5,6,7,8-Tetrahydro-5,5,8,8-tetramethyl-2-naphthalenyl)amino]carbonyl]benzoic acid); BMS 753 (4-[[(2,3-Dihydro-1,1,3,3-tetramethyl-2-oxo-1H-inden-5-yl)carbonyl]amino]benzoic acid); BMS 961 (3-Fluoro-4-[[2-hydroxy-2-(5,5,8,8-tetramethyl-5,6,7,8,-tetrahydro-2-naphthalenyl)acetyl]amino]-benzoic acid); CD1530 (4-(6-Hydroxy-7-tricyclo[3.3.1.13,7]dec-1-yl-2-naphthalenyl)benzoic acid); CD 2314 (5-(5,6,7,8-Tetrahydro-5,5,8,8-tetramethyl-2-anthracenyl)-3-thiophenecarboxylic acid); CD437 (6-(4-Hydroxy-3-tricyclo[3.3.1.13,7]dec-1-ylphenyl)-2-naphthalenecarboxylic acid); CD55 (4-[(1E)-3-[3,5-bis(1,1-Dimethylethyl)phenyl]-3-oxo-1-propenyl]benzoic acid); isotretinoin (13-cis-retinoic acid); retinoic acid or all trans retinoic acid (ATRA) (3,7-Dimethyl-9-(2,6,6-trimethyl-1-cyclohexen-1-yl)-2E,4E,6E,8E,-nonatetraenoic acid); tazarotene (6-[2-(3,4-Dihydro-4,4-dimethyl-2H-1-benzothiopyran-6-yl)ethynyl]-3-pyridinecarboxylic acid); and TTNPB (4-[(E)-2-(5,6,7,8-Tetrahydro-5,5,8,8-tetramethyl-2-naphthalenyl)-1-propenyl]benzoic acid).

EXAMPLES

The following Example is illustrative and is not intended to limit the scope of the claimed subject matter.
GWAS Validation Using Patient-Specific hiPSC Identifies Doxorubicin-Induced Cardiotoxicity Protective Drugs
Summary
Doxorubicin is effective in treating a range of malignancies, but its use is limited by dose-dependent cardiotoxicity. A recent genome-wide association study (GWAS) identified a SNP (rs2229774) in retinoic acid receptor-γ (RARG) as statistically associated with increased risk of doxorubicin-induced cardiotoxicity (DIC). Here, we utilize human induced pluripotent stem cell-derived cardiomyocytes (hiPSC-CMs) to validate this deleterious SNP and determine its mechanism of action. We show that hiPSC-CMs from patients with rs2229774 are more sensitive to DIC, independently confirming the accuracy of the hiPSC-CM DIC model. By knockout and overexpression of RARG by CRISPR/Cas9 we confirm that RARG is the effector gene in this DIC predisposition model, which we then further substantiate by showing that correction of rs2229774 eliminates increased doxorubicin susceptibility. We go on to determine the mechanism of this RARG variant effect is mediated via suppression of TOP2B expression and activation of the cardioprotective ERK pathway. We use these patient-specific hiPSC-CMs as a drug discovery platform, determining that the RARG agonist CD1530 dramatically attenuates DIC, confirming that this protective effect is successful in an established in vivo mouse model of DIC. Thus, we demonstrate for the first time that hiPSC-CMs can be used as a powerful precision medicine tool for GWAS validation, with simultaneous pharmacogenomics-led drug discovery in a human model with direct potential for clinical translation. This study provides a strong rationale for clinical pre-chemotherapy genetic screening for rs2229774 and a foundation for the clinical use of RARG agonist treatment to protect cancer patients from DIC.
Introduction
Advances in pharmacogenomics have been driven by both candidate gene and genome-wide association studies (GWAS) and have resulted in the identification of numerous single nucleotide polymorphisms (SNPs) statistically associated with drug efficacy and toxicity. There is great need to develop suitable tools to fully validate these variants as studies can be underpowered, and variants discovered can be in non-coding regions, not change the amino acid sequence, or be in genes whose connection to drug efficacy or toxicity is totally unknown. Human models are required in order to establish variant function, as prior non-human models have proven inapplicable to patients (Cheng et al., 2011). A major advantage of human models is that they can provide in-depth and relevant mechanistic insight into how a specific genetic variant alters drug efficacy or toxicity (Musunuru et al., 2018), while providing a useful platform for subsequent drug discovery and facilitating rapid translation to the clinic.

The anthracycline doxorubicin (Adriamycin) is a prime candidate for this type of pharmacogenomic analysis. Doxorubicin is utilized in nearly 60% of pediatric cancer treatments (Hudson et al., 2013; van Dalen et al., 2014) and 35% of breast cancer treatments, and has made a substantial contribution to the improvement in average 5-year cancer survival rate, which exceeds 80% today. However, the presence of dose-dependent cardiotoxicity was recognized almost immediately after the introduction of doxorubicin treatment began (Lefrak et al., 1973; Swain et al., 2003; Von Hoff et al., 1979). 7-10% of all childhood cancer survivors will develop heart failure up to 30 years after diagnosis (Mulrooney et al., 2009; van der Pal et al., 2012), and the risk of congestive heart failure in adult survivors of childhood cancer is 12 times higher compared to their siblings (Oeffinger et al., 2006). Despite its cardiotoxicity, doxorubicin is still widely used, due to the lack of suitable alternatives.

The high inter-individual variability in predisposition to DIC (Granger, 2006; Hasan et al., 2004; Krischer et al., 1997) has prompted more than 40 candidate gene SNP association studies (Blanco et al., 2012; Wojnowski et al., 2005), and a small number of GWASs including our recent study on 456 pediatric cancer patients treated with anthracyclines (73 cases and 383 controls). This study identified the correlation (odds ratio=4.7, $P=5.9 \times 10^{-8}$) of a non-synonymous coding variant rs2229774 (S427L, 12,53605545,G,A) in RARG, encoding retinoic acid receptor-γ, with DIC in both the original and in two replication cohorts (Aminkeng et al., 2015). Although RARG has been known to play a role in cardiac looping during early development (Iulianella and Lohnes, 2002), the role of RARG in the mature heart is currently unknown. rs2229774 occurs in approximately 8% of the population (minor allele frequency of ~0.08, ExAC (Lek et al., 2016)) and is only 16 bp downstream of the sequence that encodes the ligand binding domain of RARG (FIG. 1a). rs2229774 is predicted to be damaging to RARG function (PROVEAN/SIFT score 0.047). Although GWAS data such as these represent a potential major advance in applying a pharmacogenomic approach to cardio-oncology (Magdy et al., 2016), the connection between these SNP associations and clinical cardiotoxicity is far from proven (Boyle et al., 2017).

Our prior work has demonstrated that human induced pluripotent stem cell-derived cardiomyocytes (hiPSC-CMs) accurately recapitulate patients' predilection to DIC (Burridge et al., 2016). Briefly, hiPSC-CMs from breast cancer patients who developed DIC recapitulate that increased risk in vitro, with decreased cell viability, metabolic function, contraction, sarcomeric structure, calcium handling, and increased reactive oxygen species (ROS) production when exposed to doxorubicin, compared to hiPSC-CMs from patients who were treated with doxorubicin but did not experience cardiotoxicity.

Using this platform, we validate the GWAS-identified variant rs2229774 as directly causative in DIC, confirming that cells from patients harboring this variant are at higher risk of DIC. We discover that a small molecule RARG agonist significantly attenuates cardiomyocyte doxorubicin sensitivity both in vitro and in vivo, reducing murine acute cardiotoxicity by almost 50%. Further analyses reveal that RARG-associated DIC risk is mediated via two established mechanisms of cardiotoxicity, direct repression of TOP2B and regulation of ERK phosphorylation-mediated cardioprotection, pathways known to lead to downstream modulation of mitochondrial integrity. We have thus used patient-derived hiPSC-CMs as a novel platform to confirm a GWAS suspected variant, discover the mechanism underlying the effect of that SNP, and develop and test a novel cardioprotective strategy using RARG agonists suitable for further clinical studies. Pre-chemotherapy genetic screening for rs2229774 and/or RARG agonist treatments have the potential to protect cancer patients from DIC.

Results

Our previous work identified the DIC-associated RARG variant rs2229774 in a Canadian pediatric patient cohort and validated it in both Dutch and US patient populations (Aminkeng et al., 2015). We returned to the Canadian cohort and specifically re-recruited these well-phenotyped, doxorubicin-exposed patients, using the original inclusion criteria (Table 1).

TABLE 1

Patient inclusion and exclusion criteria for study.

| Inclusion Criteria | Exclusion Criteria |
|---|---|
| Diagnosis of cancer | Unwilling to consent/assent to ≤10 ml blood draw |
| Treatment with doxorubicin (Adriamycin ™) | |
| Age ≤18 years at time of treatment | No documentation of pre-chemotherapy echocardiography shortening fraction |
| Documentation of pre-chemotherapy shortening fraction ≤30% | |
| For affected patients only: shortening fraction of ≤24% or signs and symptoms of cardia compromise requiring intervention based on CTCAEv3. Only echo ≤21 d after doxorubicin dose are to be considered. | |
| For control patients: shortening fraction of ≤24% and no symptoms of cardiac compromise for at least 5 years after treatment | |

We recruited three patients with the heterozygous rs2229774 variant and cardiotoxicity (S427L-1, -2, -3) and three control patients without the variant and without cardiotoxicity (Control-1, -2, -3) (FIG. 1a and Table 2).

Figure 6:
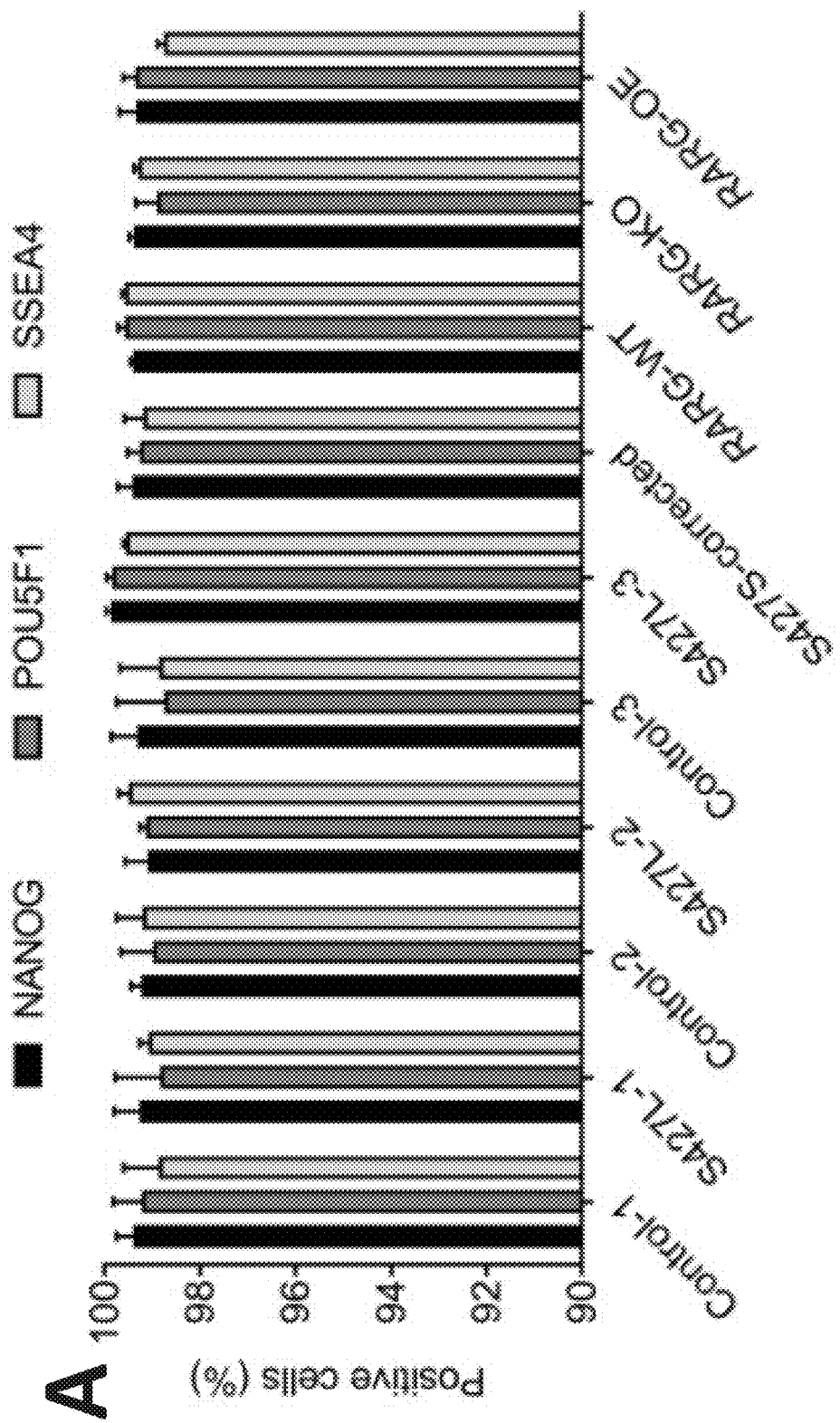
FIG. 6. Generation and characterization of patient-specific hiPSC-CMs. (a) Flow cytometry analysis of pluripotency markers in all hiPSC lines, n=3 replicates for each hiPSC line. (b) Schematic of cardiac differentiation protocol. (c) Representative immunfluorescent staining images for cardiac markers troponin T (TNNT2) and α-actinin (ACTN2). (d) Flow cytometry analysis for the percentage of the cardiac troponin T (TNNT2) or myosin heavy chain (MYH) positive cells derived from all hiPSC lines, n=3 replicates for each line. Throughout, data are represented as mean±s.e.m. Scale bar, 25 μm.
Figure 6:
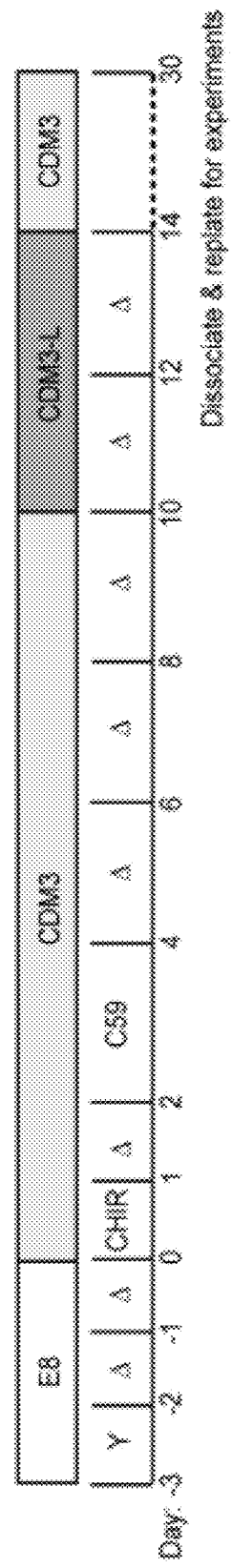
Figure 6:
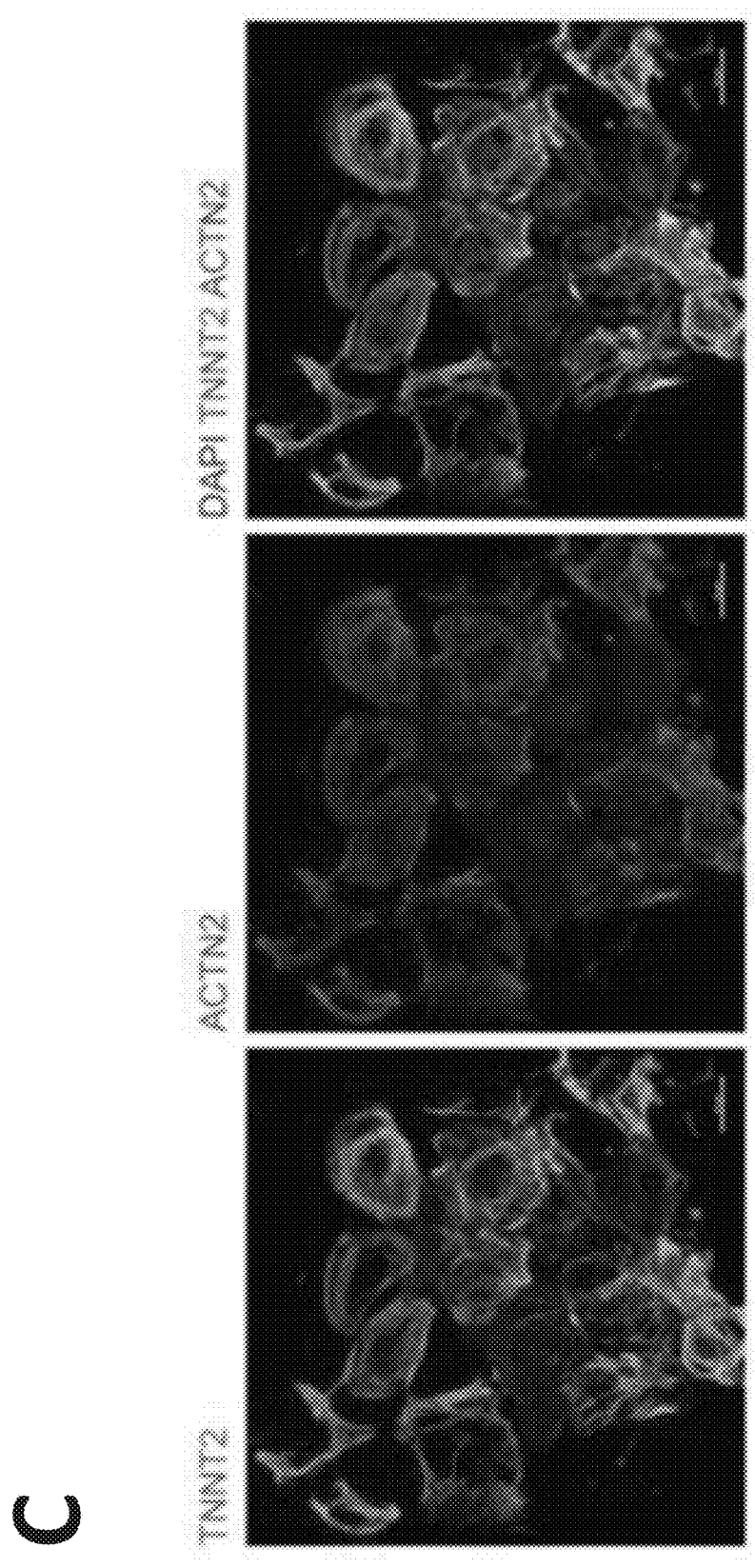
Figure 6:
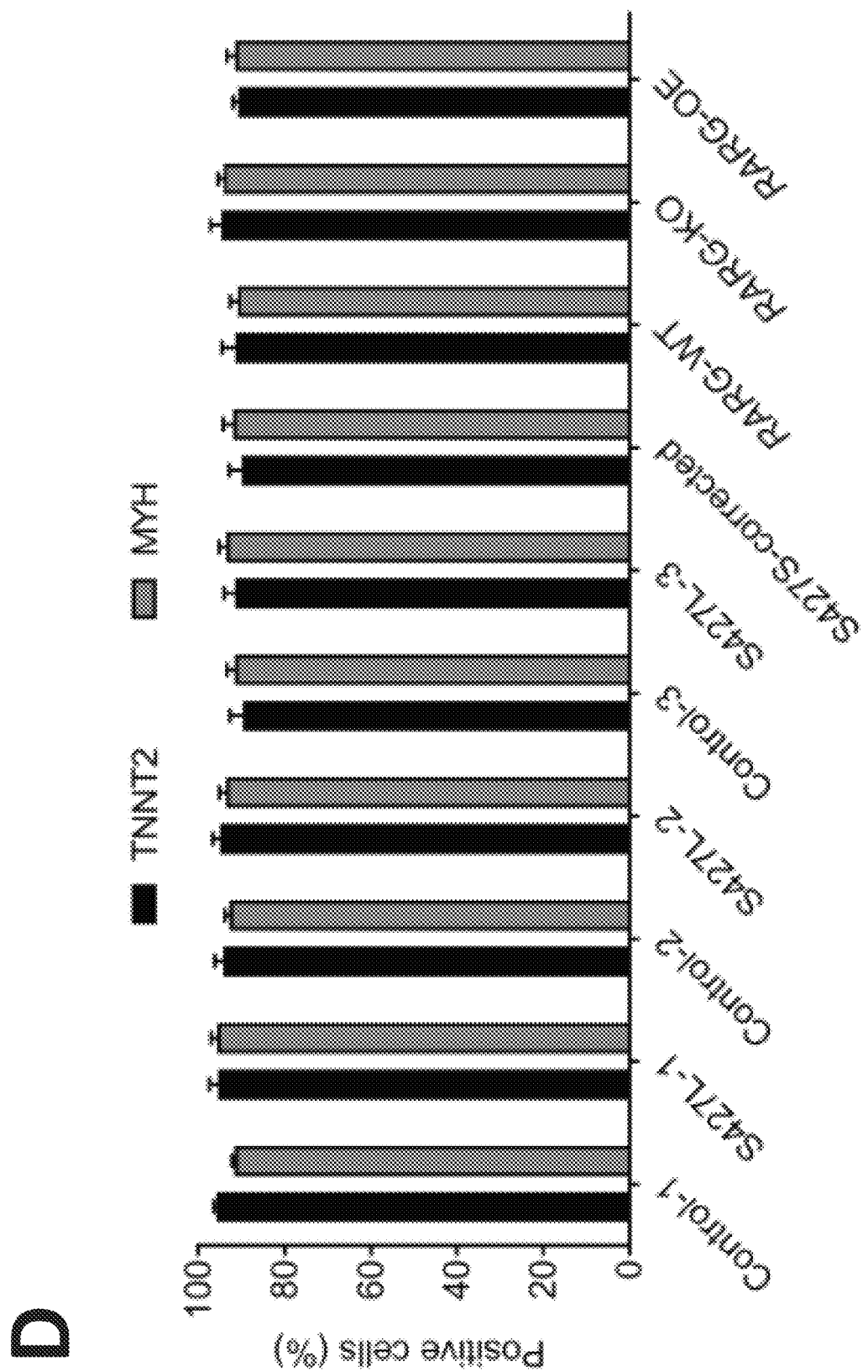
Figure 8:
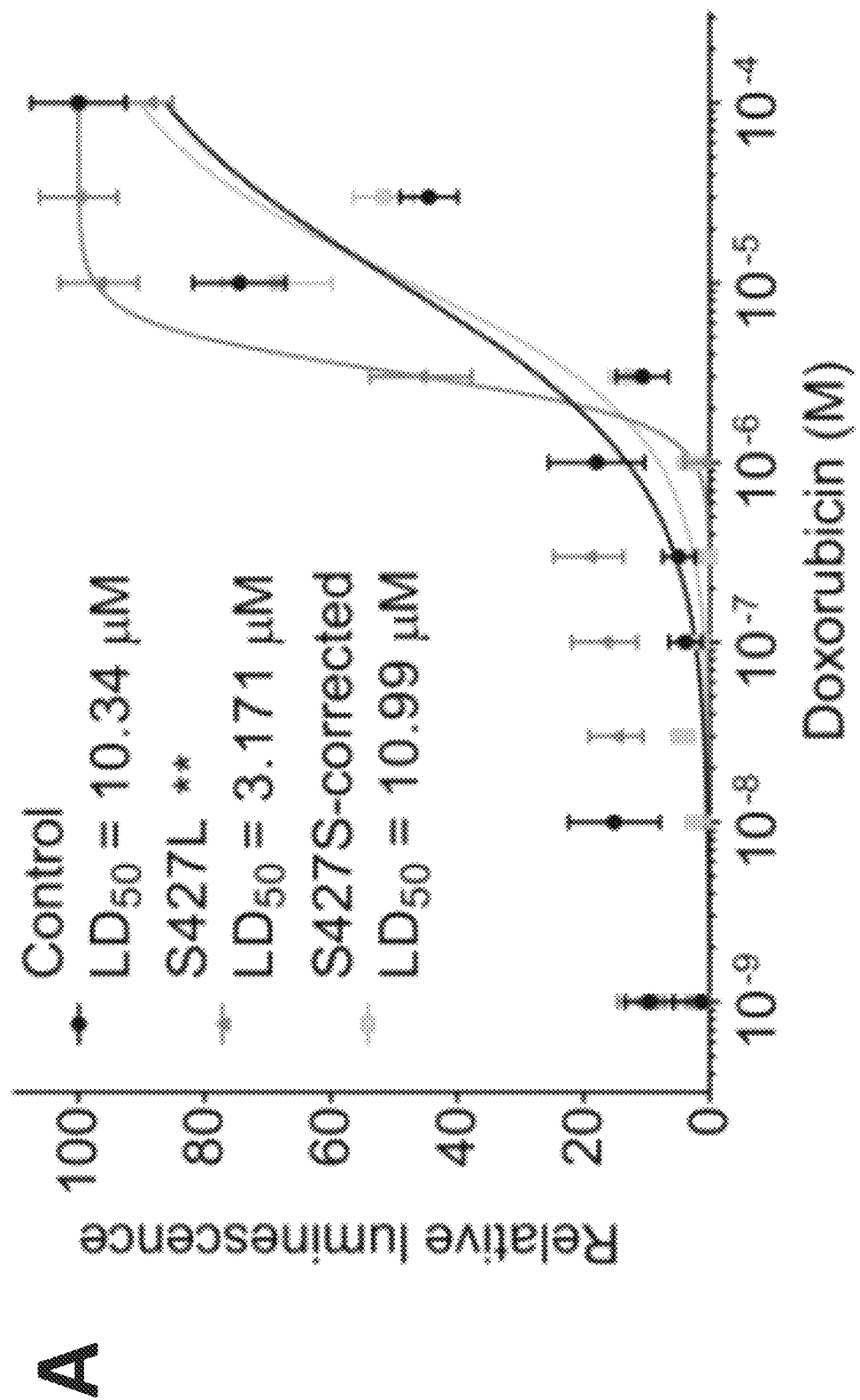
FIG. 8. RARG overexpression and TOP2B knockout in isogenic hiPSC-CMs protects against doxorubicin-induced cardiotoxicity. (a and b) Effect of doxorubicin (24 h) on the level of hydrogen peroxide ($H_2O_2$) in hiPSC-CMs. Control: n=6, S427L: n=28, S427L-corrected: n=19, RARG-WT: n=32, RARG-KO: n=26, RARG-OE: n=26. (c) Representative images of JC-10 staining for assessing mitochondrial membrane potential in isogenic hiPSC-CMs, after treatment with doxorubicin at the indicated concentrations for 24 h. Scale bar, 100 μm. (d) Schematic of the CRISPR/Cas9-mediated strategy to knockout the TOP2B gene. Shown is the genomic locus of TOP2B, an enlarged view of the first exon with start codon (highlighted in blue), PAM and gRNA targeting sequences (underlined), cutting site of Cas9 (vertical line) and PCR primers for sanger sequencing. (e) Table summarizing all targeted modifications in the isogenic hiPSC line. Indels were determined by Sanger sequencing. (f) Western blot showing knockout of TOP2B in the isogenic hiPSC line. Sequencing and western blot confirmed knockout clones were maintained for subsequent analysis. (g) Effect of doxorubicin (72 h) on hiPSC-CM viability. TOP2B-WT: n=26, TOP2B-KO: n=26, RARG-OE: n=17. Throughout, data are represented as mean±s.e.m. P<0.005; *P<0.0001; by F-test.
Figure 8:
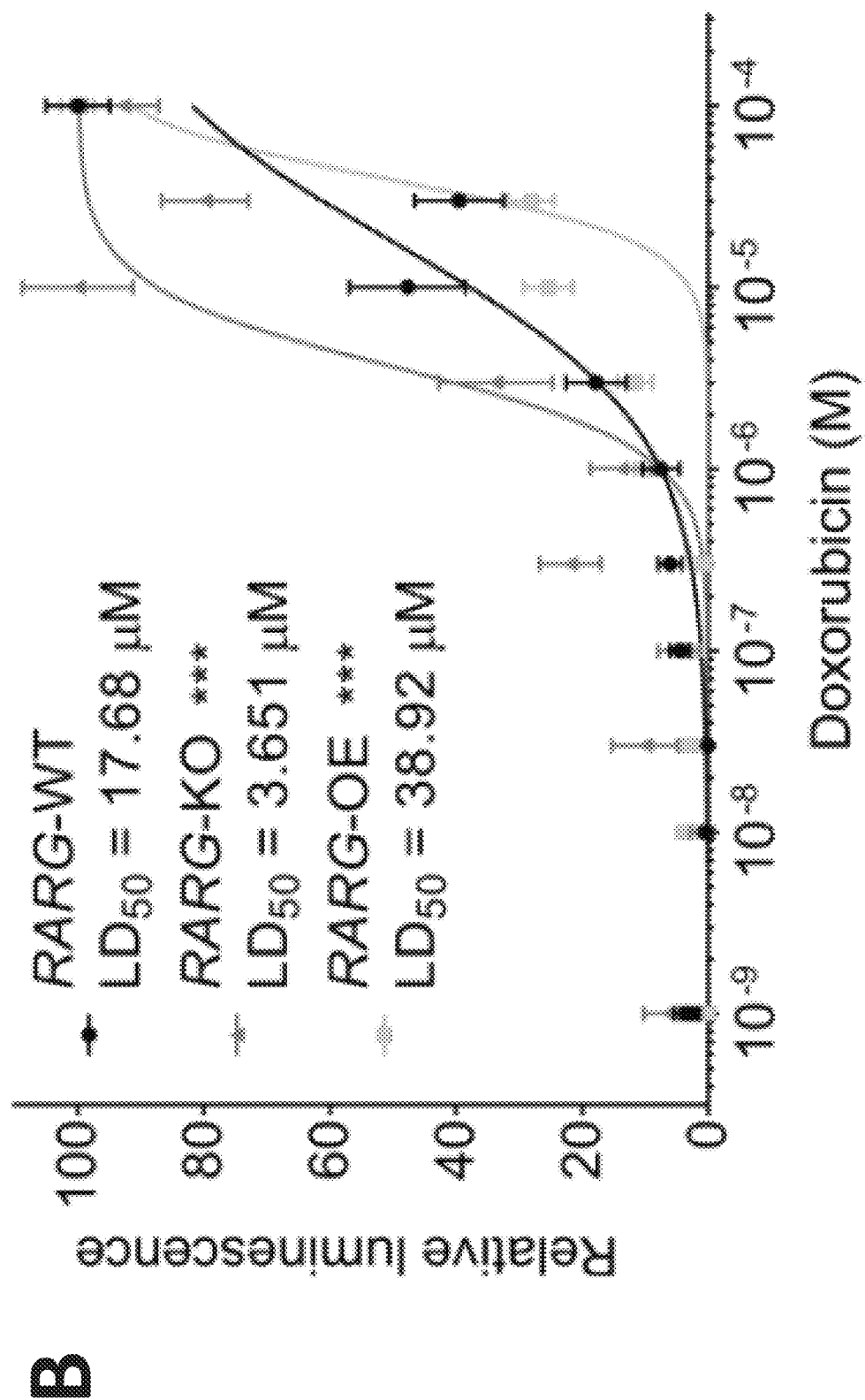
Figure 8:
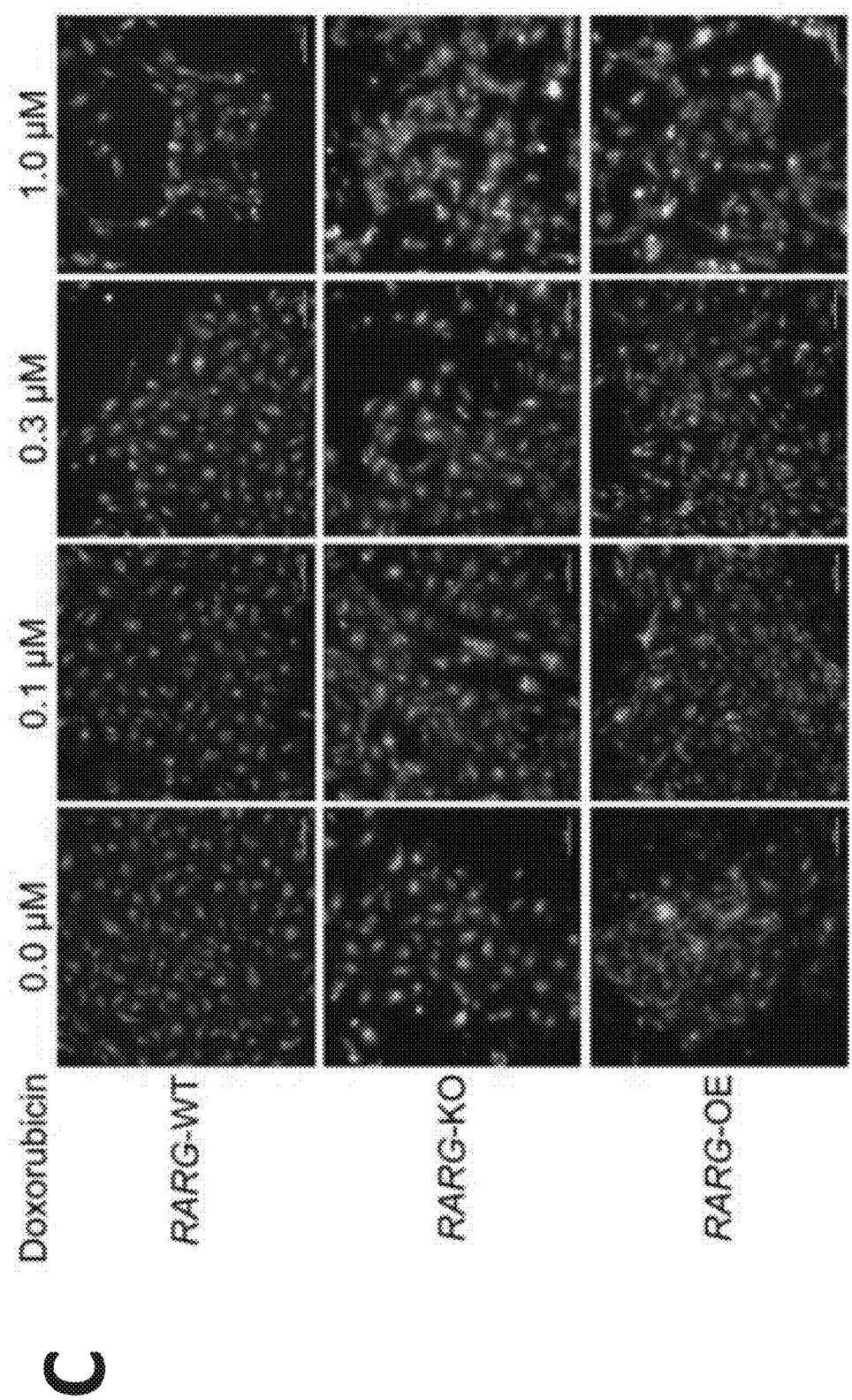
Figure 8:
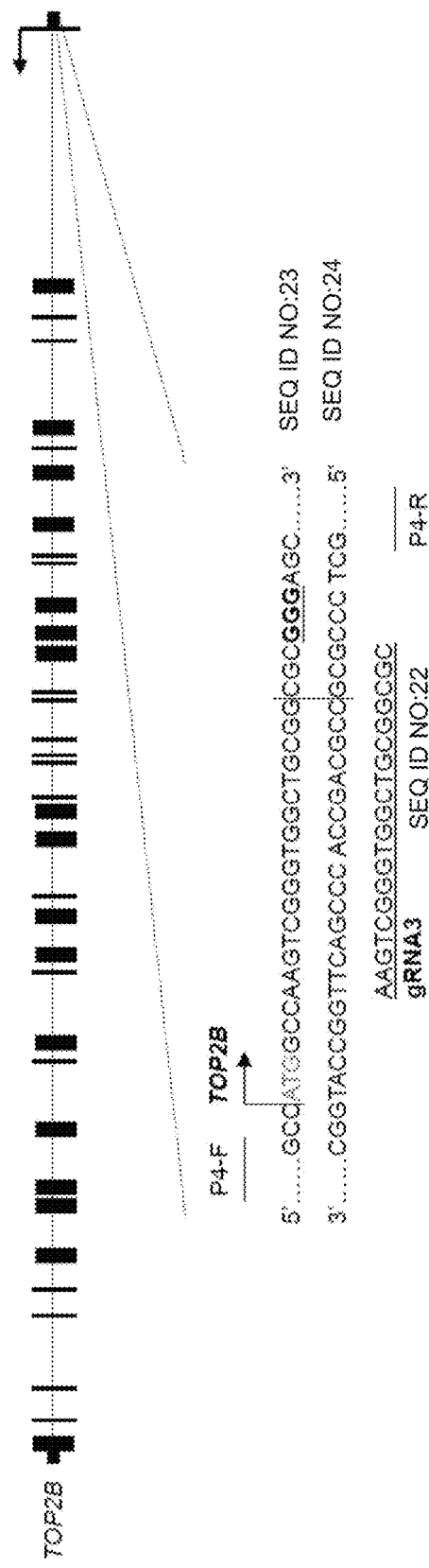
Figure 8:
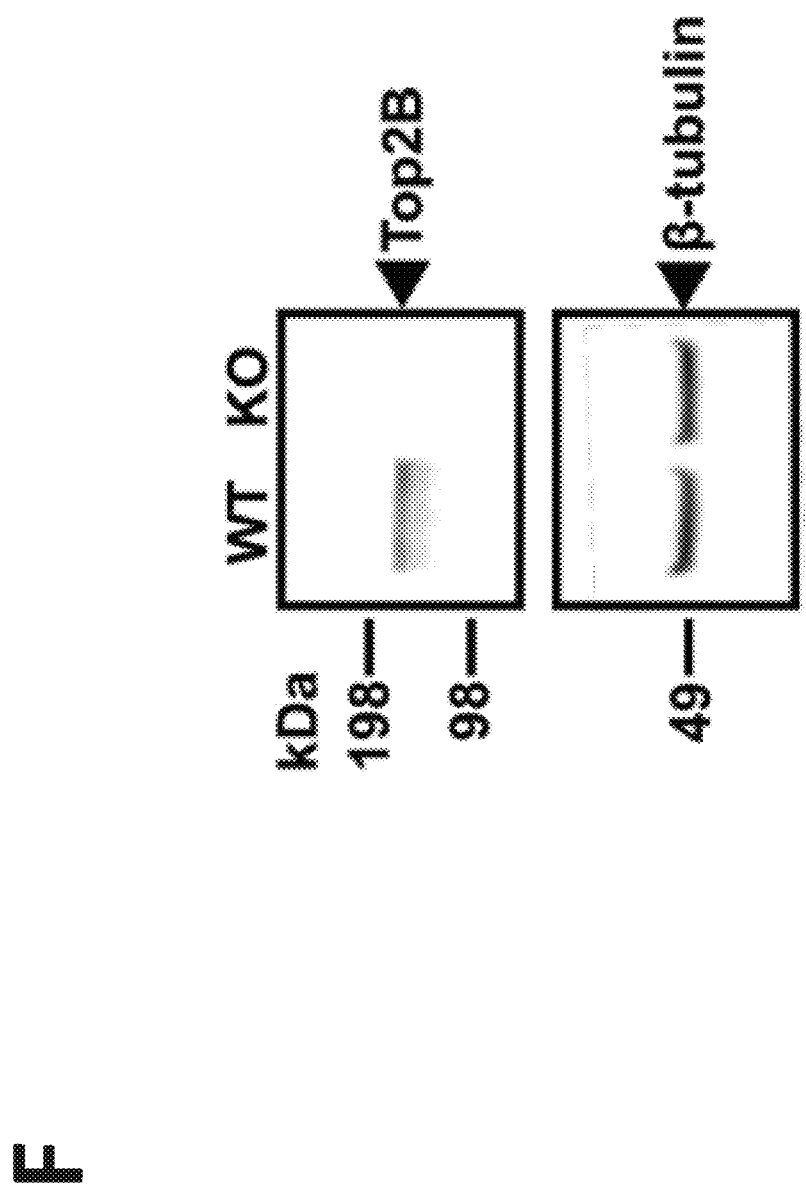
Figure 8:
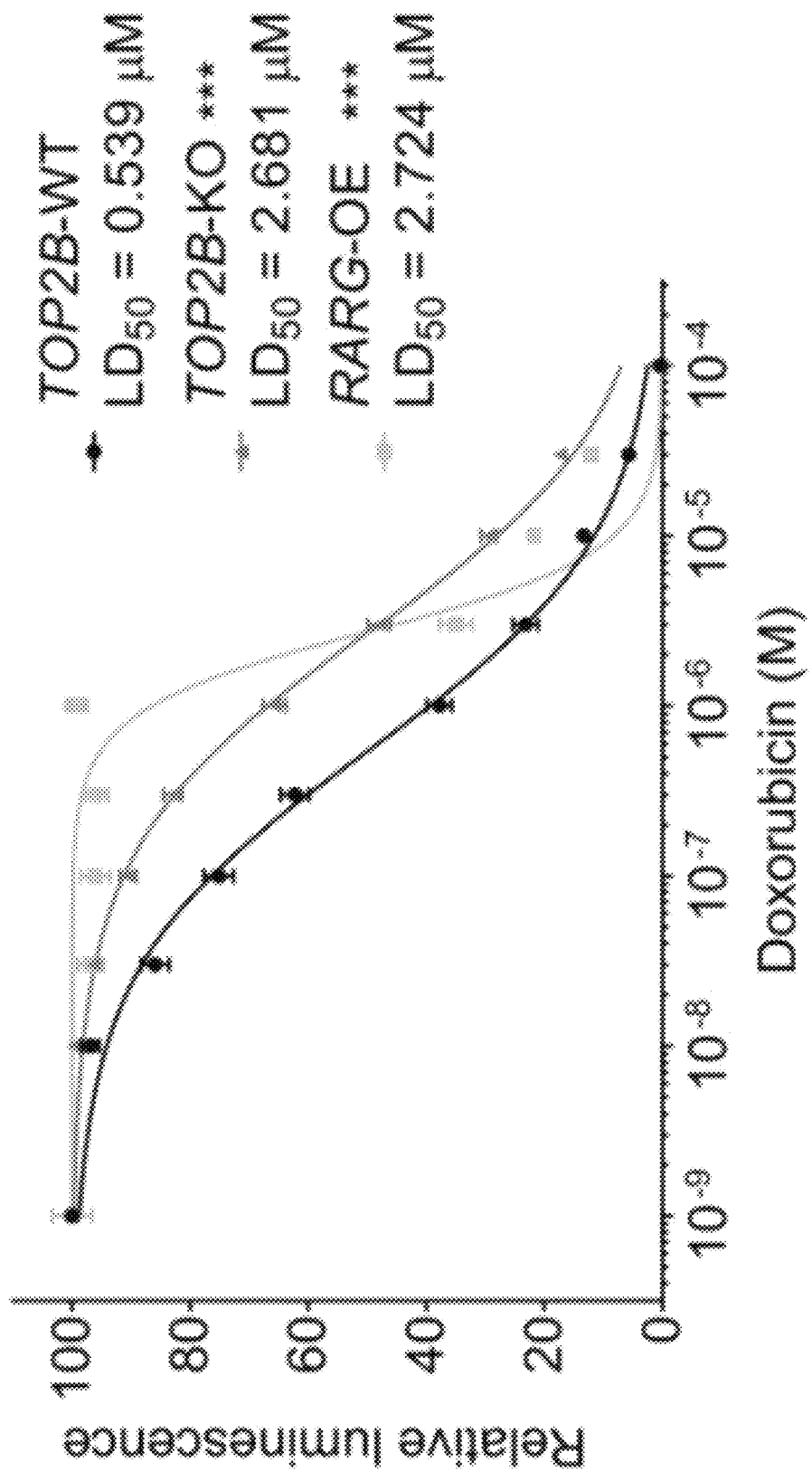

We derived hiPSCs from peripheral blood of these individuals, and all cell lines passed standard tests for pluripotency and genomic stability (Peterson and Loring, 2014) (FIG. 6a). Next, we differentiated these patient-derived hiPSCs into cardiomyocytes using our established protocol (Burridge et al., 2014), resulting in an average cardiomyocyte purity of >90% (FIG. 6b-d).

hiPSC-CMs with the rs2229774 variant recapitulate patients' increased risk of DIC. We first sought to determine whether hiPSC-CMs with the RARG variant could recapitulate patient-specific increased risk of DIC in vitro. A concentration-dependent increase in sarcomeric disarray is a well-established effect of doxorubicin, demonstrated in both neonatal rat ventricular cardiomyocytes (Minotti et al., 2004) and in our previous work in hiPSC-CMs (Burridge et al., 2016). As assessed by immunofluorescent imaging, we observed a consistent effect of sarcomeric disarray in S427L hiPSC-CMs but not in control cells treated with 0.5 µM doxorubicin for 24 h (FIG. 1b). Along with cytoskeletal damage, the S427L hiPSC-CMs showed significantly reduced cell viability after a 72 h treatment with doxorubicin, as compared to the control cells at all concentrations tested ($P<0.0001$), with half-maximal lethal doses ($LD_{50}$) of 0.63 µM and 2.622 µM for S427L and control cells, respectively (FIG. 1c). After 24 h of doxorubicin treatment, apoptosis analysis demonstrated a concentration-dependent increase in cells positive for caspase 3 and 7 activity, with $LD_{50}$ of 1.228 µM for S427L cells and 2.078 µM for control cells (FIG. 1d), suggesting that S427L hiPSC-CMs were more susceptible to programmed cell death. As oxidative stress is one of the major mechanisms underlying the cardiotoxic effects of doxorubicin, we assessed ROS production after 24 h of doxorubicin treatment. Reactive oxygen species (ROS) levels were significantly ($P<0.005$) higher in S427L than in the control cells, across the tested concentrations (FIG. 8a). Another mechanism for doxorubicin cardiotoxicity is induction of DNA damage, so we next assessed the level of double-stranded DNA breaks by staining for phosphorylated H2A histone family member X (γH2AX). We observed a concentration-dependent increase in DNA damage (FIG. 1e), and the level of DNA damage was significantly higher in S427L cells than in control cells, at all doxorubicin concentrations tested (FIG. 1f). Combined, these data confirm that hiPSC-CMs from patients with the rs2229774 SNP are more sensitive to DIC.

Figure 7:
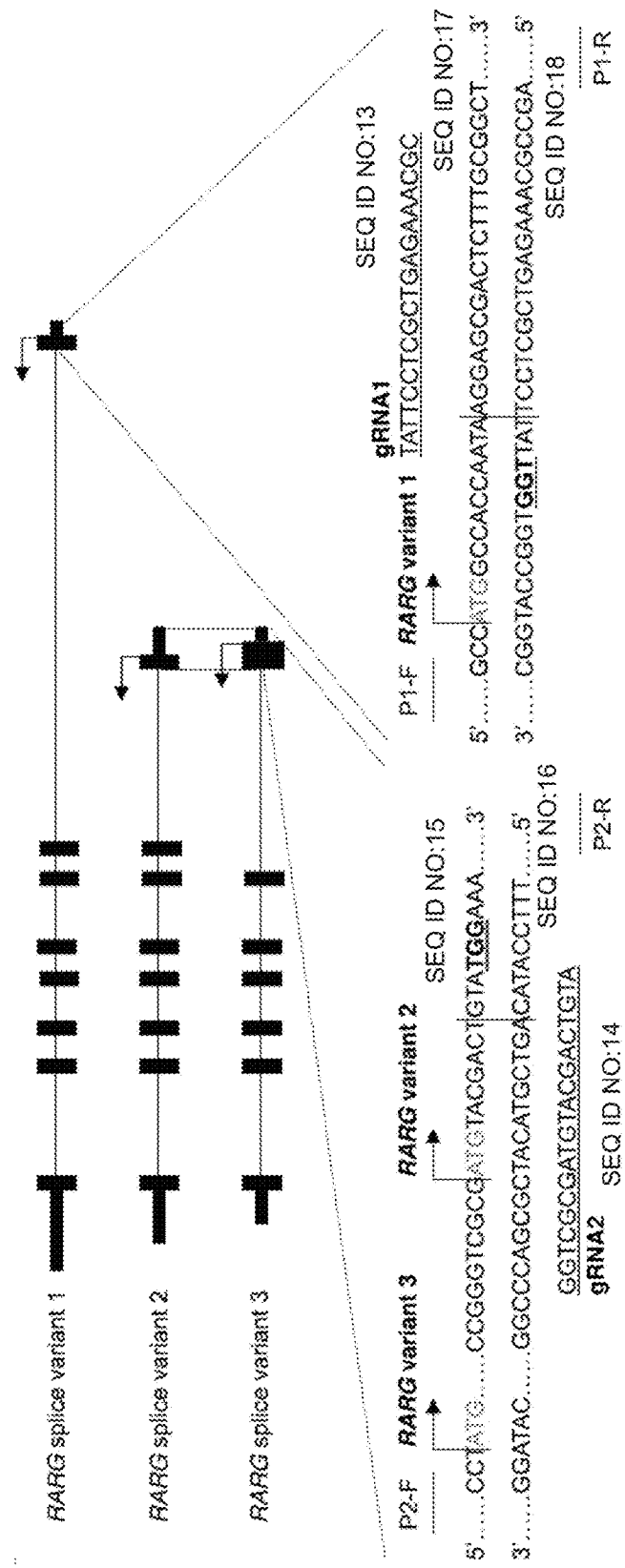
FIG. 7. CRISPR/Cas9-mediated knockout and overexpression of the RARG gene in the isogenic hiPSCs. (a) Schematic of the CRISPR/Cas9-mediated strategy to knockout the RARG gene. Shown are the genomic loci of the three major RARG splice variants, an enlarged view of the first exon with alternative start codon (highlighted in blue), PAM and gRNA targeting sequences (underlined), cutting site of Cas9 (vertical line) and PCR primers for sanger sequencing. (b) Schematic of the CRISPR/Cas9-mediated strategy for overexpression of the RARG gene. Shown are the genomic locus of the PPP1R12C gene, an enlarged view of the AAVS1 locus in the first intron of PPP1R12C, PAM and gRNA targeting sequence (underlined), cutting site of Cas9 (vertical line) and PCR primers for sanger sequencing of the RARG cDNA plasmid (containing most prevalent RARG splice variant 1 cDNA). (c) Table summarizing all targeted modifications in the isogenic hiPSC line. All targeted modifications were determined by Sanger sequencing. One knockout clone with confirmed indels causing frameshift near alternative start codons of all major RARG splice variants and clones with correct RARG cDNA insertion were maintained for subsequent analysis.
Figure 7:
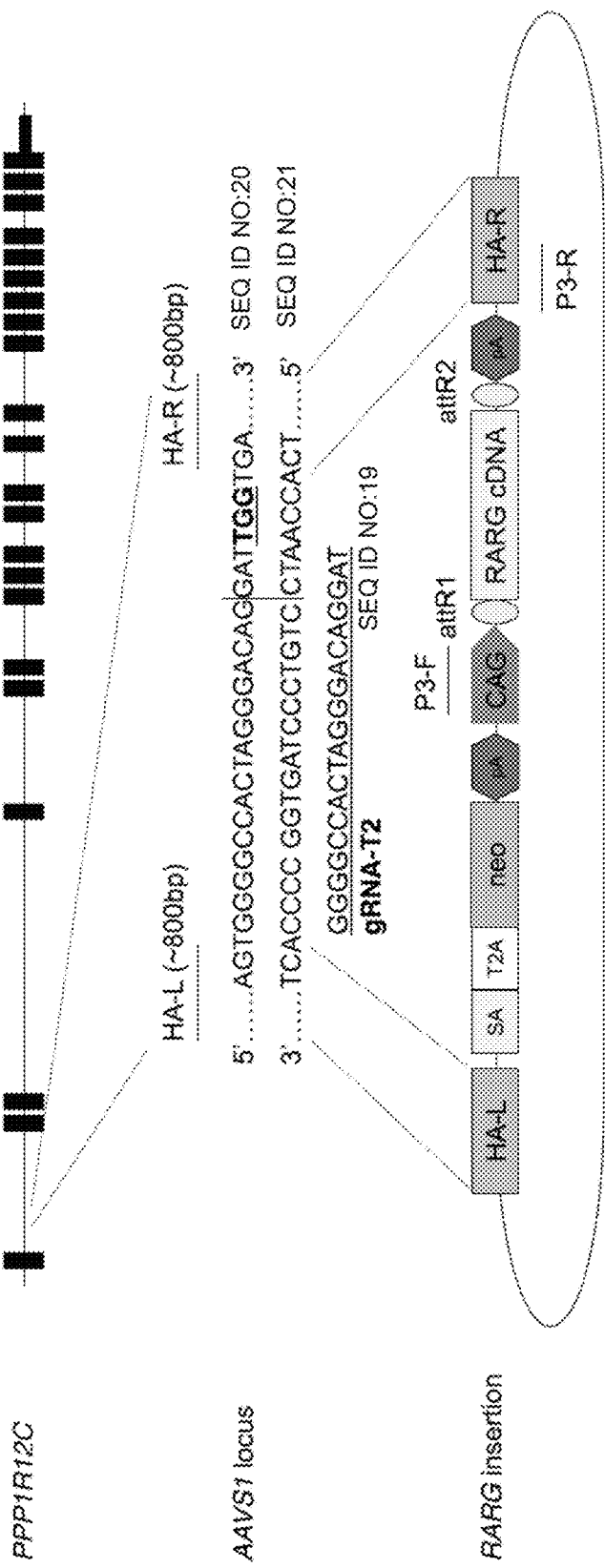

Loss of function of RARG leads to increased DIC in hiPSC-CMs. To validate the role of RARG in regulating DIC, we generated knockout (RARG-KO) and overexpression (RARG-OE) hiPSC-CMs from an isogenic control hiPSC line using CRISPR/Cas9-mediated genome editing (FIG. 7). Altered RARG expression in these lines was

TABLE 2

Doxorubicin-treated patients recruited in this study.

| Code | Anthracycline | Cardiotoxocity | Gender | Age of Treatment | Cancer Diagnosis | Heart Radiation* | rs2229774 |
|---|---|---|---|---|---|---|---|
| Control-1 | Yes | No | Male | 5.1 | Wilm's Tumor | Yes | G_G |
| Control-2 | Yes | No | Male | 1.6 | ALL | No | G_G |
| Control-3 | Yes | No | Female | 4.3 | ALL | No | G_G |
| S427L-1 | Yes | Yes | Male | 13.8 | Ewing's Sarcoma | No | A_G |
| S427L-2 | Yes | Yes | Male | 5.3 | Ewing's Sarcoma | Yes | A_G |
| S427L-3 | Yes | Yes | Female | 1.5 | Hepatocarcinoma | No | A_G |
| Isotope | No | NA | Male | NA | NA | No | G_G |

Figure 2:
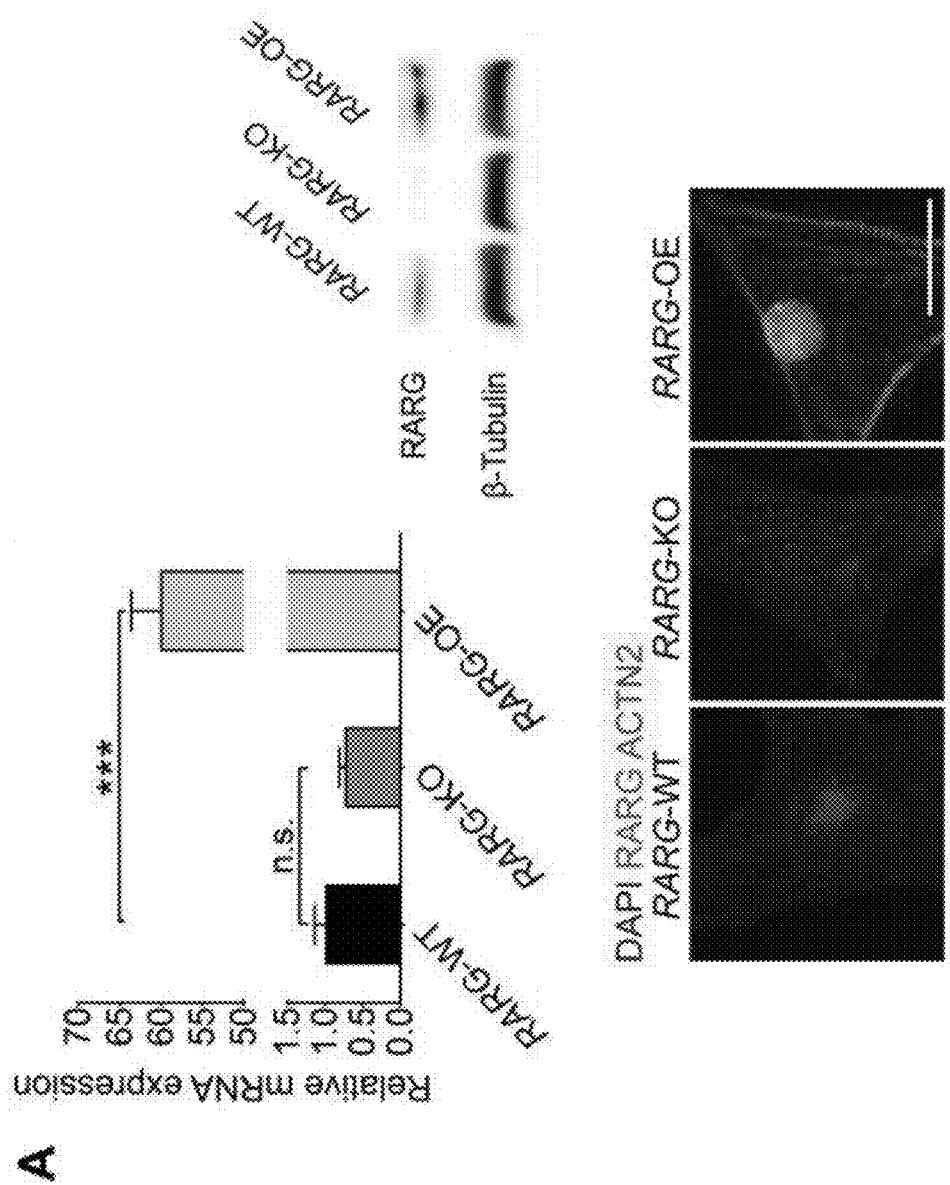
FIG. 2. Validation of RARG expression as correlated with doxorubicin-induced cardiotoxicity. (a) Expression of RARG in hiPSC-CMs with CRISPR/Cas9-mediated RARG knockout (KO) and AAVS1-based RARG overexpression (OE) in an isogenic hiPSC line, detected by real-time PCR (top left), western blot (top right), and immunofluorescent staining (bottom). (b) Representative images for sarcomeric organization in isogenic hiPSC-CMs after 24 h treatment with doxorubicin at the indicated concentrations, as assessed by immunofluorescence staining for α-actinin (ACTN2) and cardiac troponin T (TNNT2). (c) Effect of doxorubicin (72 h) on hiPSC-CM viability. RARG-WT: n=27, RARG-KO: n=13, RARG-OE: n=17. (d) Effect of doxorubicin (24 h) on caspase 3 and 7 activity in hiPSC-CMs. RARG-WT: n=15, RARG-KO: n=18, RARG-OE: n=32. (e) Representative images for immunofluorescent staining of γH2AX, after treatment of hiPSC-CMs with the indicated concentrations of doxorubicin for 24 h. (f) Quantification of γH2AX staining in hiPSC-CMs by flow cytometry. RARG-WT: n=5, RARG-KO: n=7, RARG-OE: n=10. Throughout, data are represented as mean±s.e.m. *$P<0.05$; $P<0.005$; *$P<0.0001$; n.s., not significant; by F-test (c and d) or ANOVA (a and f). Scale bars, 25 μm.
Figure 2:
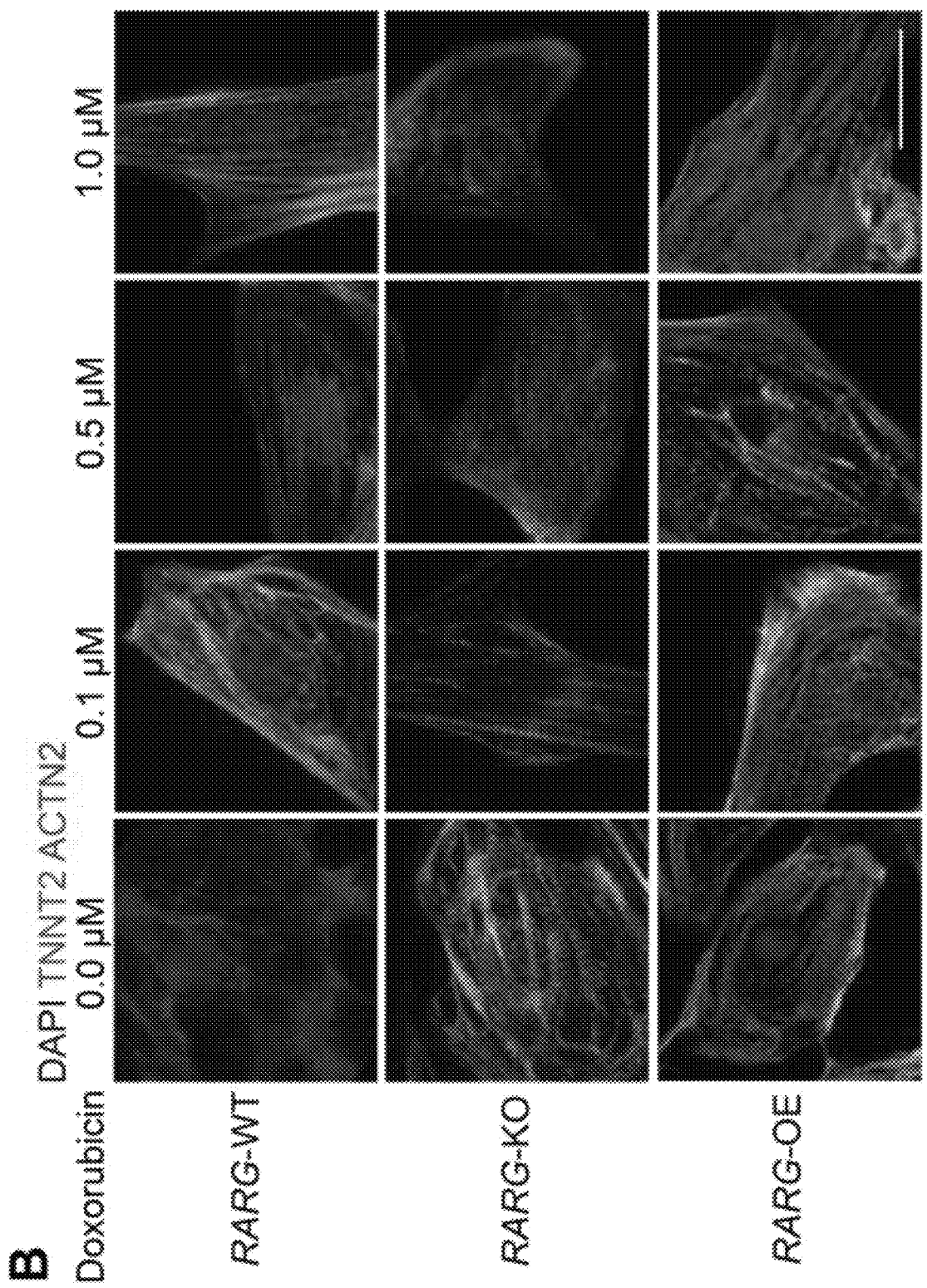
Figure 2:
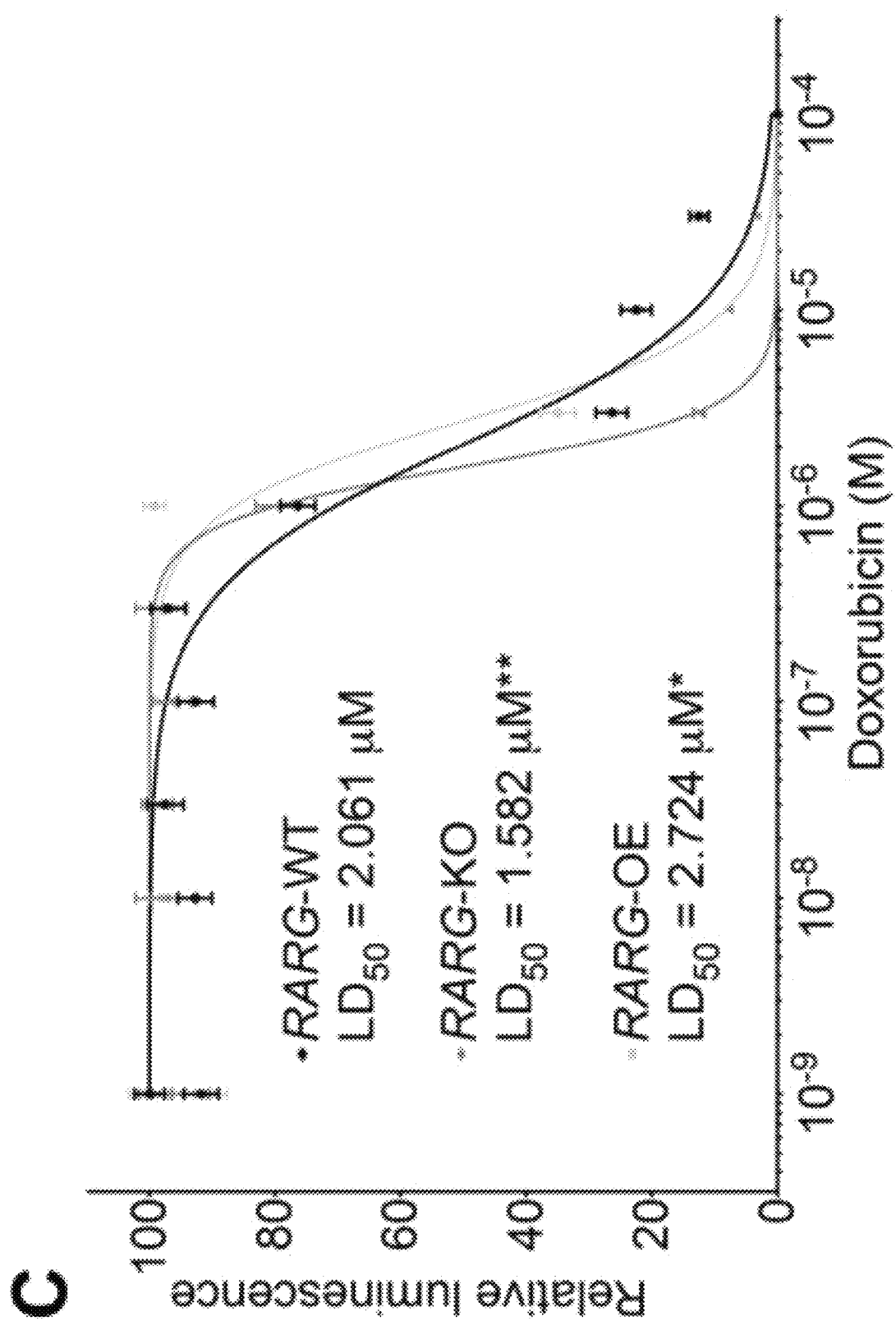
Figure 2:
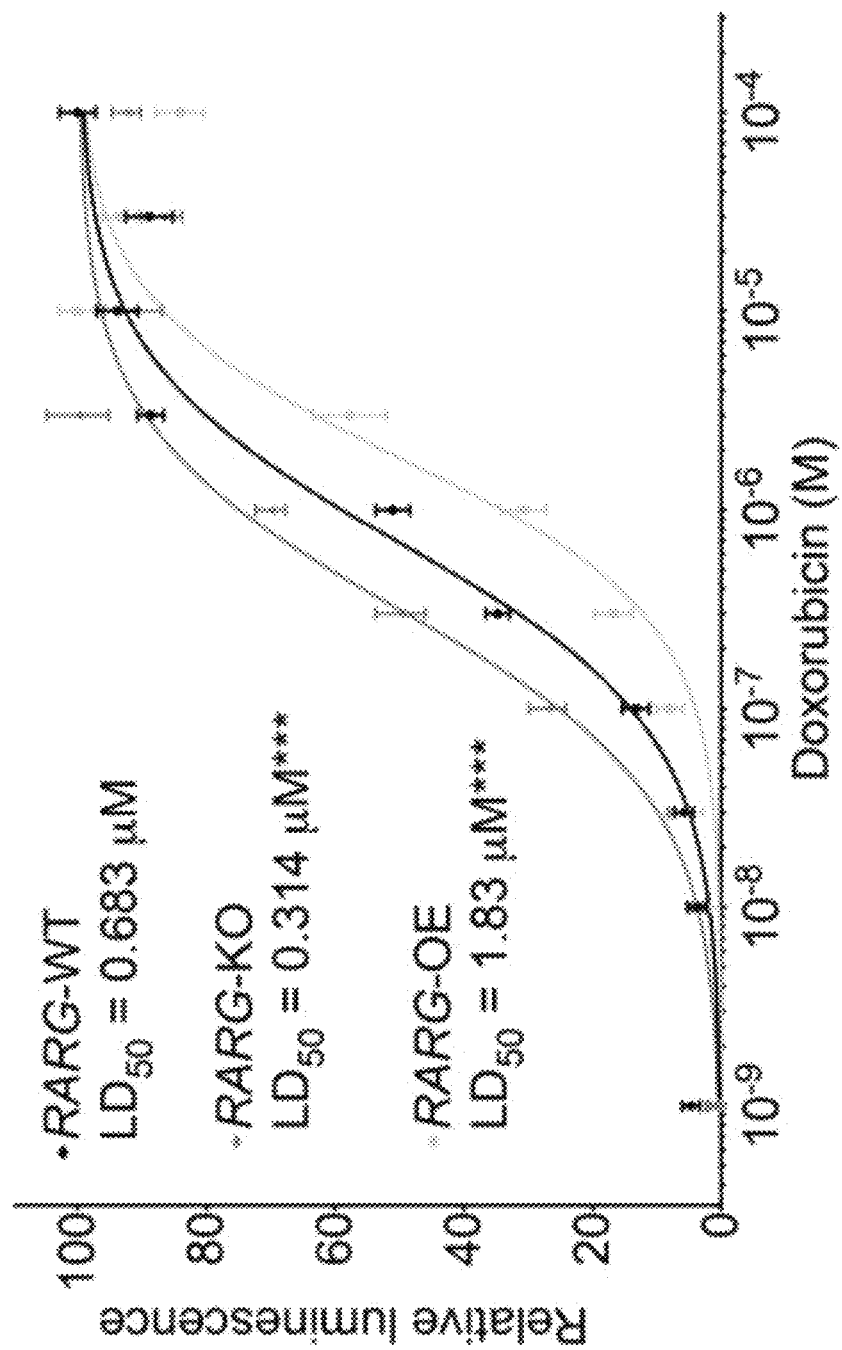
Figure 2:
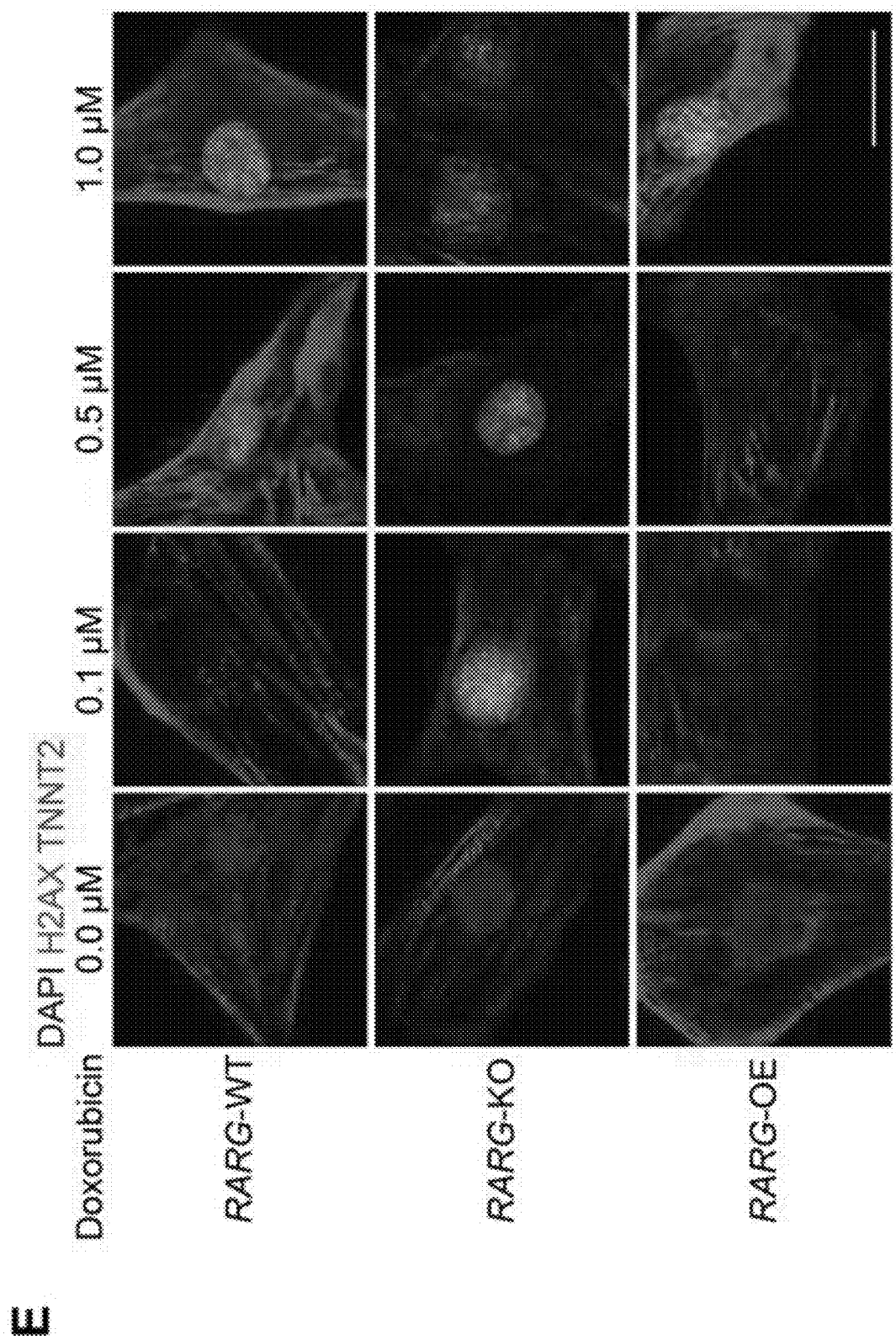
Figure 2:
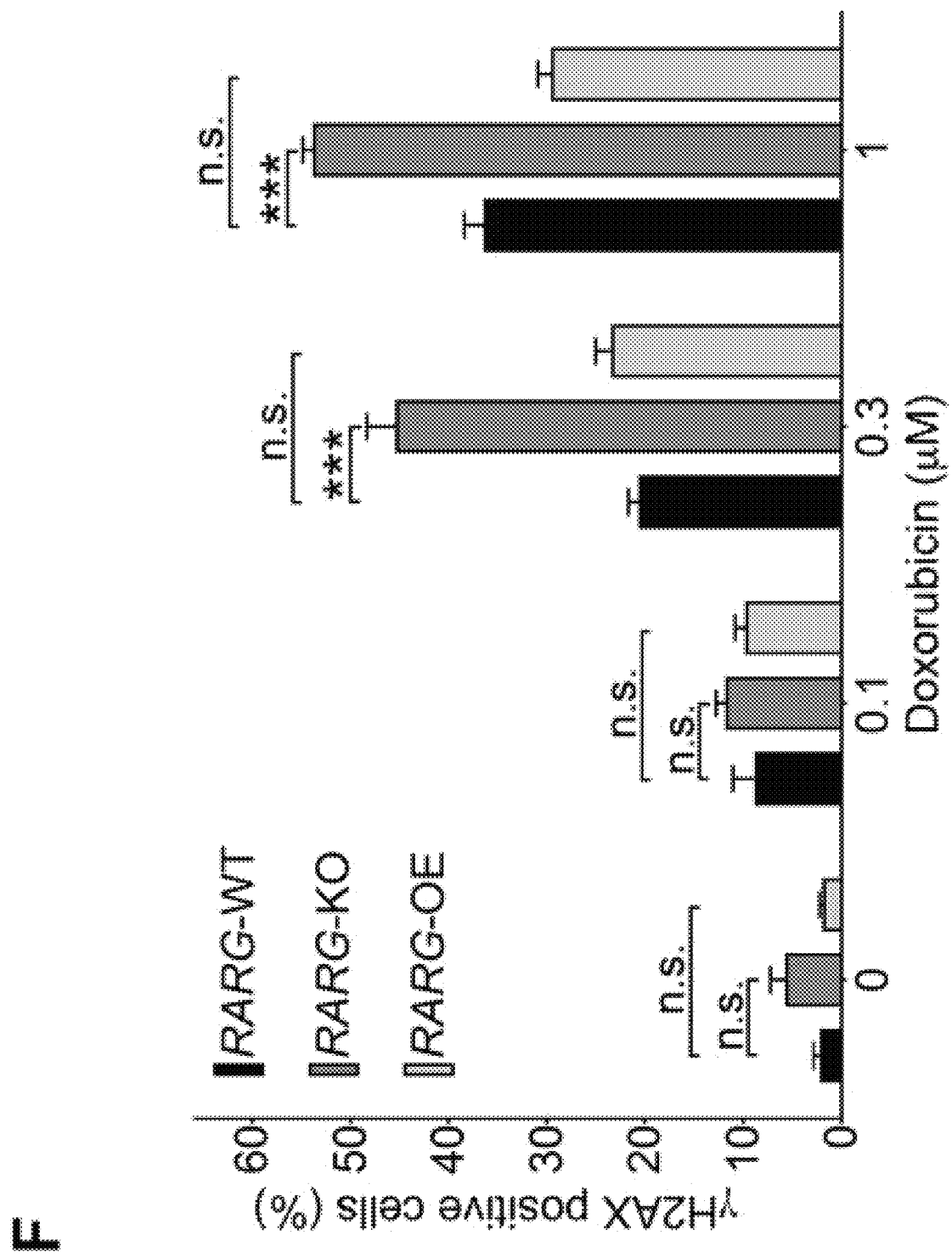

*Heart radiation therapy includes significant radiation exposure to the heart or surrounding tissue. This includes mantle and mediastinal radiation, whole-lung radiation, whole-abdomen or upper abdominal radiation, left-side flank radiation and total-body irradiation.
NA, not applicable.

confirmed at the RNA level by real-time PCR, and at the protein level by Western blot and immunofluorescent imaging (FIG. 2a). At the basal level, both of these lines were phenotypically indistinguishable from their isogenic control and differentiated normally into cardiomyocytes (FIG. 6), indicating that RARG was not required for pluripotency or cardiac differentiation in vitro. We observed a consistent sarcomeric disarray in RARG-KO cells treated with 0.5 µM of doxorubicin, whereas this effect was rarely seen in RARG-OE cells, even at 1 µM of doxorubicin compared with RARG-WT cells (FIG. 2b). Consistently, RARG-KO hiPSC-CMs showed significantly reduced cell viability (P<0.005), whereas RARG-OE cells showed significantly improved viability (P<0.05), as compared to RARG-WT cells at all doxorubicin concentrations tested, with $LD_{50}$ of 1.582 µM, 2.724 µM, and 2.061 µM for RARG-KO, RARG-OE, and RARG-WT cells, respectively (FIG. 2c). Analysis of apoptosis via caspase 3 and 7 activity demonstrated a doxorubicin concentration-dependent increase, with $LD_{50}$ of 0.314 µM, 1.83 µM, and 0.683 µM for RARG-KO, RARG-OE, and RARG-WT cells, respectively (FIG. 2d), suggesting that knockout of RARG increased doxorubicin-induced apoptosis, while overexpression attenuated it. Furthermore, we observed a doxorubicin concentration-dependent increase in ROS production (FIG. 8b), mitochondrial membrane dysregulation (FIG. 8c), and DNA damage (FIGS. 2e and f), and the levels of ROS, mitochondrial dysfunction, and DNA damage were significantly higher in RARG-KO hiPSC-CMs than in RARG-WT and RARG-OE hiPSC-CMs. Collectively, these data confirm that RARG expression has an important role in influencing the level of DIC and suggest that loss of function of RARG underlies the effect of the rs2229774 SNP in DIC.

Doxorubicin treatment results in S427L-dependent transcriptome changes in patient-derived hiPSC-CMs. We next sought to investigate transcriptome changes of S427L and control hiPSC-CMs in response to 1 µM doxorubicin for 24 h, using an unbiased approach. Principal component analysis (PCA) of RNA-seq data in all 37,557 genes revealed a clear distinction in hiPSC-CMs before and after doxorubicin treatment (data not shown). MA plot (data not shown) and heat map (data not shown) analysis shows the significant upregulation (adjusted P value <0.05) of genes associated with apoptosis, DNA damage, oxidative stress, and doxorubicin resistance, and downregulation of genes associated with cardiac function, resulting from doxorubicin treatment (FIG. 9a, b and Table 3).

TABLE 3

Top 100 differentially expressed genes after doxorubicin treatment of hiPSC-CMs

| DED | Gene ID | BME | Log2fc | 1fcSE | P-value | P-adjusted |
|---|---|---|---|---|---|---|
| To 50 upregulated genes after 1 µM doxorubicin treatment for 24 h | POU3F1 | 252.69 | 7.21 | 0.54 | 1.18E−40 | 8.25E−37 |
| | NHLH2 | 148.60 | 7.10 | 0.61 | 1.35E−31 | 3.44E−28 |
| | KCNK10 | 38.56 | 6.80 | 0.73 | 1.35E−20 | 7.51E−18 |
| | AL591893.1 | 60.17 | 6.49 | 0.69 | 6.62E−21 | 4.12E−18 |
| | GPR87 | 141.47 | 6.48 | 0.64 | 5.85E−24 | 6.07E−21 |
| | FAM196A | 316.56 | 6.36 | 0.50 | 6.86E−37 | 3.20E−33 |
| | ADCYAP1R1 | 195.94 | 6.25 | 0.58 | 5.08E−27 | 7.74E−24 |
| | HIST1H2BF | 414.10 | 6.22 | 0.60 | 2.78E−25 | 3.54E−22 |
| | PAX5 | 52.87 | 6.11 | 0.57 | 3.99E−27 | 6.57E−24 |
| | ETV7 | 70.81 | 6.04 | 0.56 | 5.25E−27 | 7.74E−24 |
| | RP1.34B20.4 | 286.31 | 5.94 | 0.67 | 6.93E−19 | 3.23E−16 |
| | RP11.1149O23.2 | 29.91 | 5.86 | 0.68 | 6.43E−18 | 2.53E−15 |
| | SLC4A11 | 476.95 | 5.81 | 0.49 | 4.85E−32 | 1.36E−28 |
| | NKX1.2 | 24.23 | 5.72 | 0.74 | 9.84E−15 | 2.31E−12 |
| | HIST1H2AI | 91.48 | 5.70 | 0.57 | 7.62E−24 | 7.623E−21 |
| | HIST1H3H | 528.08 | 5.59 | 0.46 | 1.14E−34 | 3.97E−31 |
| | GDNF | 473.93 | 5.54 | 0.55 | 1.06E−23 | 1.02E−20 |
| | RP5.884C9.2 | 22.88 | 5.53 | 0.69 | 1.35E−15 | 3.94E−13 |
| | CCDC178 | 41.12 | 5.45 | 0.57 | 1.88E−21 | 1.28E−18 |
| | GRHL3 | 110.13 | 5.45 | 0.64 | 2.04E−17 | 7.42E−15 |
| | CLCA2 | 42.64 | 5.42 | 0.70 | 1.00E−14 | 2.34E−12 |
| | CA7 | 47.81 | 5.41 | 0.68 | 1.12E−15 | 3.47E−13 |
| | RP5.1148A21.3 | 412.80 | 5.37 | 0.40 | 1.03E−40 | 8.25E−37 |
| | RP4.794I6.4 | 144.86 | 5.33 | 0.42 | 2.59E−37 | 1.45E−33 |
| | CRTAC1 | 1959.43 | 5.32 | 0.59 | 2.67E−19 | 1.29E−16 |
| | FOXD3 | 12.75 | 5.31 | 0.79 | 1.89E−11 | 2.21E−09 |
| | HIST1H2AG | 1487.63 | 5.29 | 0.45 | 2.78E−32 | 8.63E−29 |
| | HIST1H4B | 23.96 | 5.29 | 0.79 | 1.68E−11 | 1.99E−09 |
| | TNFRSF10A | 768.57 | 5.25 | 0.42 | 1.99E−36 | 7.95E−33 |
| | AC009014.3 | 42.01 | 5.25 | 0.58 | 1.71E−19 | 8.56E−17 |
| | RP3.326I13.1 | 56.26 | 5.19 | 0.73 | 1.11E−12 | 1.76E−10 |
| | TMEM158 | 309.49 | 5.19 | 0.55 | 5.00E−21 | 3.25E−18 |
| | IGFL3 | 74.04 | 5.18 | 0.73 | 1.44E−12 | 2.24E−10 |
| | HIST1H3J | 65.55 | 5.16 | 0.85 | 1.24E−09 | 8.71E−08 |
| | CSTA | 57.41 | 5.15 | 0.74 | 3.49E−12 | 5.11E−10 |
| | HIST1H3A | 44.12 | 5.14 | 0.75 | 6.70E−12 | 8.89E−10 |
| | NOTO | 13.26 | 5.13 | 0.82 | 3.81E−10 | 3.06E−08 |
| | RP11.712B9.2 | 403.74 | 5.10 | 0.56 | 4.51E−20 | 2.34E−17 |
| | NPBWR1 | 22.77 | 5.06 | 0.76 | 3.42E−11 | 3.69E−09 |
| | CHI3L2 | 21.74 | 5.04 | 0.63 | 1.71E−15 | 4.89E−13 |
| | RP11.529G21.2 | 14.24 | 5.03 | 0.76 | 4.82E−11 | 5.05E−09 |
| | TMEM229B | 194.36 | 4.99 | 0.53 | 9.36E−21 | 5.68E−18 |
| | CMB9.22P13.2 | 21.41 | 4.99 | 0.80 | 4.40E−10 | 3.51E−08 |
| | CCDC60 | 28.51 | 4.98 | 0.70 | 8.45E−13 | 1.39E−10 |

TABLE 3-continued

Top 100 differentially expressed genes after doxorubicin treatment of hiPSC-CMs

| DED | Gene ID | BME | Log2fc | lfcSE | P-value | P-adjusted |
|---|---|---|---|---|---|---|
| | FABP5P3 | 30.12 | 4.97 | 0.77 | 1.23E-10 | 1.15E-08 |
| | INSM1 | 61.05 | 4.97 | 0.86 | 7.53E-09 | 3.95E-07 |
| | LINC01164 | 102.24 | 4.96 | 0.67 | 1.92E-13 | 3.54E-11 |
| | HIST1H2BG | 1321.85 | 4.94 | 0.45 | 5.88E-28 | 1.03E-24 |
| | EN2 | 229.27 | 4.93 | 0.81 | 1.36E-09 | 9.47E-08 |
| | TFAP2C | 27.47 | 4.93 | 0.81 | 1.13E-09 | 7.95E-08 |
| To 50 downregulated genes after 1 µM doxorubicin treatment for 24 h | DAND5 | 13.75 | -4.17 | 0.65 | 1.69E-10 | 1.54E-08 |
| | LRRC14B | 146.44 | -4.13 | 0.50 | 2.61E-16 | 8.79E-14 |
| | RP11.108M9.3 | 9.18 | -4.12 | 0.79 | 2.01E-07 | 6.55E-06 |
| | CTD.2083E4.7 | 71.79 | -3.85 | 0.56 | 6.32E-12 | 8.50E-10 |
| | RP5.1139B12.4 | 16.02 | -3.80 | 0.62 | 1.01E-09 | 7.24E-08 |
| | MIR145 | 4.42 | -3.74 | 0.78 | 1.93E-06 | 4.55E-05 |
| | RP11.19O2.1 | 15.10 | -3.69 | 0.69 | 8.83E-08 | 3.25E-06 |
| | CAV3 | 32.25 | -3.53 | 0.61 | 6.03E-09 | 3.26E-07 |
| | LINC01489 | 4.53 | -3.45 | 0.76 | 5.93E-06 | 0.00011719 |
| | DOK7 | 480.04 | -3.42 | 0.50 | 1.01E-11 | 1.28E-09 |
| | ZNF385C.1 | 29.83 | -3.34 | 0.50 | 2.77E-11 | 3.06E-09 |
| | SEC14L5 | 842.50 | -3.33 | 0.61 | 5.09E-08 | 2.01E-06 |
| | LINC01224 | 43.46 | -3.31 | 0.51 | 1.04E-10 | 9.99E-09 |
| | DIRAS2 | 18.34 | -3.30 | 0.69 | 2.06E-06 | 4.83E-05 |
| | CENPI | 73.00 | -3.23 | 0.45 | 4.39E-13 | 7.68E-11 |
| | PSRC1 | 109.26 | -3.19 | 0.46 | 3.58E-12 | 5.22E-10 |
| | RP11.218M22.2 | 7.25 | -3.19 | 0.70 | 5.90E-06 | 0.00011686 |
| | PEG13 | 19.04 | -3.16 | 0.60 | 1.15E-07 | 4.09E-06 |
| | GCK | 80.60 | -3.14 | 0.54 | 6.28E-09 | 3.37E-07 |
| | AC010136.2 | 9.00 | -3.13 | 0.67 | 2.98E-06 | 6.54E-05 |
| | CENPE | 359.36 | -3.10 | 0.39 | 2.76E-15 | 7.50E-13 |
| | UTS2R | 12.96 | -3.09 | 0.64 | 1.53E-06 | 3.75E-05 |
| | KCNK3 | 718.90 | -3.07 | 0.47 | 7.89E-11 | 7.97E-09 |
| | LRRC10 | 2770.84 | -3.05 | 0.65 | 2.86E-06 | 6.32E-05 |
| | C11orf87 | 53.56 | -3.03 | 0.60 | 4.02E-07 | 1.20E-05 |
| | NFE2 | 10.41 | -3.03 | 0.53 | 1.08E-08 | 5.37E-07 |
| | RP1.46F2.3 | 9.17 | -3.03 | 0.68 | 7.34E-06 | 0.00013904 |
| | RPL7P3 | 55.40 | -3.03 | 0.60 | 3.83E-07 | 1.15E-05 |
| | PRSS44 | 96.44 | -3.02 | 0.53 | 1.08E-08 | 5.37E-07 |
| | HRK | 353.15 | -3.01 | 0.28 | 1.10E-26 | 1.53E-23 |
| | HPR | 4.39 | -3.01 | 0.76 | 7.23E-05 | 0.00091674 |
| | CENPA | 88.31 | -2.97 | 0.43 | 5.34E-12 | 7.36E-10 |
| | SLC5A1 | 722.94 | -2.94 | 0.63 | 2.50E-06 | 5.66E-05 |
| | TMEM72 | 54.00 | -2.93 | 0.46 | 2.09E-10 | 1.82E-08 |
| | FUT1 | 38.51 | -2.91 | 0.78 | 0.00018508 | 0.00199612 |
| | DORAS1 | 235.22 | -2.90 | 0.54 | 1.01E-07 | 3.64E-06 |
| | RP11.234B24.2 | 14.42 | -2.89 | 0.56 | 2.12E-07 | 6.89E-06 |
| | PRSS42 | 243.05 | -2.89 | 0.64 | 6.13E-06 | 0.00012031 |
| | BUB1B | 429.72 | -2.89 | 0.31 | 1.15E-20 | 6.56E-18 |
| | NEIL3 | 51.28 | -2.89 | 0.45 | 1.09E-10 | 1.04E-08 |
| | XIRP2 | 170.04 | -2.88 | 0.65 | 8.04E-06 | 0.00014946 |
| | NUF2 | 191.60 | -2.87 | 0.42 | 1.19E-11 | 1.48E-09 |
| | RP3.412A9.12 | 4.32 | -2.87 | 0.80 | 0.00034348 | 0.00327085 |
| | FBXO40 | 673.90 | -2.86 | 0.60 | 1.60E-06 | 3.90E-05 |
| | KIF18B | 171.05 | -2.86 | 0.33 | 1.50E-18 | 6.46E-16 |
| | NMUR1 | 3.99 | -2.85 | 0.75 | 0.00013997 | 0.0015898 |
| | CYP2J2 | 2212.24 | -2.82 | 0.48 | E-5.3909 | 2.97E-07 |
| | TMEM88 | 304.50 | -2.81 | 0.47 | 2.53E-09 | 1.61E-07 |
| | FBXL22 | 216.00 | -2.80 | 0.44 | 1.88E-10 | 1.68E-08 |
| | LINC00908 | 6.15 | -2.79 | 0.76 | 0.0002461 | 0.00252021 |
| | TGFB1I1 | 1746.85 | -2.77 | 0.48 | 8.78E-09 | 4.48E-07 |

Figure 3:
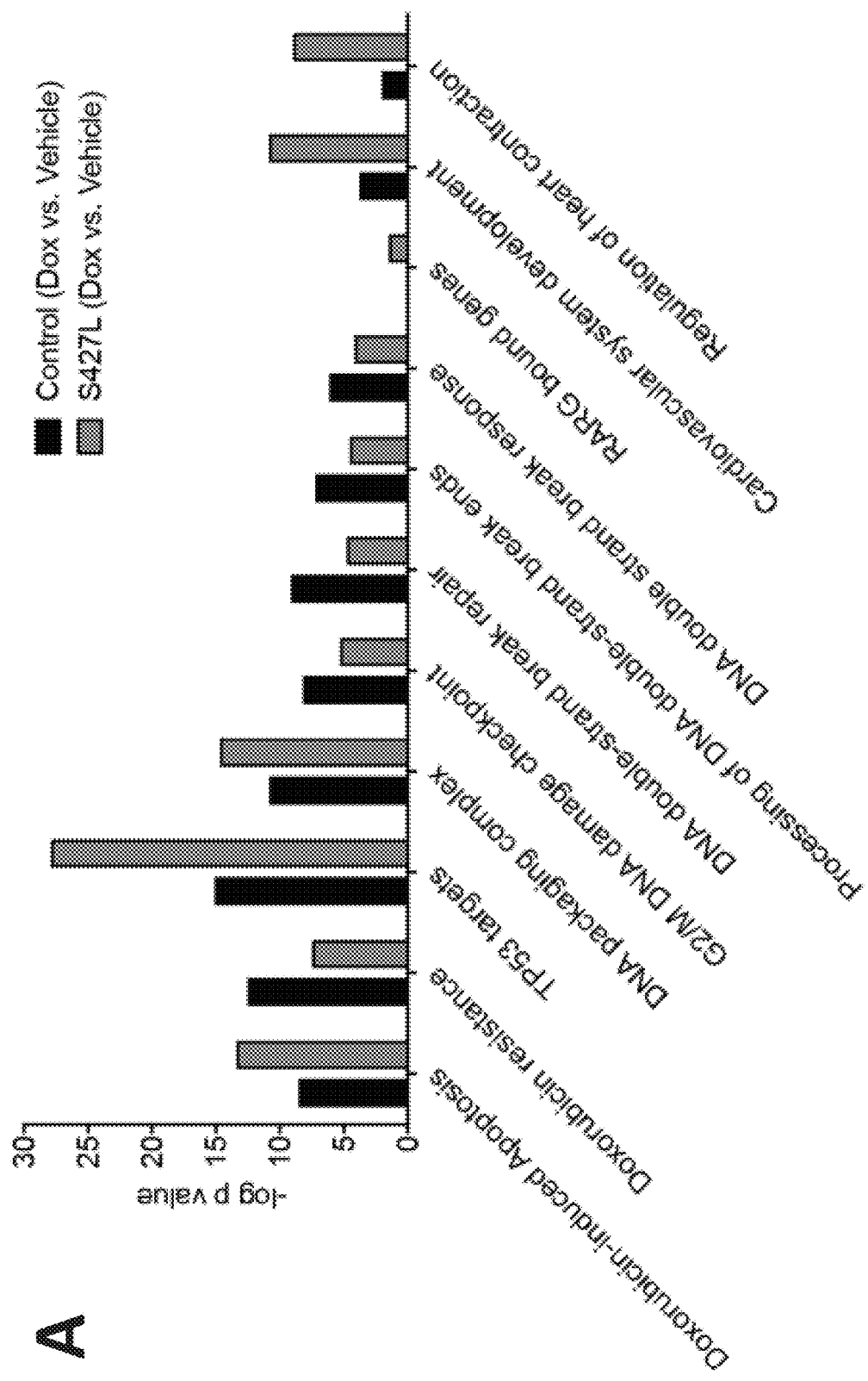
FIG. 3. S427L-dependent transcriptome changes after doxorubicin treatment of patient-derived hiPSC-CMs. Differential regulation of genes and pathways in Control and S427L hiPSC lines after treatment with 1 μM doxorubicin for 24 h. Data were obtained using hiPSC-CMs from three patients per group, one cell line per patient (n=3); 12 RNA-seq samples in total. (a) Pathway enrichment analysis of most significant transcriptome changes, showing S427L-dependent differential response. (b) Real-time PCR confirming the effect of the S427L SNP on the expression of RARG and selected genes involved in the TOP2B pathway after doxorubicin treatment of hiPSC-CMs. n=3 per group. Expression was normalized to ACTB. (c) Western blot showing S427L-dependent upregulation of RARG and TOP2B, both at the basal level and after doxorubicin treatment in hiPSC-CMs. (d) MSD analysis demonstrating significant upregulation of ERK expression in S427L hiPSC-CMs, compared with the Control. n=4 per group. Throughout, data are represented as mean±s.e.m. *$P<0.05$; $P<0.005$; *$P<0.0001$; n.s., not significant; by unpaired two-tailed Student's t-test (b) or ANOVA (d).
Figure 3:
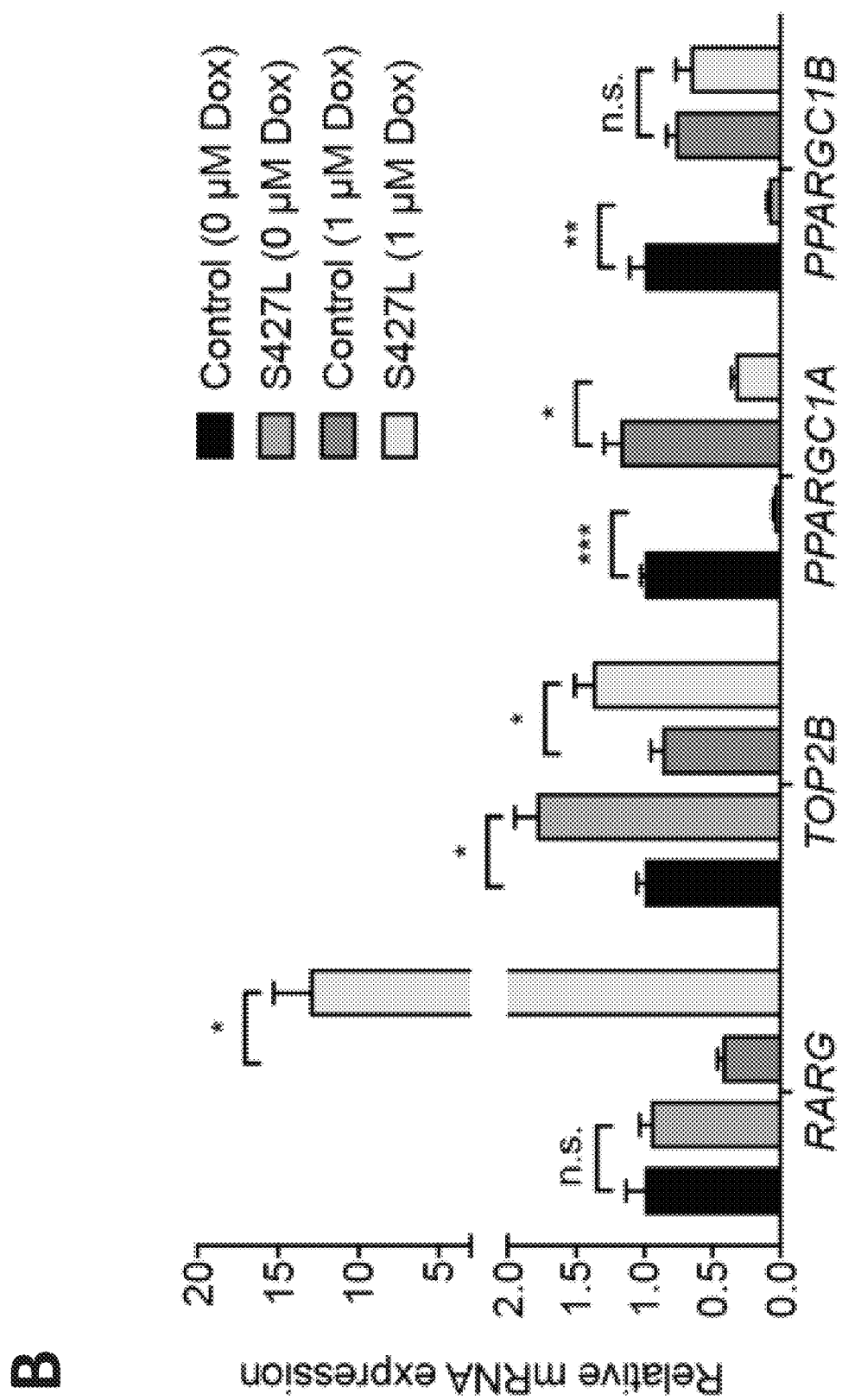
Figure 3:
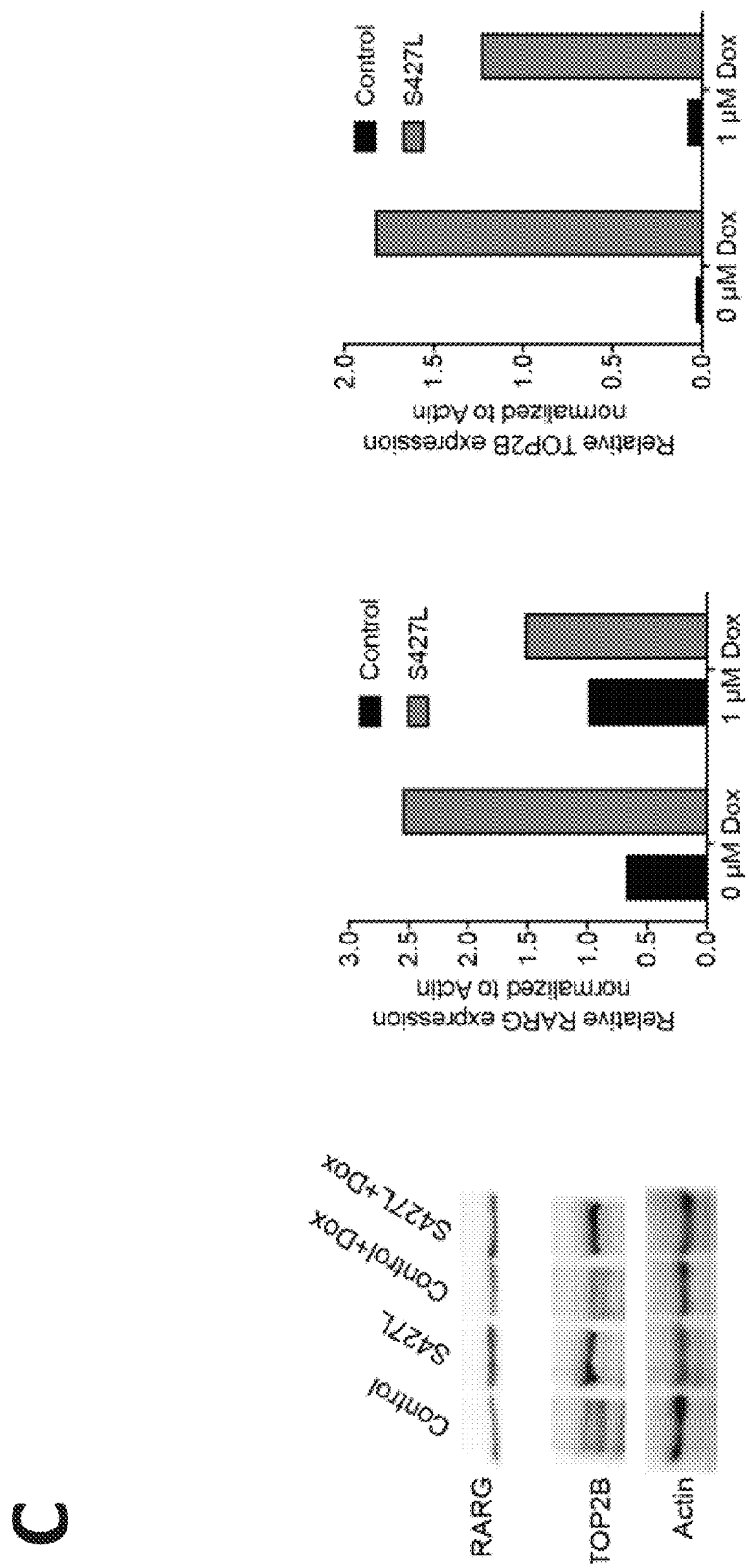
Figure 3:
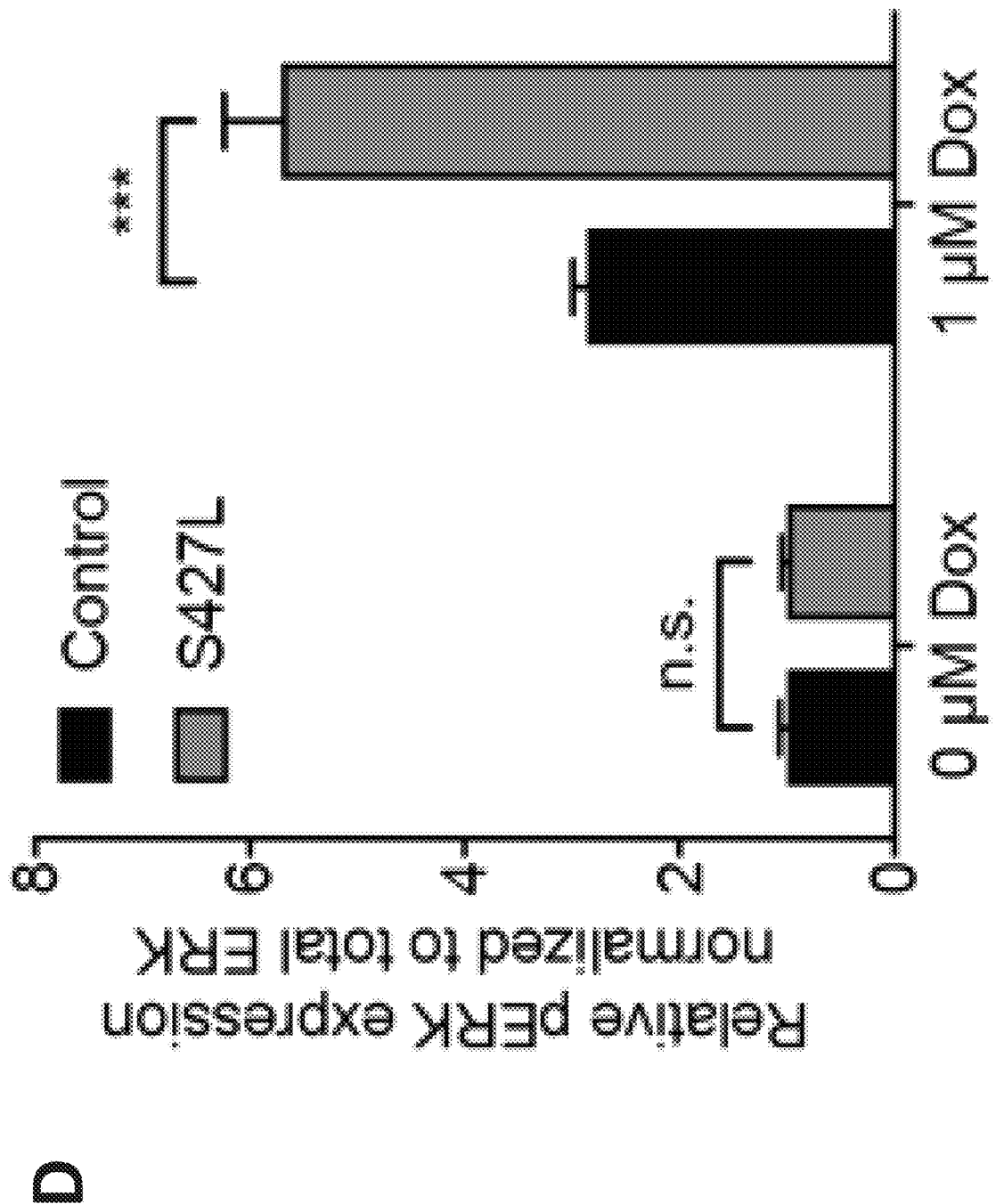

Of particular note, S427L hiPSC-CMs had significantly higher baseline expression of CAV3, a gene that is required for doxorubicin-induced apoptosis, through activation of caspase 3 (Volonte et al., 2008). Pathway enrichment analysis revealed no significant difference between S427L and control hiPSC-CMs at the basal level, before doxorubicin treatment (FIG. 9a). After treatment with doxorubicin, S427L hiPSC-CMs showed significantly more activation of doxorubicin-induced apoptosis, TP53 targets, and oxidative phosphorylation than did control cells. In contrast, doxorubicin resistance and DNA repair were more significantly activated in control cells than in S427L cells (FIG. 3a and FIG. 9a). This finding is consistent with our observation that S427L hiPSC-CMs exhibit greater sarcomeric disarray, apoptosis, ROS production, and DNA damage than control cells, upon doxorubicin treatment. Furthermore, we observed significant upregulation of RARG in S427L hiPSC-CMs compared to control cells (FIGS. 3b and c), suggesting a compensatory mechanism for the loss of function of RARG in these cells.

Figure 4:
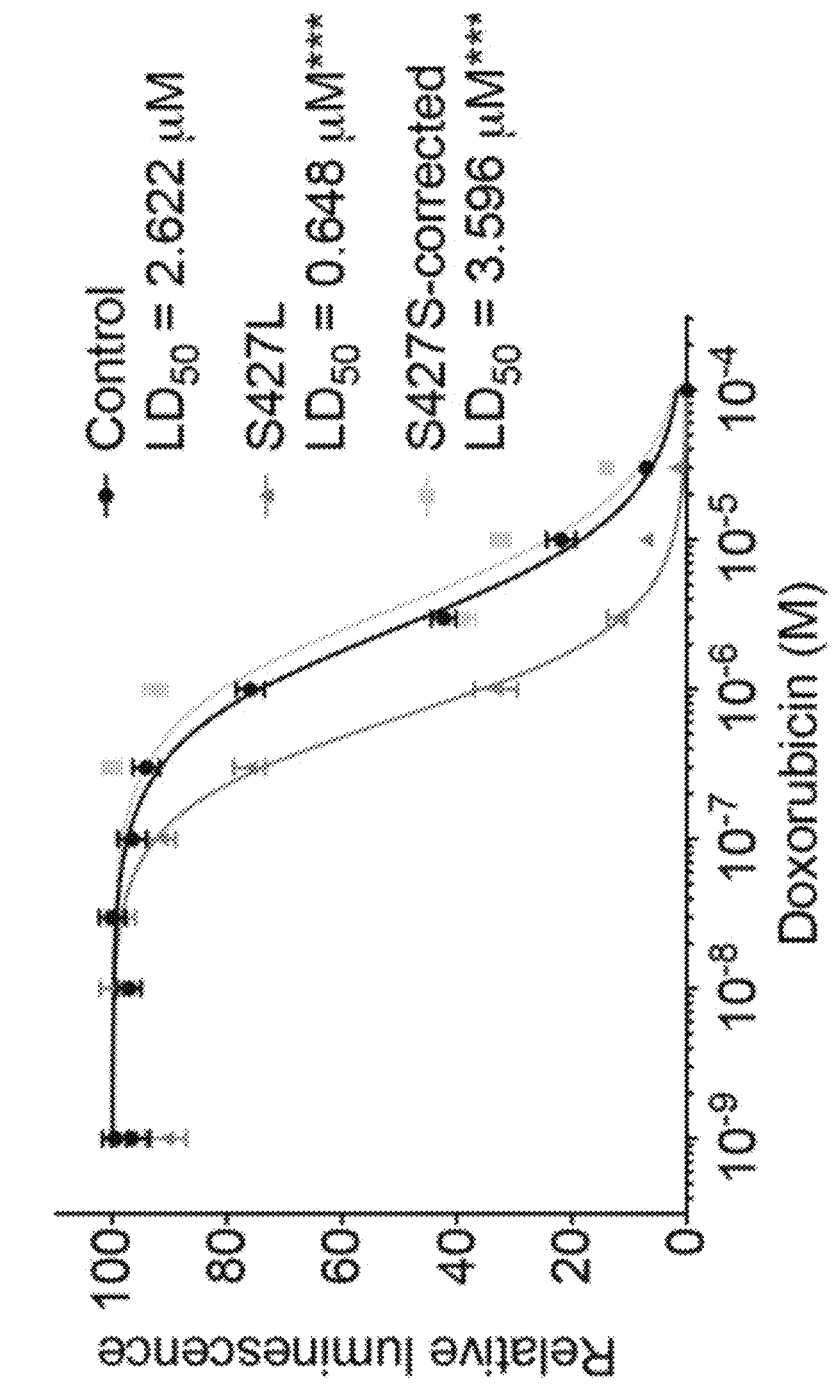
FIG. 4. Correction of the RARG variant rescues hypersensitivity to doxorubicin-induced cardiotoxicity. Comparison of hiPSC-CMs from three control patients to patient harboring the rs2229774 variant in RARG (S427L-2) and the isogenic hiPSC-CMs with CRISPR/Cas9-mediated RARG SNP correction (S427S-corrected), after 24 h or 72 h of doxorubicin treatment. (a) Effect of doxorubicin (72 h) on hiPSC-CM viability. Control: n=22, S427L: n=28, S427S-corrected: n=37. (b) Effect of doxorubicin (24 h) on caspase 3 and 7 activity in hiPSC-CMs. Control: n=32, S427L: n=17, S427S-corrected: n=39. (c) Representative images of JC-10 staining for assessing mitochondrial membrane potential in hiPSC-CMs, after treatment with doxorubicin at the indicated concentrations for 24 h. Scale bars, 100 μm. (d) Quantification of γH2AX staining in hiPSC-CMs by flow cytometry. Control: n=6, S427L: n=10, S427S-corrected: n=5. Throughout, data are represented as mean±s.e.m. *P<0.05; ***P<0.0001; n.s., not significant; by F-test (a and b) or unpaired two-tailed Student's t-test (d).
Figure 4:
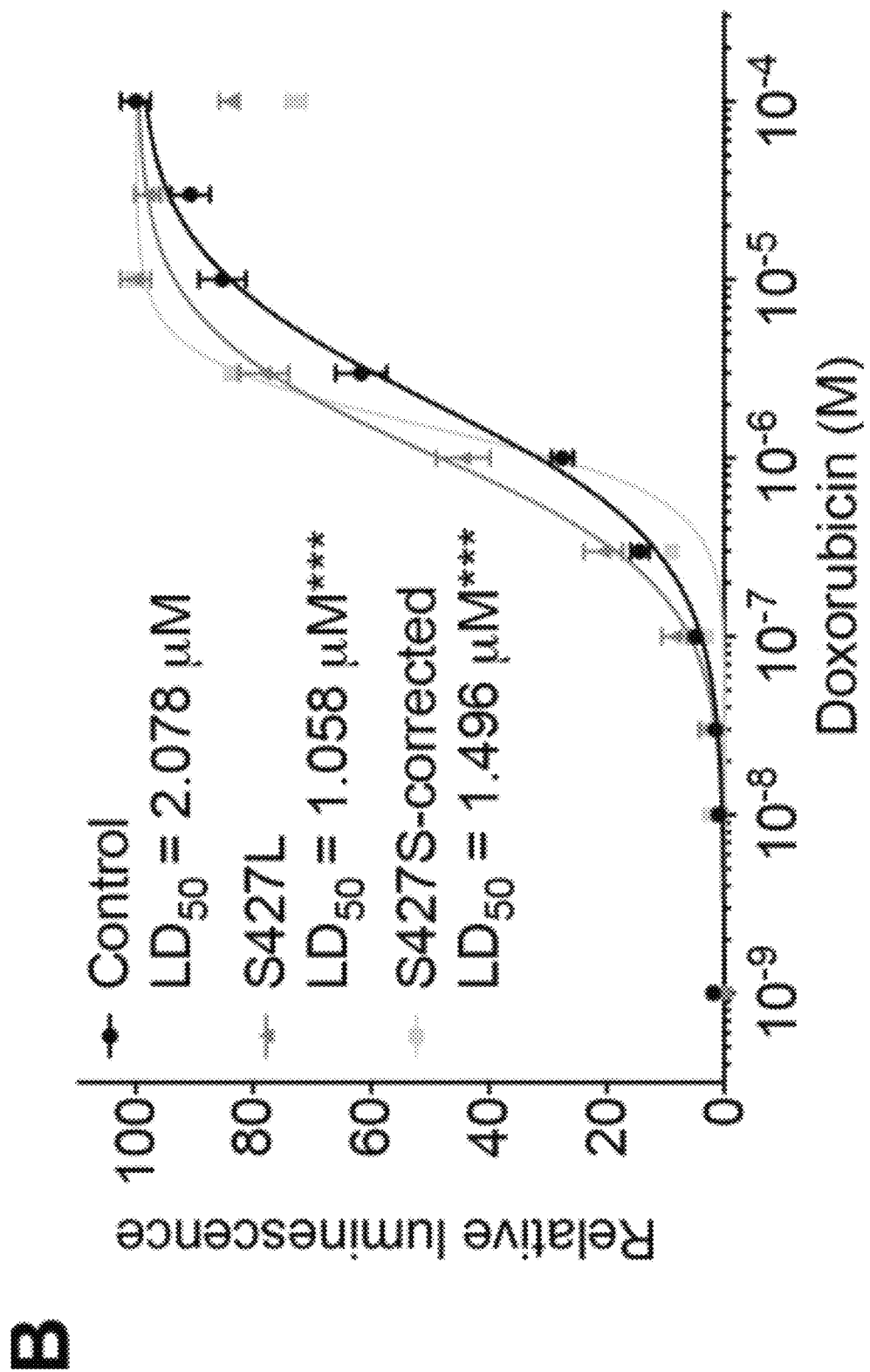
Figure 4:
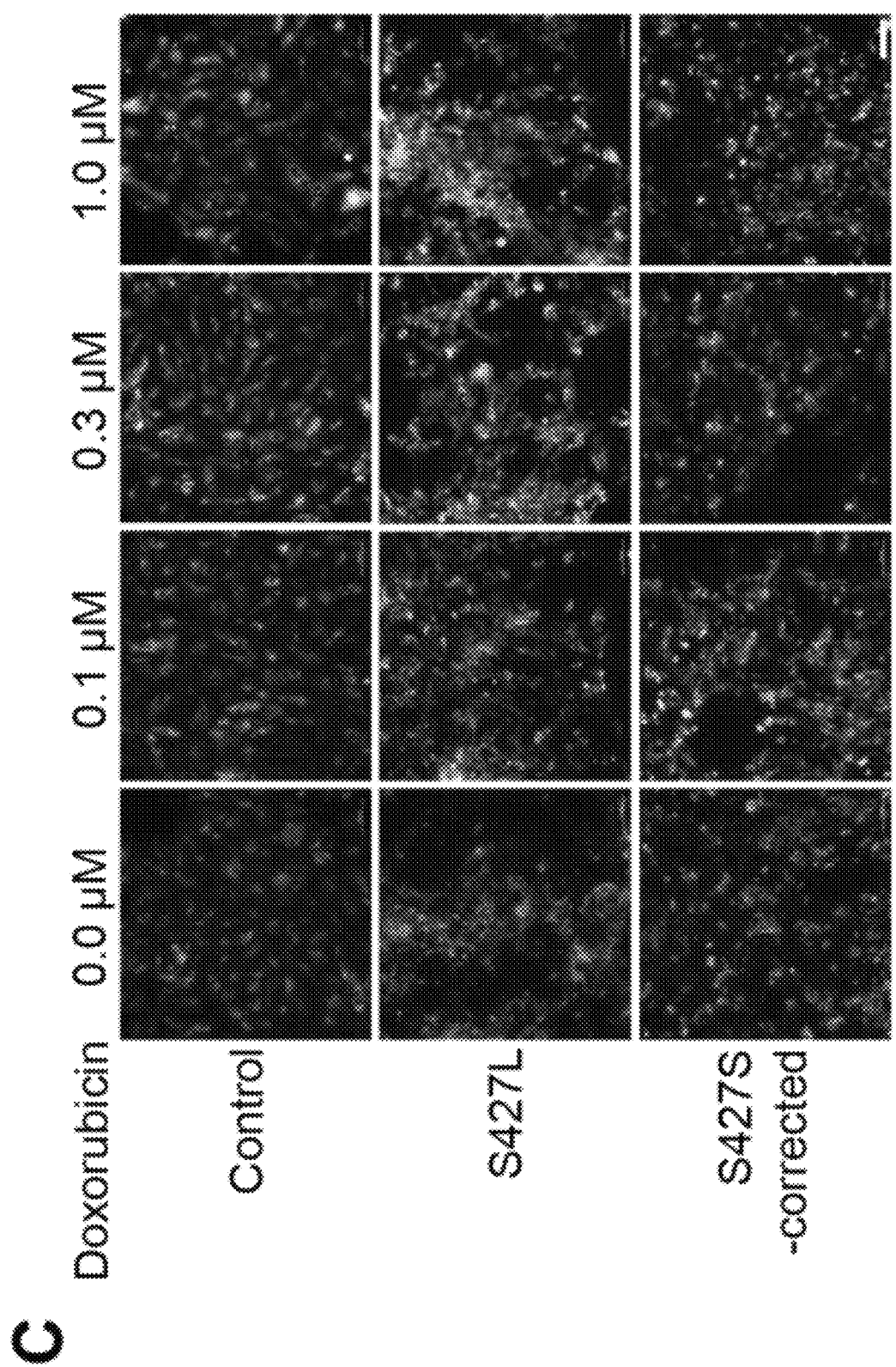
Figure 4:
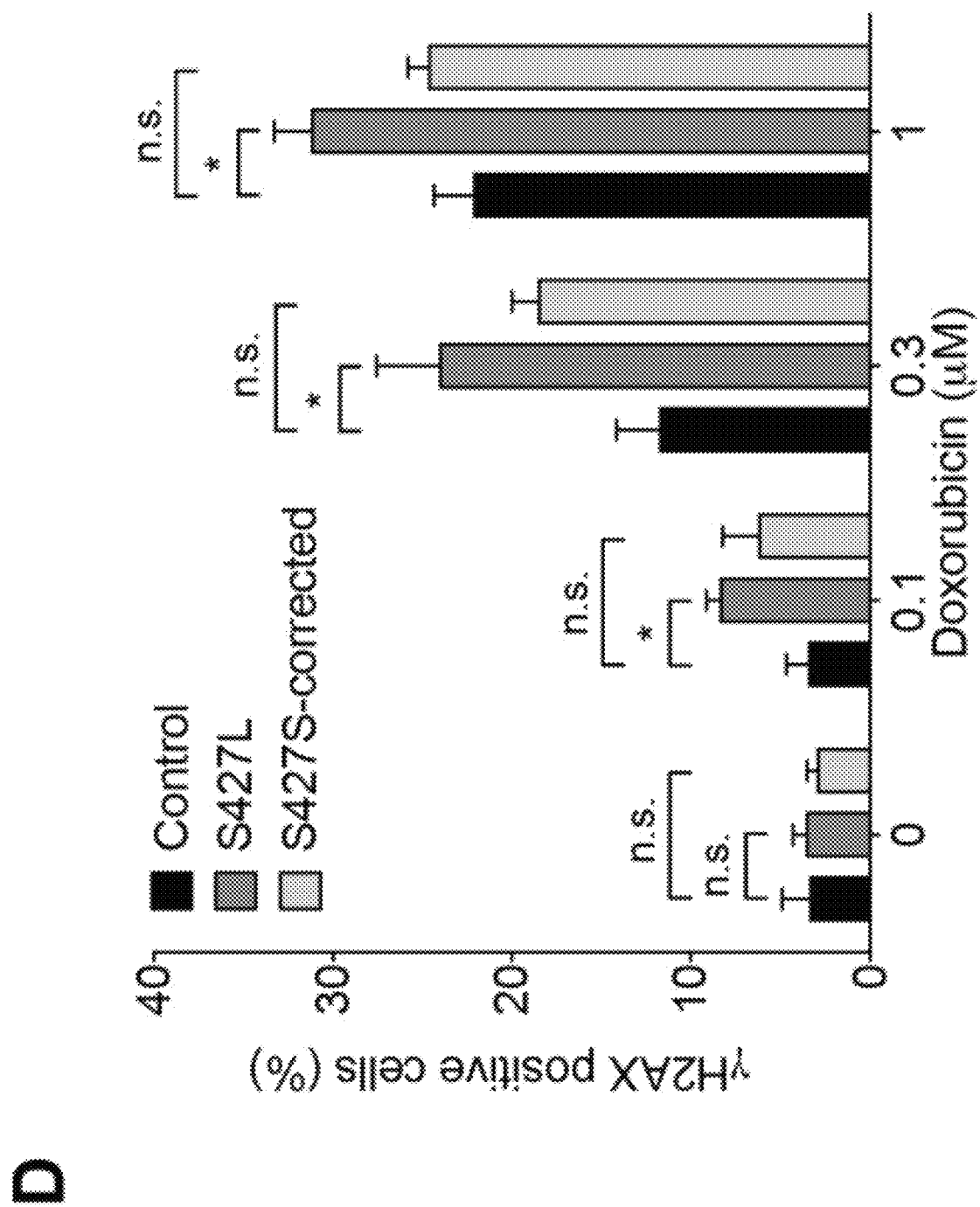
Figure 9:
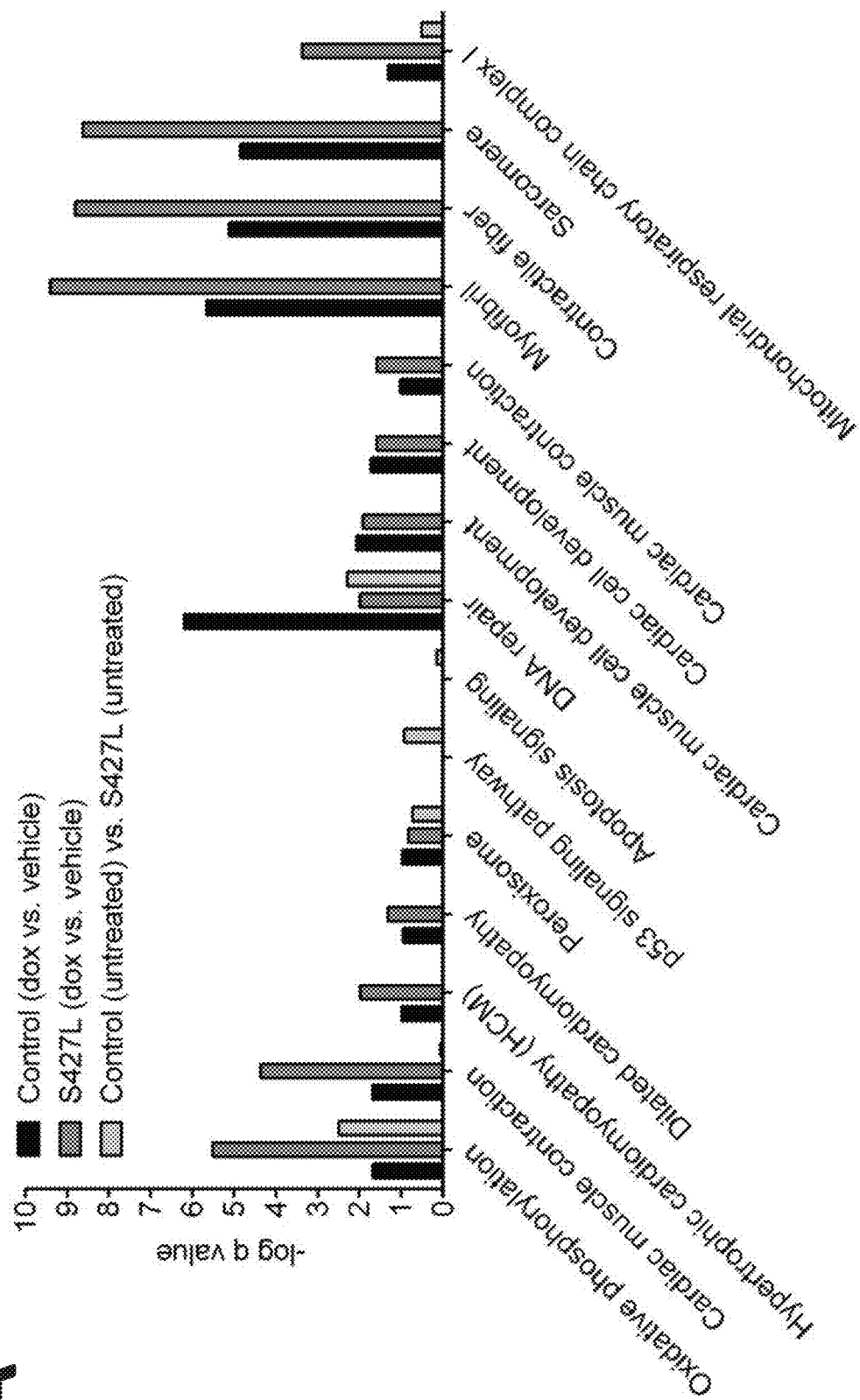
FIG. 9. Transcriptome changes after doxorubicin treatment of patient-derived hiPSC-CMs. Differential regulation of genes and pathways in Control and S427L hiPSC lines after treatment with 1 μM doxorubicin for 24 h. Data were obtained using hiPSC-CMs from three patients per group, one cell line per patient (n=3); 12 RNA-seq samples in total. (a) KEGG and GO pathway enrichment analysis of transcriptome changes (fold change>1.5), showing S427L-dependent differential response. (b) and (c) Expression of apoptosis, DNA damage, oxidative stress, doxorubicin resistance and cardiac function related genes, showing doxorubicin-induced changes. Data are represented as mean±s.e.m. *P<0.05; P<0.005; *P<0.0001; n.s., not significant; by unpaired two-tailed Student's t-test.
Figure 9:
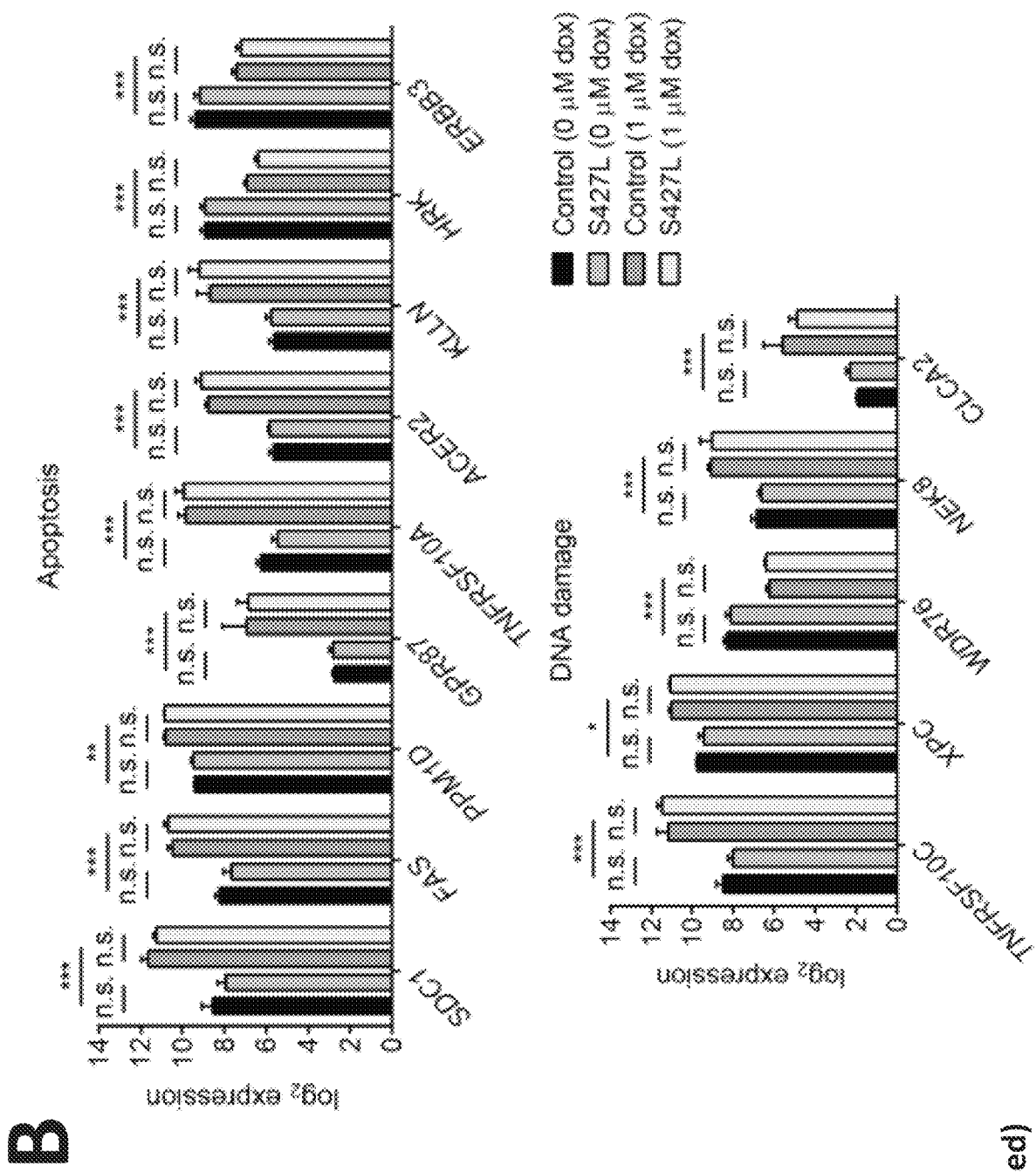
Figure 9:
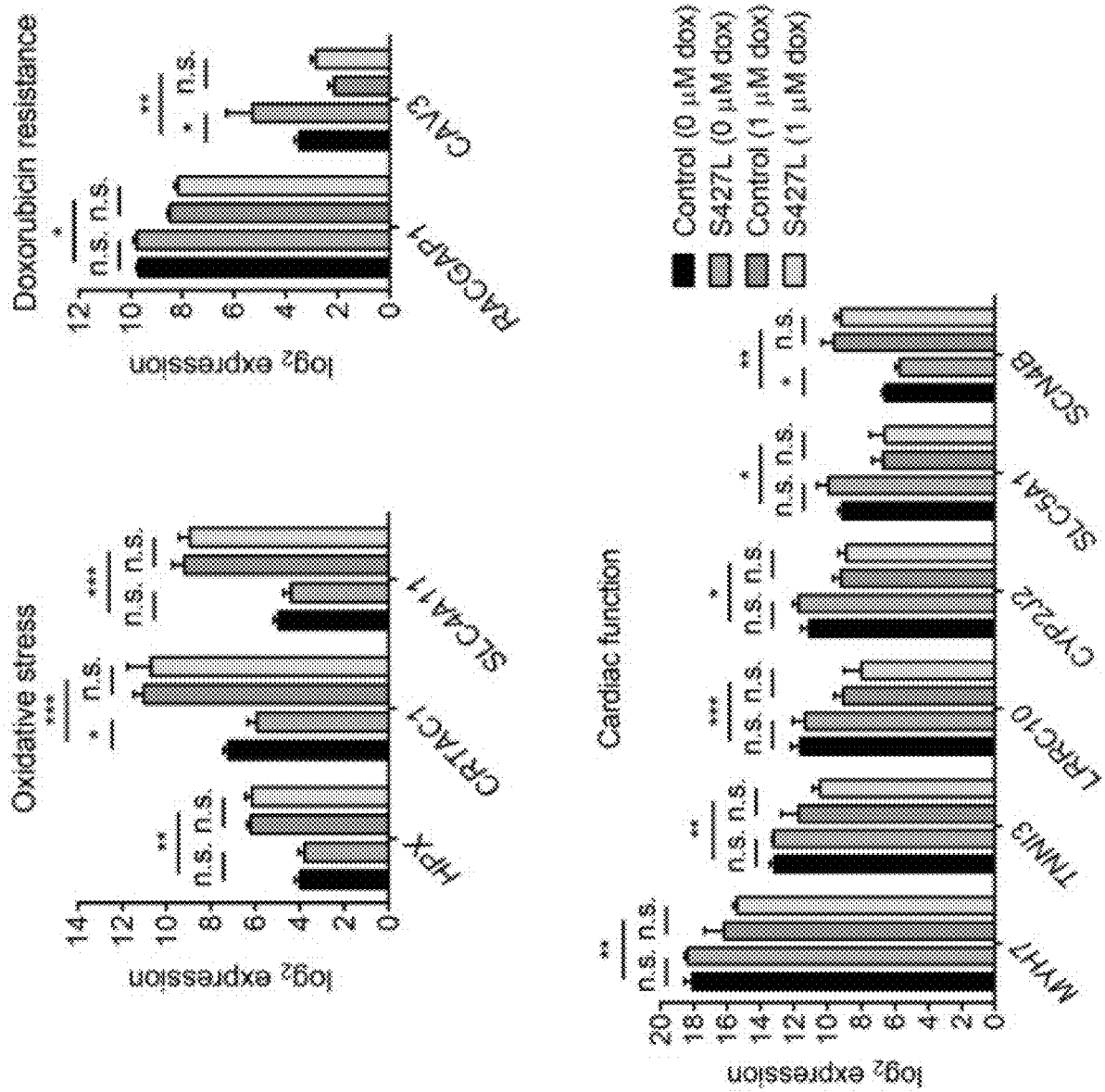

We next sought to analyze how RARG variants might influence known mechanisms of DIC. In the mouse model, knockout of Top2b attenuates DIC (Zhang et al., 2012). We re-analyzed existing data and found that RARG binds a retinoic acid response element (RARE) 907 bp downstream of the TOP2B transcription start site (Delacroix et al., 2010;

Lalevee et al., 2011). To assess if the RARG variant may function via a TOP2B-related mechanism, we assessed TOP2B expression and found it to be significantly higher in S427L hiPSC-CMs than in control cells, both at the basal level and after doxorubicin treatment (FIGS. 3b and c). Genes crucial for mitochondrial biogenesis downstream of TOP2B, such as PPARGC1A and PPARGC1B, encoding the transcriptional coactivators PGC-1α and PGC-1β, were also significantly downregulated in S427L hiPSC-CMs compared to control cells (FIG. 3b). The functional effect of these gene expression changes on mitochondrial membrane potential was validated using a lipophilic fluorochrome JC-10, where the red/green fluorescence ratio was markedly reduced in S427L hiPSC-CMs but not in control cells, at lower doxorubicin concentrations (FIG. 4c). Our data strongly suggest that RARG directly represses TOP2B expression and that the rs2229774 SNP disrupts this regulation, leading to increased TOP2B-mediated DNA damage and decreased mitochondrial biogenesis/function, upon doxorubicin treatment, connecting RARG to a previously established mechanism of DIC (Zhang et al., 2012). Of particular note, RARG overexpression was as potent as TOP2B knockout for reducing DIC in hiPSC-CMs (FIG. 8d-g), suggesting that RARG agonism might be a suitable drug-based cardioprotective methodology to reduce TOP2B-related cardiotoxicity.

utilized CRISPR/Cas9-mediated genome editing to revert the SNP in one of the S427L hiPSC lines to the major allele (FIG. 9). By comparing the SNP reverted (S427S-corrected) hiPSC-CMs with their isogenic S427L cells and control cells, we found that the SNP correction was able to reduce doxorubicin sensitivity to control levels at all doxorubicin concentrations tested, as assessed by cell viability (FIG. 4a), apoptosis (FIG. 4b), mitochondrial membrane potential (FIG. 4c), DNA damage (FIG. 4d) and ROS production (FIG. 8a). These results demonstrate that the rs2229774 SNP alone is responsible for the increased risk of DIC.

RARG-specific agonists attenuate the cardiotoxicity of doxorubicin without impeding anticancer efficacy. Since our data indicated that loss of function of RARG caused by the rs2229774 SNP led to increased doxorubicin sensitivity, we next asked whether stimulating RARG signaling in S427L hiPSC-CMs could reduce doxorubicin sensitivity. We pre/ co-treated cells with three RARG-specific small molecule agonists (BMS961, CD437, and CD1530) or the general RAR agonist all-trans retinoic acid (ATRA) at concentrations of 0 μM, 0.3 μM, 1 μM, and 10 μM an assessed cell viability after doxorubicin treatment for 72 h over a 5-log concentration range. All of these agonists were able to improve cell viability, with CD1530 being the most effective at an optimal concentration of 1 μM, increasing $LD_{50}$ by 4 to 7-fold for RARG-WT and S427L hiPSC-CMs, respectively (FIG. 5a, FIG. 11a-g and Table 4).

TABLE 4

Effect of RARG agonists on doxorubicin-indiced carditoxicity in patient-derived hiPSC-CMs.

| Agonist | RARG-WT: $LD_{50}$ (μM) | | | | S427L-1: $LD_{50}$ (μM) | | | |
|---|---|---|---|---|---|---|---|---|
| (μM) | 0 | 0.3 | 1 | 10 | 0 | 0.3 | 1 | 10 |
| ATRA | 0.469 | 1.265*** | 1.832*** | 3.049*** | 0.600 | 0.951** | 2.111*** | 2.750*** |
| BMS961 | 0.469 | 0.712 | 1.106 | 1.885** | 0.600 | 0.985* | 1.751*** | 2.692*** |
| CD437 | 0.469 | 2.365*** | 1.783*** | 1.791*** | 0.600 | 2.772** | 1.692*** | 1.558*** |
| CD1530 | 0.469 | 1.435* | 1.687*** | 2.947*** | 0.600 | 1.520** | 4.428*** | 4.537*** |

Assessment of cell viability of RARG-WT or S427L-1 hiPSC-CMs after 72 h of doxorubicin and RARG agonists co-treatment at indicated concentrations using a CellTitre-Glo based ATP assay.
n = 6 replicates for each data point.
The value of $LD_{50}$ for each treatment are shown.
*$P < 0.05$; $P < 0.005$; *$P < 0.0001$; by F-test.

As a second potential mechanism, we were interested in the existing well-established link between ERK activation and prevention of doxorubicin-induced cardiomyocyte damage (Fryer et al., 2001; Izumi et al., 2006; Simoncikova et al., 2008; Su et al., 2006; Xiang et al., 2009; Yang et al., 2016). In addition to the canonical RARE pathways, retinoic acids are also well known to function through a non-canonical pathway by directly binding protein kinase C α (PRCKA) (Ochoa et al., 2002), resulting in phosphorylation of extracellular regulated kinase (ERK1/2 or MAPK1/3) (Canon et al., 2004), which leads to activation of cAMP response element-binding protein (CREB) (Aggarwal et al., 2006), a transcription factor known to regulate many genes involved in cardiomyocyte survival (Ichiki, 2006). We observed significant increase in phosphorylated ERK (pERK) in S427L hiPSC-CMs upon doxorubicin treatment, compared to control cells (FIG. 3d), suggesting that the effect of the RARG SNP on doxorubicin-activated ERK signaling may also play a role in DIC, a finding we further investigate below.

Figure 5:
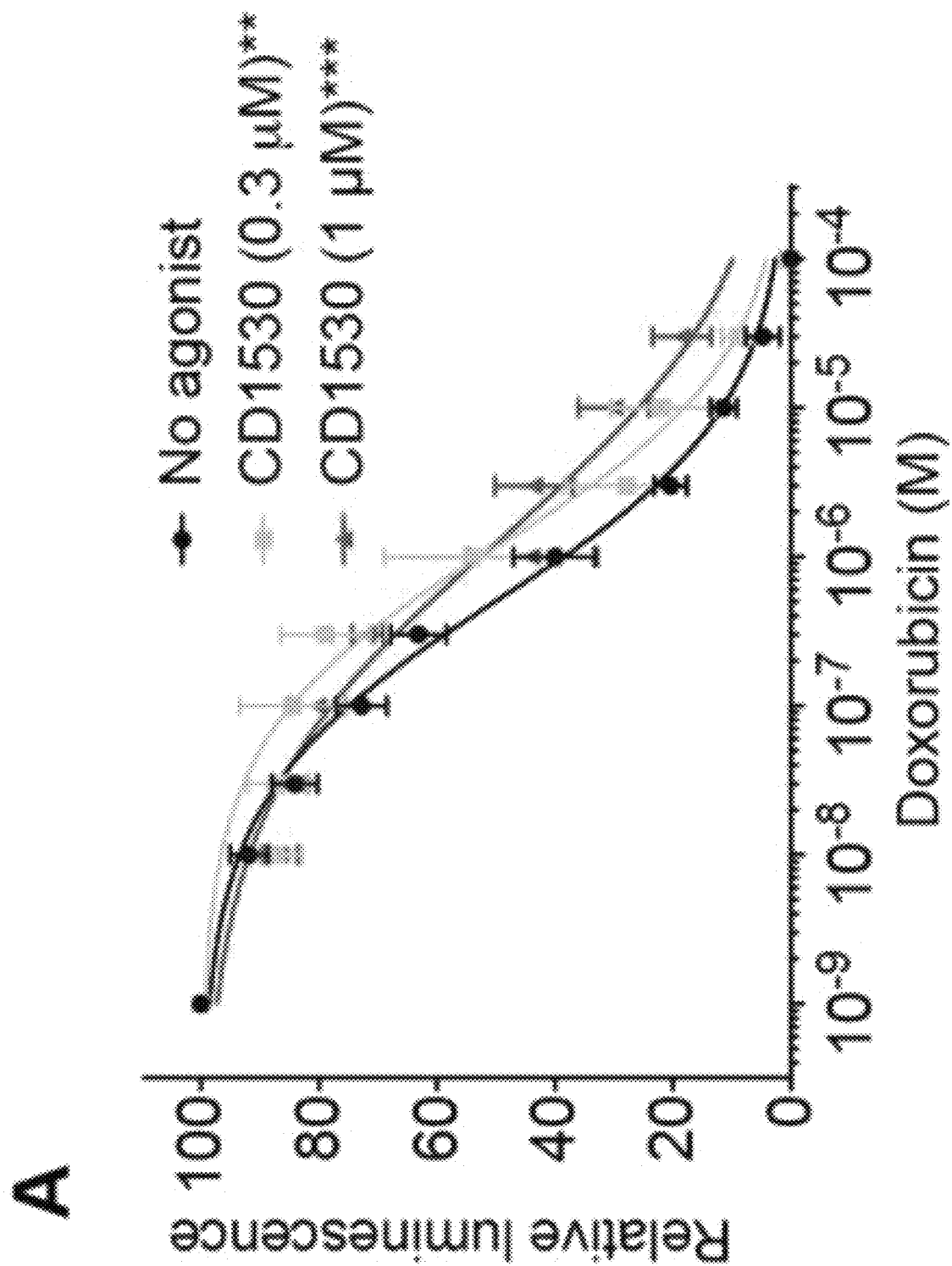
FIG. 5. RARG specific agonist protects against doxorubicin-induced cardiotoxicity. (a) Effect of RARG agonist CD1530 on the viability of S427L hiPSC-CMs after 72 h of doxorubicin treatment. n=6 replicates for each data point. (b) Effect of 1 μM CD1530 on the RARG expression and TOP2B signaling in the S427L hiPSC-CMs after 3 μM doxorubicin treatment for 24 h, as assessed by real-time PCR, normalized to 18S. n=3 replicates for each group. (c) MSD analysis showing significant upregulation of ERK expression in Control hiPSC-CMs with CD1530 treatment, in a dose dependent manner. FC: fold change is the ratio of pERK between 1 μM and 0 μM of doxorubicin treatment for 24 h. n=4 per group. (d) Effect of 1 μM CD1530 and 30 μM U0126 on the viability of Control hiPSC-CMs after 72 h of doxorubicin treatment n=6 replicates for each data point. (e) Changes in left ventricular fractional shortening (FS) at three weeks after treatment, normalized to the baseline. (f) Relative expression of TOP2B, pERK and BCL2 in the hearts of mice at three weeks after treatment as assessed by Western blot, normalized to GAPDH. (g) Assessment of cell viability of MCF7 breast cancer cell line after 72 h of doxorubicin and RARG agonists (1 μM each) co-treatment. n=2 replicates for each data point. Throughout, data are represented as mean±s.e.m. *P<0.05; P<0.005; *P<0.0001; n.s., not significant; by F-test (a and g), unpaired two-tailed Student's t-test (b) or ANOVA (c, d, e and f).
Figure 5:
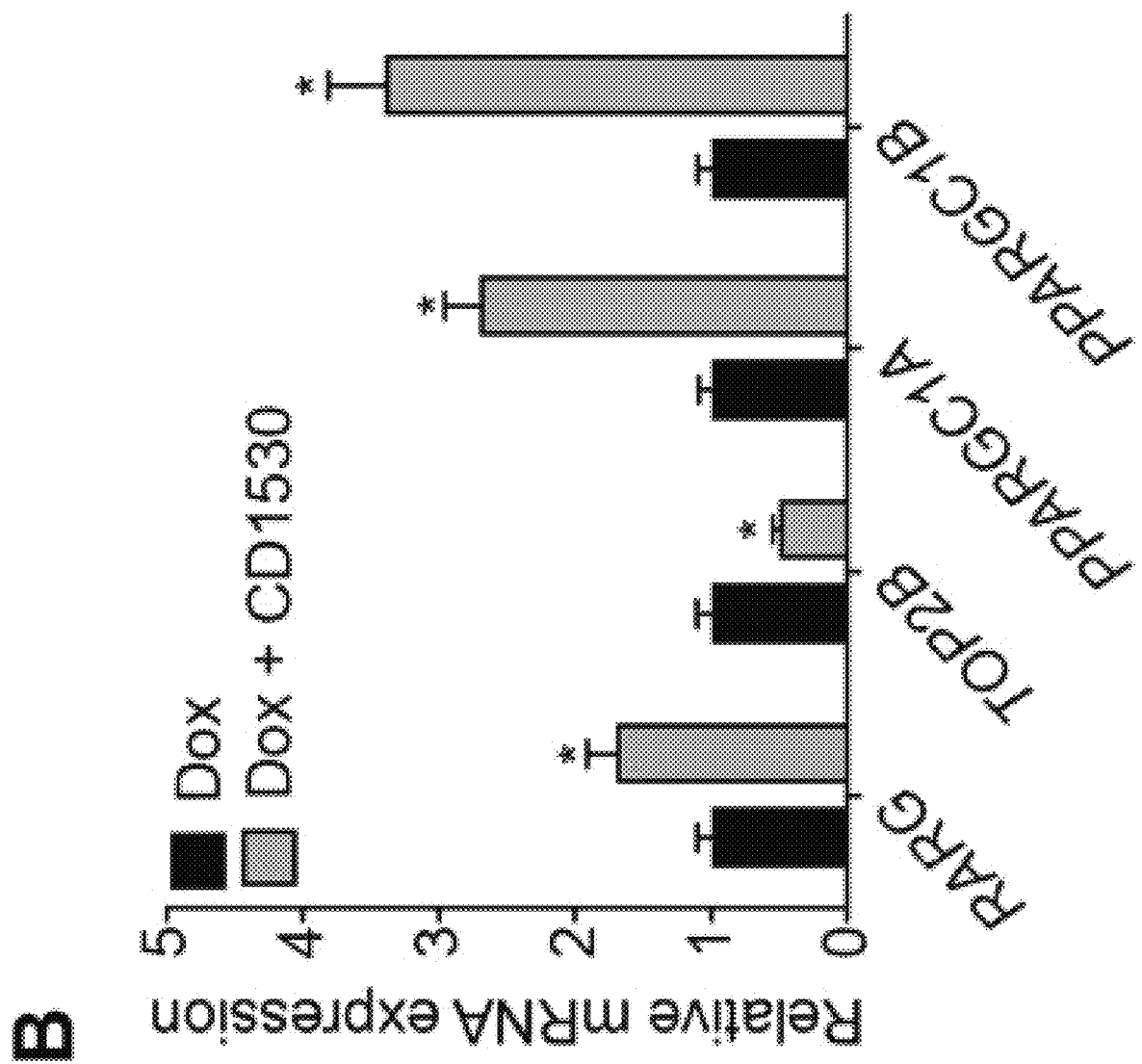
Figure 5:
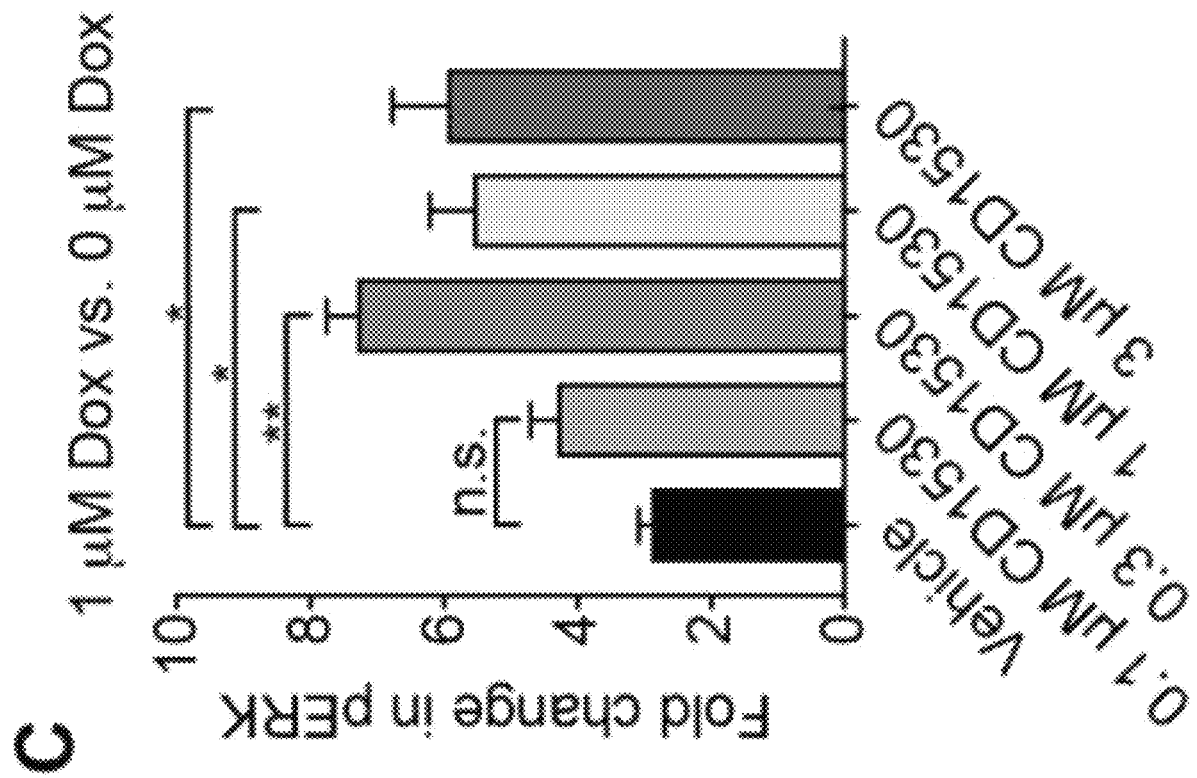
Figure 5:
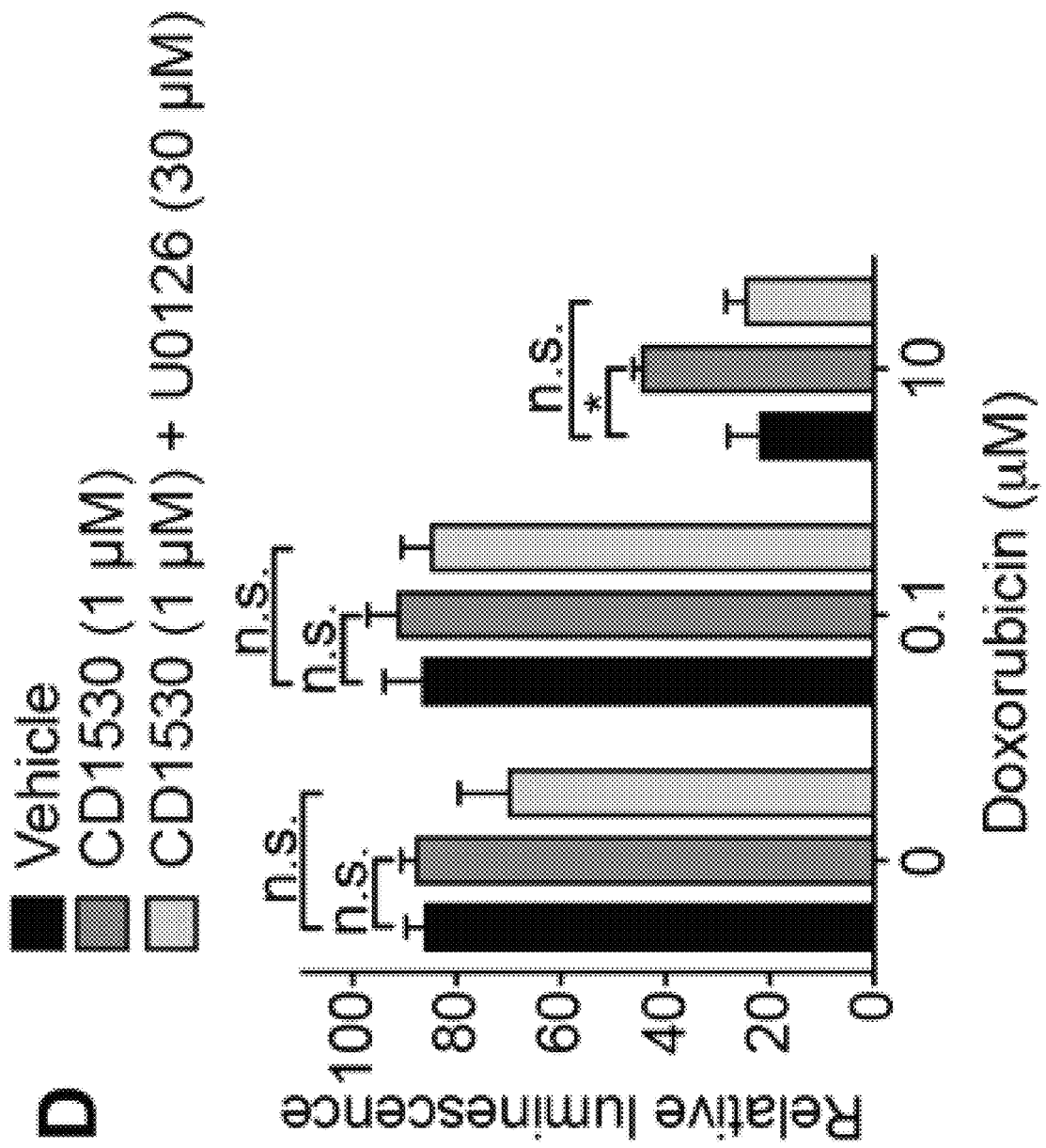
Figure 5:
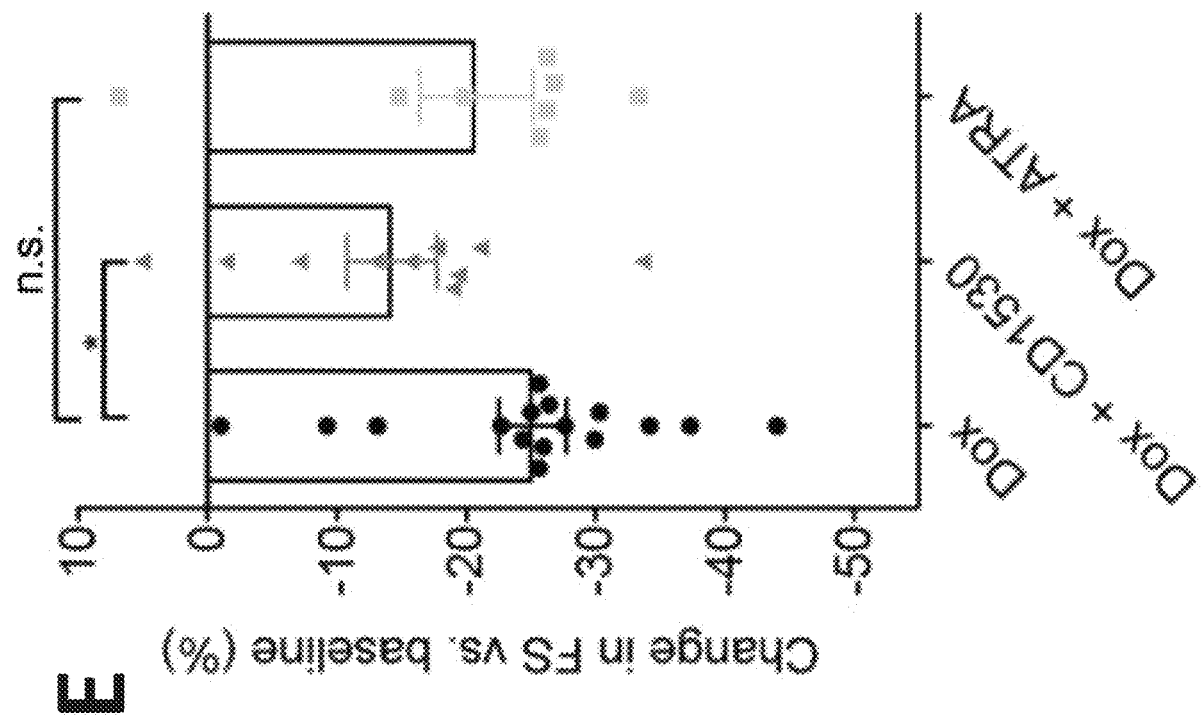
Figure 5:
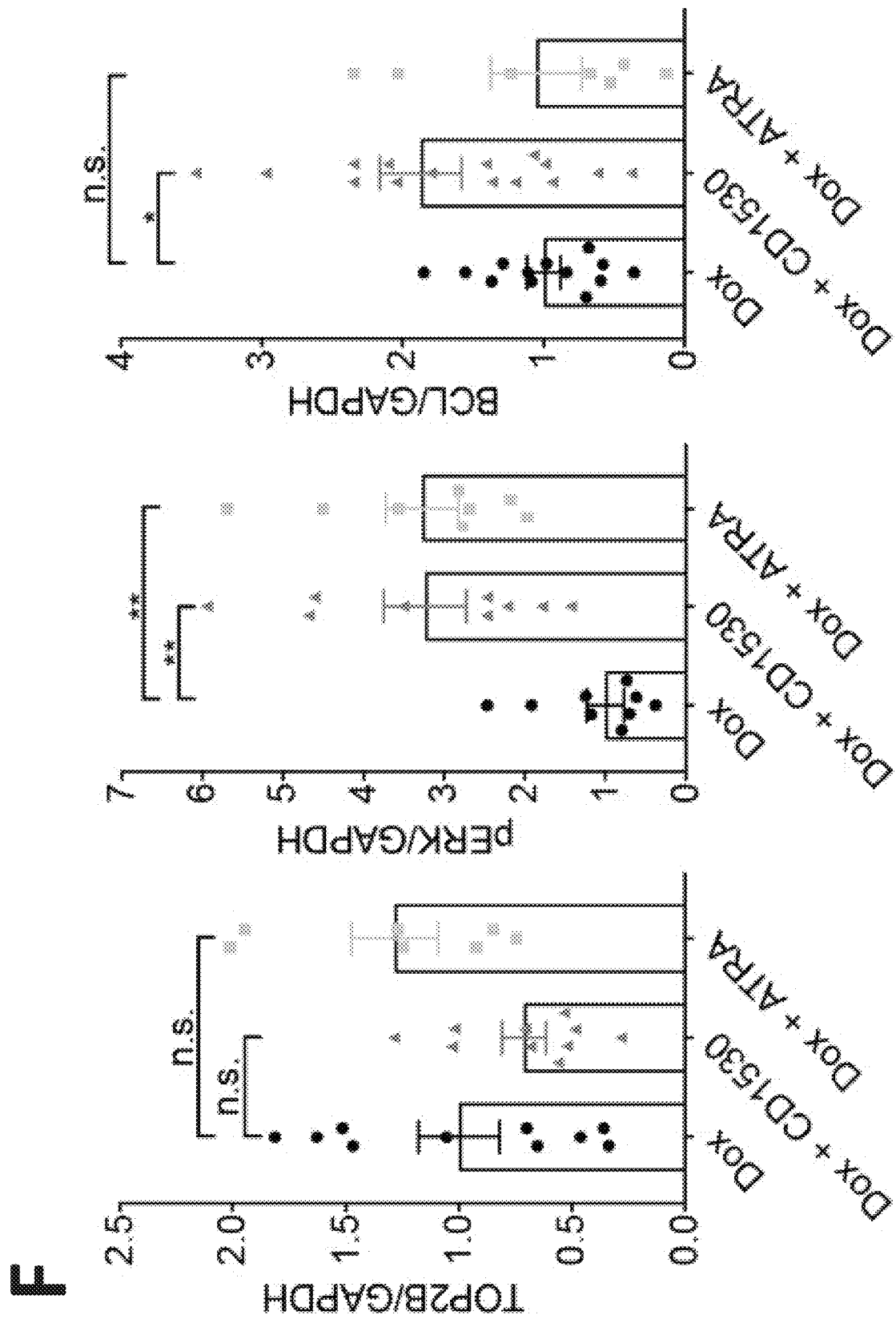
Figure 5:
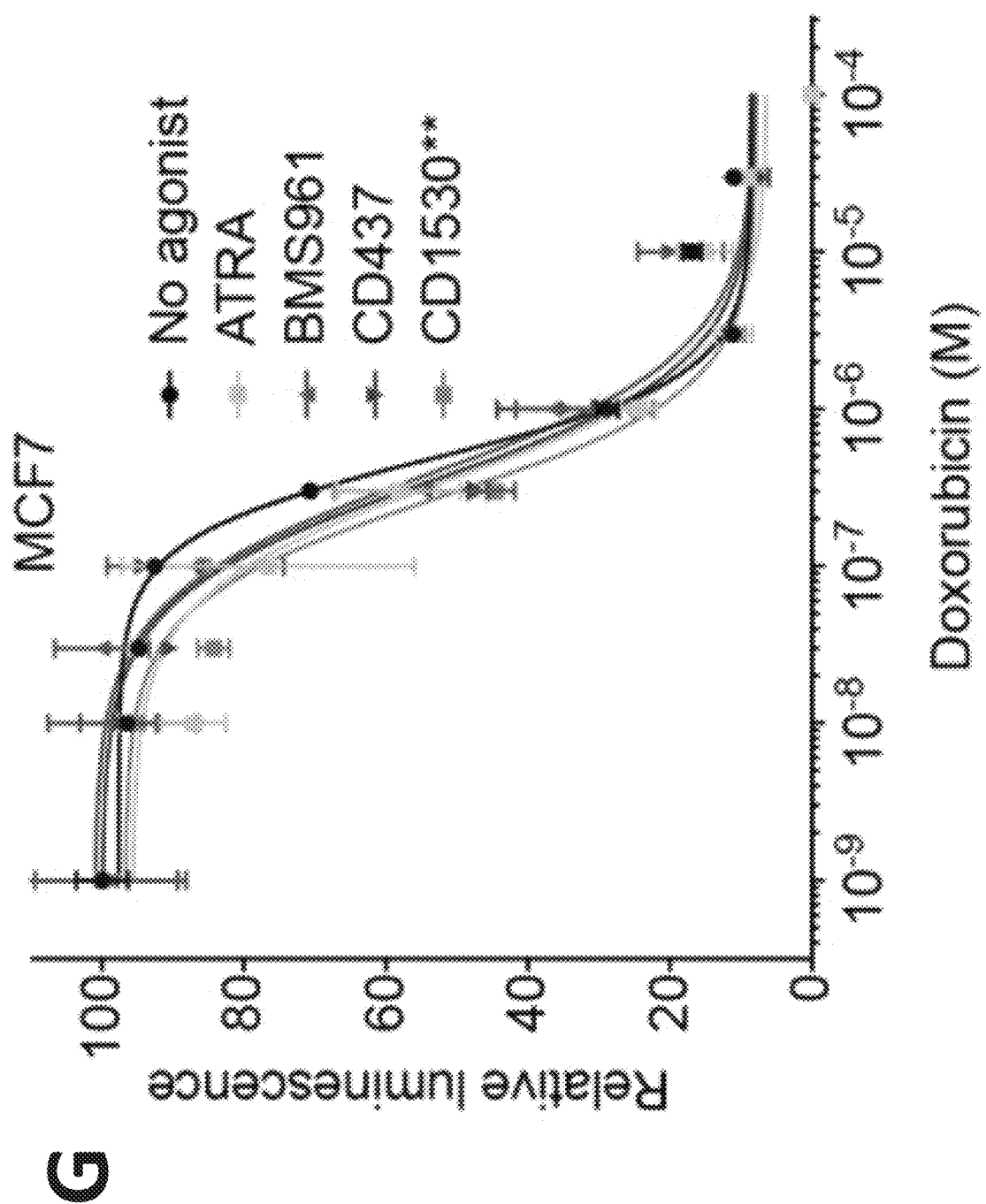

Correction of the RARG variant in hiPSC-CMs rescues hypersensitivity to DIC. To directly confirm that rs2229774 is the causative SNP for the increased risk of DIC, we These findings indicate that activation of RARG signaling could reduce doxorubicin cardiotoxicity in hiPSC-CMs both with and without the rs2229774 SNP. Furthermore, activation of RARG signaling by CD1530 in S427L hiPSC-CMs increased RARG expression, repressed TOP2B expression, and also upregulated genes involved in mitochondrial biogenesis (FIG. 5b). To further investigate the non-canonical retinoic acid pathway, we assessed pERK in hiPSC-CMs treated with doxorubicin, with or without pre/co-treatment with CD1530, and we found a significant increase in pERK in CD1530-treated cells (FIG. 5c). Furthermore, inhibition of ERK signaling using the MEK1/2 inhibitor U0126 (Yang et al., 2016) completely abolished the protective effect of CD1530 (FIG. 5d), confirming RARG agonism as a pERK-dependent cardioprotective mechanism.

To investigate whether RARG agonists could attenuate DIC in vivo, we treated mice with doxorubicin (3 mg kg$^{-1}$ intraperitoneal twice weekly for 3 weeks) plus oral CD1530, ATRA, or vehicle control. Doxorubicin treatment results in a steady decline in cardiac function, as assessed by fractional shortening. Critically, cardiac function was significantly higher at three weeks with CD1530 (P<0.05) and was marginally improved with ATRA (P=0.05), compared with vehicle treatment (Fig. f). Furthermore, we observed a significant upregulation of the pro-apoptosis protein inhibitor BCL2 and modest but non-significant downregulation of TOP2B in the murine hearts, with treatment of CD1530 but not ATRA, whereas pERK was significantly increased with both CD1530 and ATRA treatment (FIG. 5f). Lastly, to rule out the possibility that RARG agonists could diminish the effectiveness of doxorubicin against cancer cells, we studied four commonly used breast cancer cell lines and found that co-treatment with RARG agonists did not impede the anti-cancer efficacy of doxorubicin and even enhanced efficacy in two lines (FIG. 5g, FIG. 11h-j, and Table 5).

TABLE 5

RARG agonists do not impede the efficacy of doxorubicin in breast cancer cells.

| Agonist | $LD_{50}$ (μM) | | | | |
|---|---|---|---|---|---|
| (10 μM) | Vehicle | ATRA | BMS961 | CD437 | CD1530 |
| Hs 578T | 1.829 | 1.950 | 1.272 | 2.167 | 1.322 |
| MCF7 | 0.490 | 0.355 | 0.375 | 0.343 | 0.275** |
| MDA-MB-231 | 1.301 | 1.283 | 1.117 | 1.338 | 1.293 |
| MDA-MB-468 | 1.330 | 0.346*** | 0.472** | 0.561** | 0.512** |

Assessment of cell viability of four breast cancer cell lines after 72 h of doxorubicin and RARG agonists (1 μM each) co-treatment using a CellTitre-Glo based ATP assay.
n = 2 replicates for each data point.
Data are represented as mean ± s.e.m.
P < 0.005; *P < 0.0001; by F-test.

Discussion

We have demonstrated that hiPSC-CMs can recapitulate patient-specific differences in the predilection to DIC and can be utilized for the direct validation of GWAS-identified genetic variants. When coupled with CRISPR/Cas9-mediated genome editing, hiPSCs serve as a powerful new platform for pharmacogenomic evaluation of both drug efficacy and toxicity. This platform can be extended to validating other GWAS-identified SNPs, both in the field of pharmacogenomics and potentially for any disease where the phenotype can be modeled in the dish. By editing hiPSC lines derived from patients with a specific disease phenotype, we can query single SNPs as the sole experimental variable, whilst maintaining other SNPs that may influence the phenotype.

The mechanisms by which doxorubicin affects cancer cells and causes cardiotoxicity are thought to be different, providing an opportunity for the development of cardioprotective agents that do not interfere with chemotherapeutic efficacy. Cancer cells rely on topoisomerase 2a (TOP2A) to introduce double-stranded DNA breaks that release DNA torsional stress generated during rapid DNA replication. Doxorubicin inhibits the decoupling of TOP2A from DNA, preventing DNA re-ligation, resulting in DNA damage (Yang et al., 2014). Doxorubicin also directly intercalates with DNA, causing interference with RNA transcription and DNA polymerases. In the case of DIC, three major interrelated mechanisms have been proposed: (1) the production of ROS (Berlin and Haseltine, 1981) via redox cycling, using mitochondrial NAD(P)H oxidoreductases (Minotti et al., 2004), and complexing of doxorubicin with iron in mitochondria (Ichikawa et al., 2014), causing mitochondrial lipid peroxidation, mitochondrial permeability transition pore (MPTP) opening, and activation of programmed cell death (Singal and Iliskovic, 1998); (2) doxorubicin-TOP2B-DNA interaction, similar to that seen with TOP2A (Zhang et al., 2012). Like TOP2A, TOP2B functions to release DNA torsional stress, although primarily during transcription; and (3) calcium dysregulation resulting in pumping $Ca^{2+}$ out of the sarcoplasmic reticulum, increasing intracellular calcium levels, leading to sarcomeric and myofibrillar disarray (Fajardo et al., 2011; Lim et al., 2004).

In our data, differences in the doxorubicin response of hiPSC-CMs carrying rs2229774 and control hiPSC-CMs are evident in multiple processes that have been identified as downstream determinants of doxorubicin cardiotoxicity, including reduction in cell survival, sarcomeric integrity, ROS production, and mitochondrial function along with increased apoptosis and DNA damage. We confirm that RARG directly represses TOP2B expression to comparatively negligible levels (FIG. 3c), whereas S427L variant leads to de-repression of TOP2B, resulting in comparatively increased TOP2B-mediated DNA damage and decreased mitochondrial biogenesis/function, upon doxorubicin treatment of hiPSC-CMs, a previously established mechanism of DIC (Zhang et al., 2012). Our work comparing the use of RARG overexpression with TOP2B knockout shows similar levels of DIC attenuation, although it is likely that both manipulations function via multiple mechanisms, requiring substantial further research. Interestingly, retinoic acid receptors and topoisomerases are commonly co-localized within the genome, with TOP2B and RARB overlapping each other, and TOP2A and RARA within 30 kb of each other. This genome topology is conserved as far back in evolution as *Xenopus*, suggesting that the control of topoisomerases by retinoic acid receptors may be an evolutionarily ancient mechanism.

Phosphorylation of ERK2 in response to doxorubicin is a well-established phenomenon in DIC that has been connected to mitochondrial protection (Yang et al., 2016). Although we confirm for the first time that this process is also present in hiPSC-CMs and that cells with rs2229774 do not as readily undergo this process, without further mechanistic understanding of the relationship between pERK and mitochondrial function and integrity it is not currently possible to separate this variance from the other mechanisms simultaneously occurring.

Our demonstration that hiPSC-CMs can be used to validate the rs2229774 SNP as causative in DIC provides a powerful tool that can be used to screen other SNPs that have been associated with DIC, although most were discovered in much smaller patient populations or using candidate gene-based methodologies rather than GWAS (Magdy et al., 2016). Ultimately, with suitably validated variants, it will be possible to utilize a genetic test to predict the risk of DIC in patients receiving anthracyclines.

Our data also provide strong support for pre-chemotherapy screening of all patients who will receive doxorubicin for the rs2229774 variant (Aminkeng et al., 2016). For patients who harbor this variant, increased cardiac monitoring, reduction of doxorubicin dosing, and/or the use of the only existing approved cardioprotectant, dexrazoxane, are recommended. In addition, RARG agonist treatment (such as CD1530) has the potential to further protect patients with or without the rs2229774 variant from cardiotoxicity, and further basic and clinical research is clearly warranted, although additional studies in multiple cancer types (such as PDX) to prove that chemotherapy efficacy is not attenuated are needed.

Accession Codes. Gene Expression Omnibus: RNA-seq data have been deposited with accession code GSE79413.

Methods

Human induced pluripotent cell derivation. All pluripotent and reprogramming cell cultures were maintained at 37° C. in Heracell VIOS 160i humidified incubators (Thermo Scientific) with 5% $CO_2$ and 5% $O_2$. Differentiation cultures were maintained at 5% $CO_2$ and atmospheric $O_2$. Protocols were approved by the Northwestern University and University of British Columbia Institutional Review Boards. Patients had previously been genotyped with Illumina Infinium HumanOmniExpress array (738,432 SNPs). With informed written consent, ~9 ml of peripheral blood was taken from each volunteer and shipped at 4° C., samples were transferred to LeucSep tubes (Greiner) filled with Histopaque-1077 (MilliporeSigma). $1 \times 10^6$ isolated peripheral blood mononuclear cells (PMBC) were grown in 24-well tissue culture-treated plates (Greiner) in 2 ml of SFEM II (Stem Cell Technologies) supplemented with 10 ng $ml^{-1}$ IL3, 50 ng $ml^{-1}$ SCF (KITLG), 40 ng $ml^{-1}$ IGF1 (all Peprotech), 2 U $ml^{-1}$ EPO, 1 µM dexamethasone (both MilliporeSigma) (Chou et al., 2015). 50% of the medium was changed every other day. After 12 days of growth, $6 \times 10^4$ cells were transferred to a well of a 24-well plate in 500 µl of SFEM II with growth factors supplemented with CytoTune-iPS 2.0 Sendai Reprogramming Kit viral particles (Invitrogen) (Fusaki et al., 2009) diluted to 10% of the manufacturer's recommendations. Cells were treated with 3.5 µl, 3.5 µl, and 2.2 µl of hKOS ($0.85 \times 10^8$ CIU $ml^{-1}$), hMYC ($0.85 \times 10^8$ CIU $ml^{-1}$), and hKLF4 ($0.82 \times 10^8$ CIU $ml^{-1}$), respectively at MOI of 5:5:3 (KOS:MYC:KLF4). 100% of the medium was changed after 24 h by centrifugation (300 g, 4 min) to 2 ml fresh SFEM II with growth factors, and cells were transferred to one well of a 6-well plate (Greiner) coated with 2 ml of 1:800 growth factor reduced Matrigel (Corning) diluted in DMEM (Corning). 50% of the medium was then changed gently every other day. On d8 after transduction, 100% of medium was changed to E8 medium. E8 medium was made in-house as previously described (Chen et al., 2011) with minor modifications and consisted of DMEM/F12 (10-092-CM, Corning), 20 µg $ml^{-1}$ E. coli-derived recombinant human insulin (Gibco), 64 µg $ml^{-1}$ L-ascorbic acid 2-phosphate trisodium salt (Wako), 5 µg $ml^{-1}$ Oryza sativa-derived recombinant human transferrin (InVitria/VWR), 14 ng $ml^{-1}$ sodium selenite (MilliporeSigma), 100 ng $ml^{-1}$ recombinant human FGF2 (154 amino acids, E. coli-derived, Peprotech), 2 ng $ml^{-1}$ recombinant human TGF31 (112 amino acid, HEK293-derived, Peprotech), and 100 ng $ml^{-1}$ heparin sodium salt (>180 U $mg^{-1}$, MilliporeSigma). Medium was changed every day. At d17 individual colonies were picked in to a Matrigel-treated 12-well plate (one colony per well). Subsequently, cells were expanded in Matrigel-coated 6-well plates by passaging using 0.5 mM EDTA (Gibco) in DPBS without $Ca^{2+}$ or $Mg^{2+}$ (Corning) for 6 min at RT. The identities of all parental hiPSC lines were confirmed by Sanger sequencing of the rs2229774 SNP after PCR amplification of the genomic DNA with the SNP primer set (Table 6).

TABLE 6

PCR sequencing primers for CRISPR/Cas9-mediated genome editing.

| Purpose | Primer name | Sequence |
|---|---|---|
| RARG-KO | P1-F | 5'-GACTTTTGGAGGCCCAGTGG-3' (SEQ ID NO: 1) |
|  | P1-R | 5'-GAGGCCATCTCCTTGGGGA-3' (SEQ ID NO: 2) |
|  | P2-F | 5'-TGCCGAAGCACCCAGATAAG-3' (SEQ ID NO: 3) |
|  | P2-R | 5'-TACCTACATTGCAGGCTGGC-3' (SEQ ID NO: 4) |
| RARG-OE | P3-F | 5'-GGCGCCGGCAGGAAGGAAAT-3' (SEQ ID NO: 5) |
|  | P3-R | 5'-AGCCAGGGCATTGGCCACAC-3' (SEQ ID NO: 6) |
| TOP2B-KO | P4-F | 5'-CTAGGAGTGCGGCGAGTG-3' (SEQ ID NO: 7) |
|  | P4-R | 5'-CCACTTACCACCCAGGTCAG-3' (SEQ ID NO: 8) |
| RARG-SNP | SNP-F | 5'-CATGTGCCTCTGTCCTCCTG-3' (SEQ ID NO: 9) |
|  | SNP-R | 5'-CTGGGAGATGGTCAGTCTGC-3' (SEQ ID NO: 10) |

Human induced pluripotent stem cell culture. Cells were routinely maintained in E8 medium (made as above) on 1:800 diluted growth factor reduced Matrigel. E8 was supplemented with 10 µM Rho kinase inhibitor (Y27632) (LC Labs), hereby referred to as E8Y, for the first 24 h after passage. Cells were passaged at a ratio of ~1:12 to 1:15 every 4 days using 0.5 mM EDTA, achieving ~70-80% confluence. Cell lines were used between passages 20 and 80. All cultures (pluripotent and differentiation) were maintained with 2 ml medium per 9.6 $cm^2$ of surface area or equivalent. All cultures were routinely tested for mycoplasma using a MycoAlert PLUS Kit (Lonza) and a Varioskan LUX (Thermo Scientific) plate reader.

Single nucleotide polymorphism karyotyping. Genomic DNA was extracted from the cell pellets using a Quick-DNA Miniprep Plus kit (Zymo). SNP karyotyping was performed using a whole-genome Infinium CytoSNP-12 BeadChip Array (Illumina) covering 300,000 SNP using a NextSeq 500 (Illumina). Data was analyzed using BlueFuse Multi software (Illumina).

CRISPR/Cas9 gRNA and donor vector design. To generate RARG and TOP2B knockout gRNA expression vectors, two gRNAs targeting alternative start codons of three major RARG splicing variants and one gRNA targeting the start codon of TOP2B were designed using an online CRISPR design tool (tools.genome-engineering.org) with minimal predicted off-target effect (Ran et al., 2013). DNA oligos (IDT) encoding each gRNA with BbsI ligation overhangs were annealed and inserted into the BbsI restriction site of a pSpCas9(BB)-2A-GFP (PX458, Addgene 48138) plasmid (Ran et al., 2013). Cells were FACS selected using a FACSAria SORP (BD Biosciences) in the Northwestern Flow Cytometer Core Facility. The constructed gRNA expression plasmids were confirmed by Sanger sequencing (Eurofins) with the LKO1_5_primer (5'-GACTAT-CATATGCTTACCG-3'). To generate RARG overexpression vector, an AA VS1 gRNA expression vector (Oceguera-Yanez et al., 2016) (pXAT2, Addgene 80494) was used to target AA VS1 locus in the first intron of the PPP1R12C gene (Oceguera-Yanez et al., 2016). Donor plasmid was generated by inserting RARG cDNA (CCSB-Broad LentiORF-RARG Clone, Dharmacon ccsbBroad304_01377) under the CAG promoter of a pAAVS1-Nst-CAG-DEST gateway cloning vector (Addgene 80489), which has a neomycin selection cassette in addition to homology arms for AAVS1. The constructed RARG donor plasmid was confirmed by Sanger sequencing with the P3 primer set (Table 6). To correct the RARG SNP rs2229774 (S427L), a gRNA was designed using an online CRISPR design tool (benchling.com/crispr) based on a) cutting site in close proximity to rs2229774; b) high predicted on-target score; c) minimal predicted off-target effect (Doench et al., 2016). The gRNA with BbsI ligation overhangs was inserted into the pX458 plasmid and confirmed by Sanger sequencing with LKO1_5_primer as described above. A 188 bp single-stranded oligonucleotide (ssODN) repair template (IDT) was designed based on the last exon of RARG with major C allele at the rs2229774 site and a silent mutation at the PAM sequence to protect it from Cas9-mediated degradation, sequence available upon request.

Figure 10:
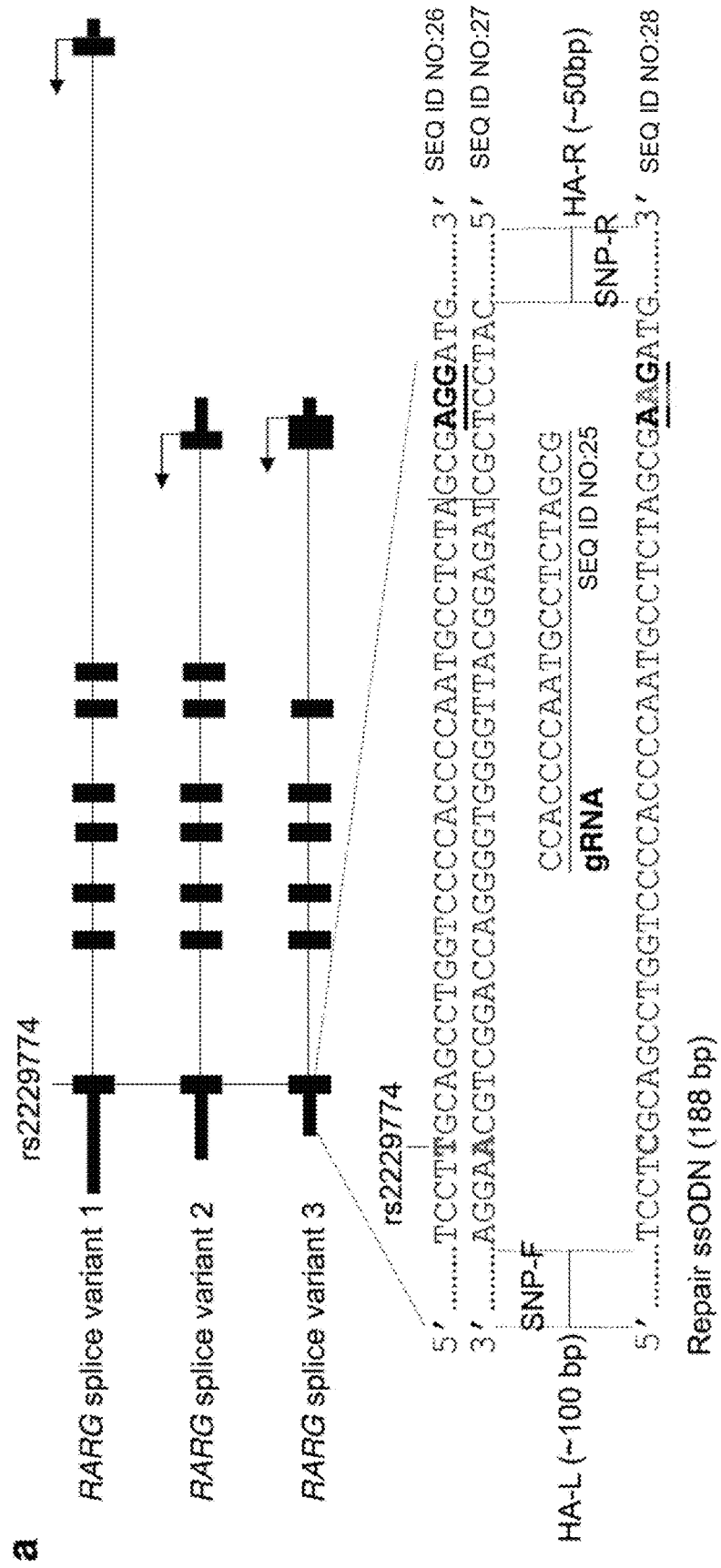
FIG. 10. CRISPR/Cas9-mediated gene correction of the RARG SNP rs2229774 in patient-specific hiPSCs. (a) Schematic of the CRISPR/Cas9-mediated genome editing strategy to correct the SNP rs2229774. Shown are the genomic loci of the three major RARG splice variants, an enlarged view of the last exon harboring the SNP (C/T, highlighted in red), PAM and gRNA targeting sequence (underlined), cutting site of Cas9 (vertical line), PCR primers (SNP-F, SNP-R) in the homology arms (HA) for sanger sequencing and design of repair ssODN containing the major C allele (highlighted in red) at the SNP locus and PAM sequence (underlined) with a silent mutation (highlighted in blue) to protect it from Cas9-mediated degradation. (b) Sanger sequencing confirmation of the precise scarless gene correction at the SNP locus. Top shows the original patient-specific hiPSC line (S427L-2) containing the heterozygous C/T allele at rs2229774 (indicated by the red asterisk) and the wild-type PAM sequence (underlined). Bottom shows the engineered hiPSC line from the same patient harboring the corrected homozygous C allele at the SNP locus (depicted by the red asterisk) and unmodified PAM sequence (underlined) with the wild-type G allele (depicted by the triangular arrow).
Figure 10:
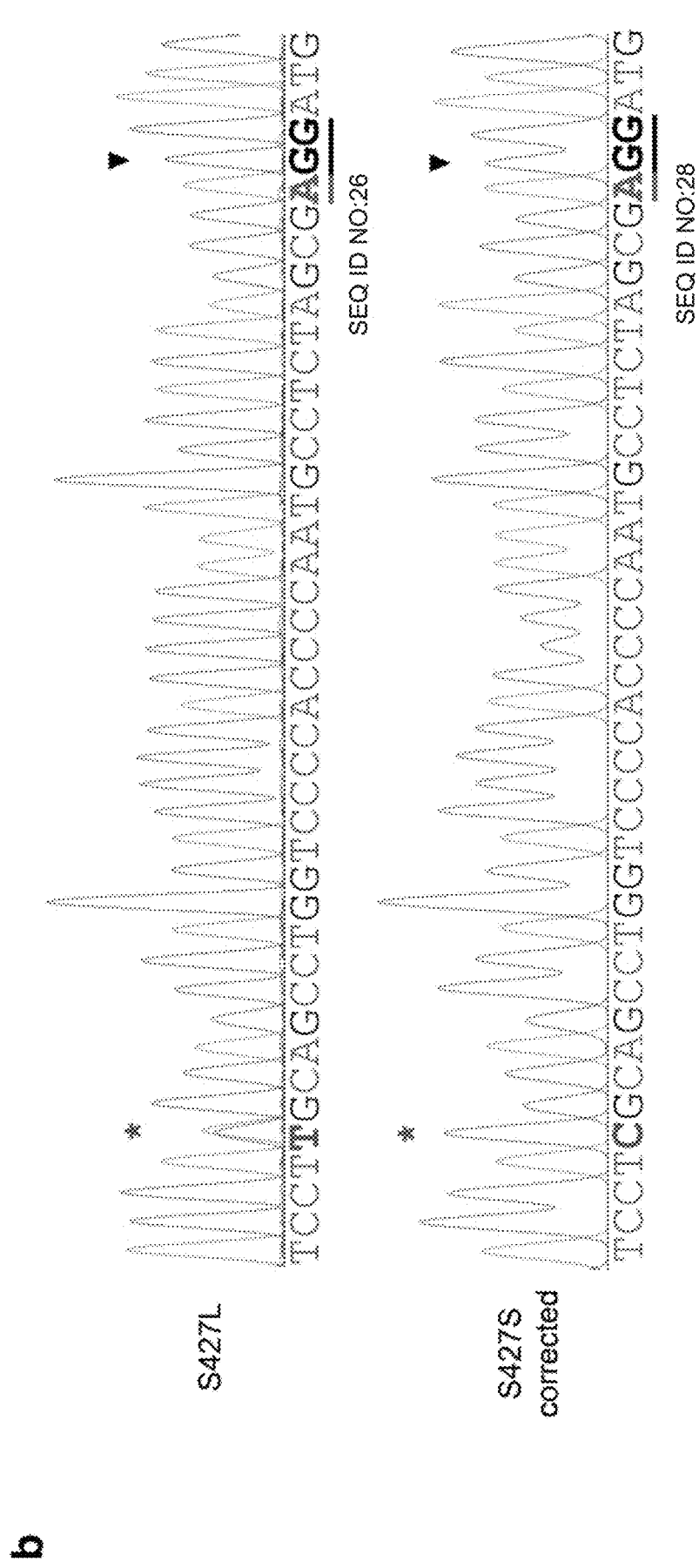
Figure 11:
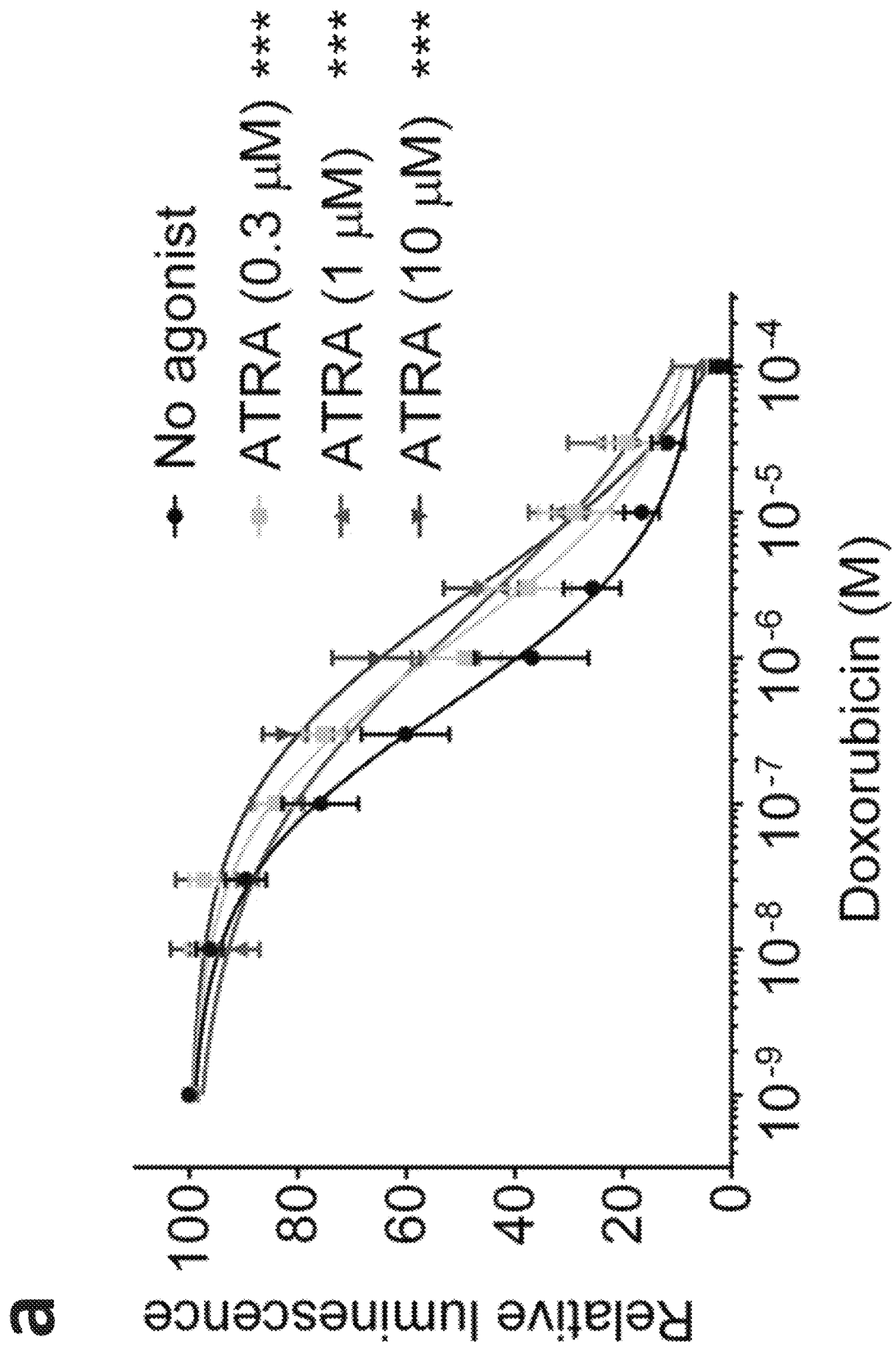
FIG. 11. RARG agonists attenuate doxorubicin cardiotoxicity in hiPSC-CMs without impeding its efficacy in breast cancer cells. (a), (b), (c), and (d): Assessment of cell viability of RARG-WT (a), (b), (c), and (d) hiPSC-CMs after 72 h of doxorubicin and RARG agonists co-treatment at indicated concentrations. n=6 replicates for each data point. (e), (f), and (g): Assessment of cell viability of S427L-1 hiPSC-CMs after 72 h of doxorubicin and RARG agonists co-treatment at indicated concentrations. n=6 replicates for each data point. (h), (i), and (j): Assessment of cell viability of three breast cancer cell lines after 72 h of doxorubicin and RARG agonists (1 µM each) co-treatment. n=2 replicates for each data point. Throughout, data are represented as mean±s.e.m. *P<0.05; P<0.005; *P<0.0001; by F-test.
Figure 11:
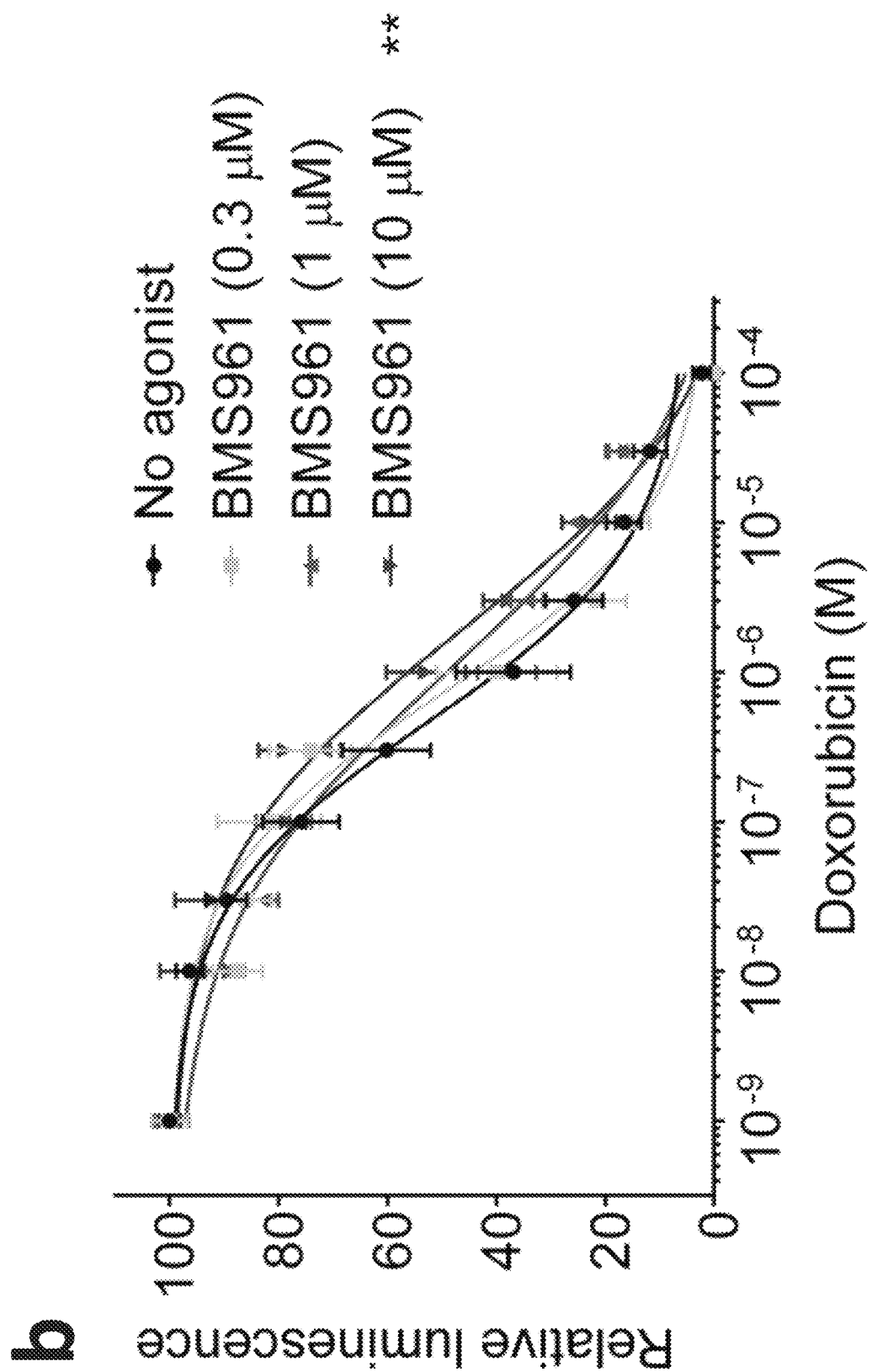
Figure 11:
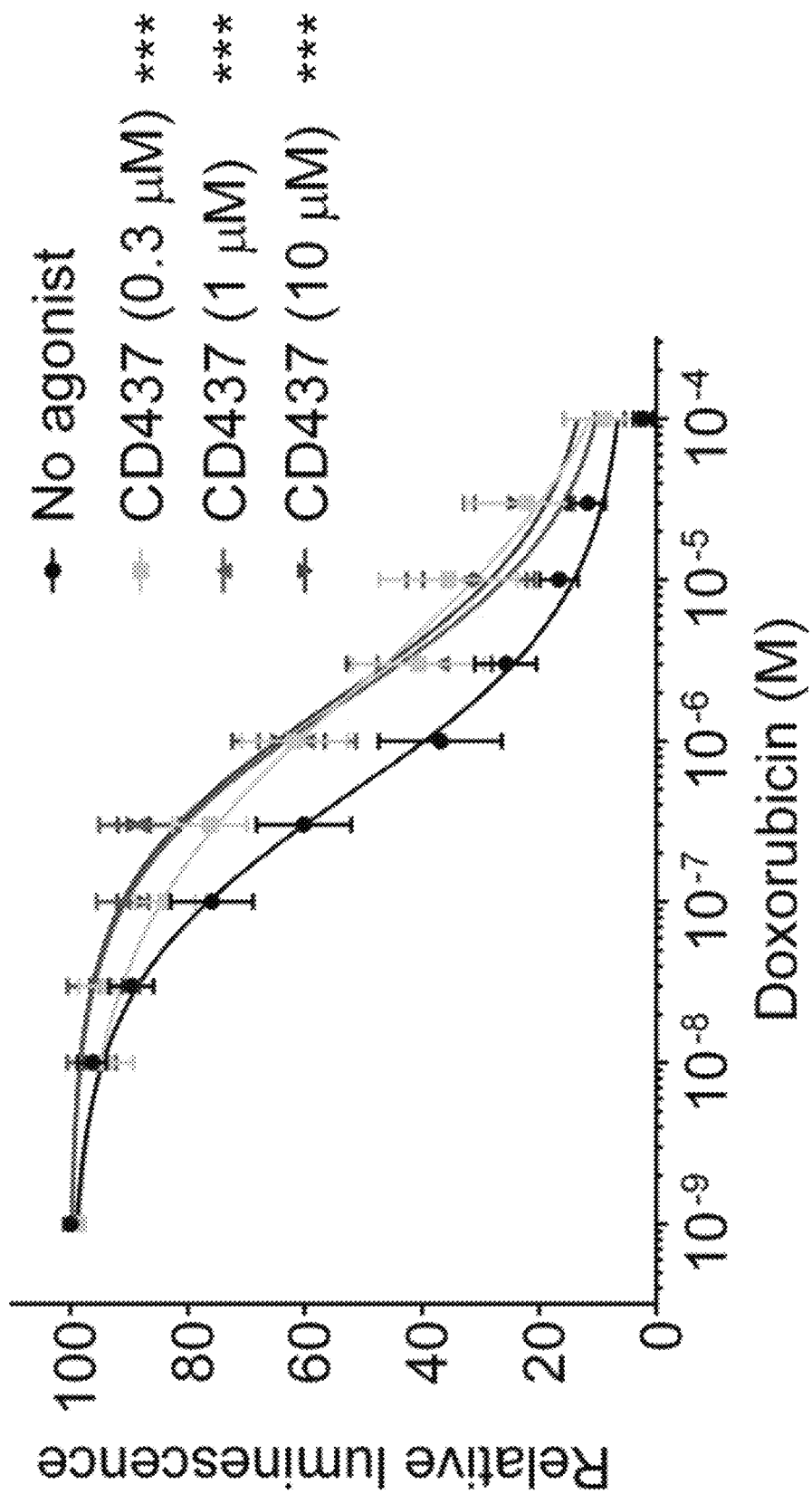
Figure 11:
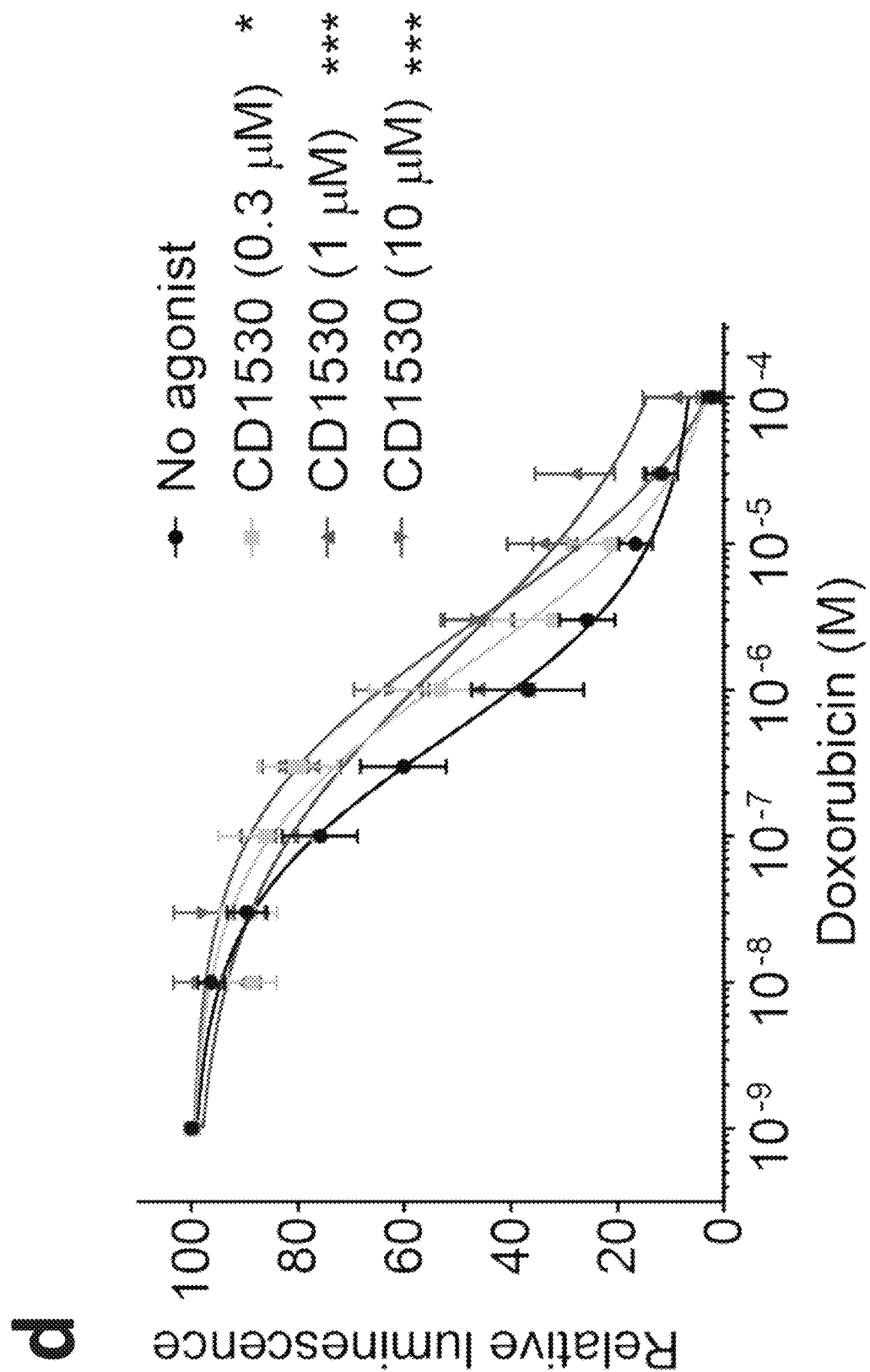
Figure 11:
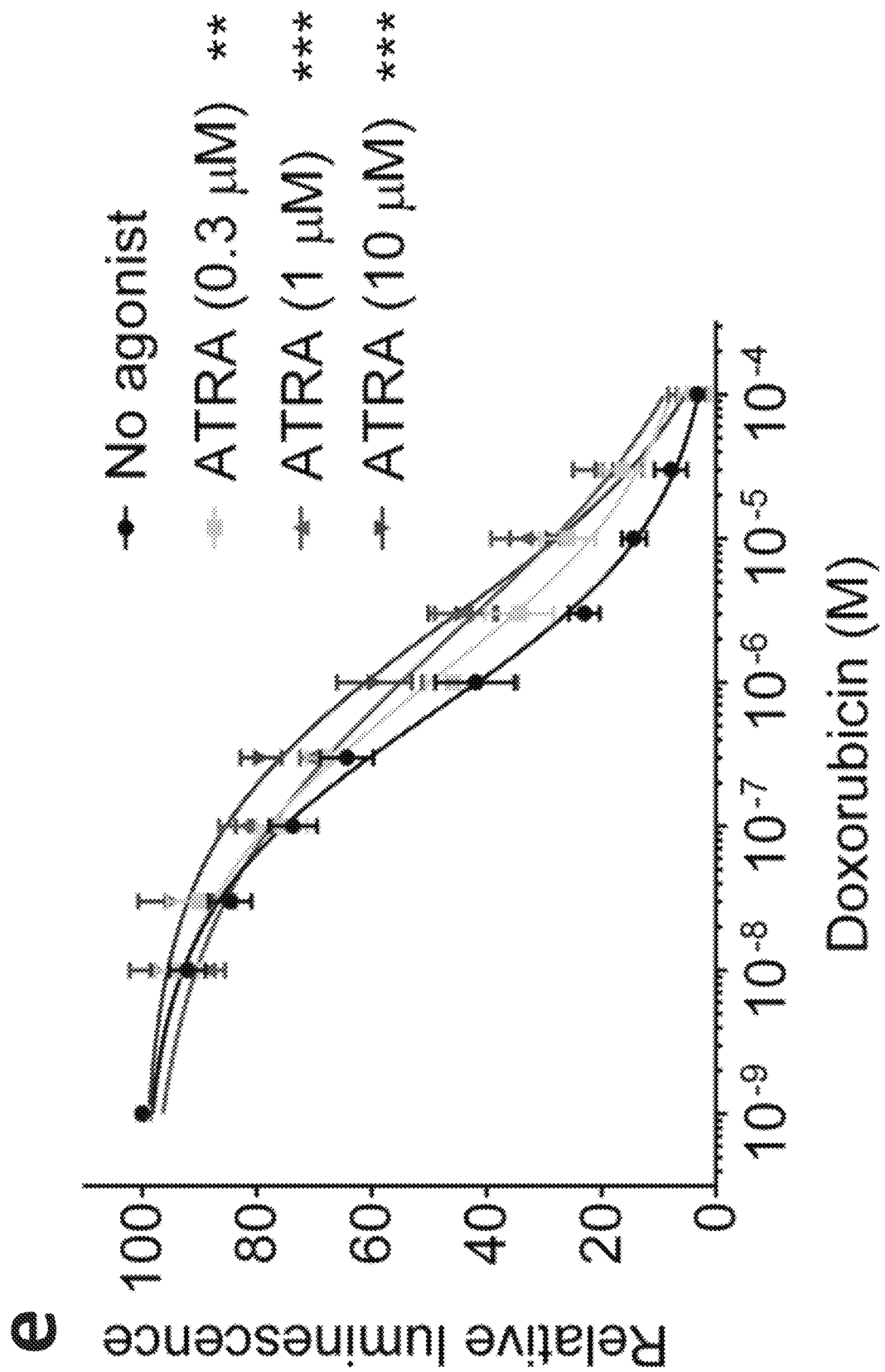
Figure 11:
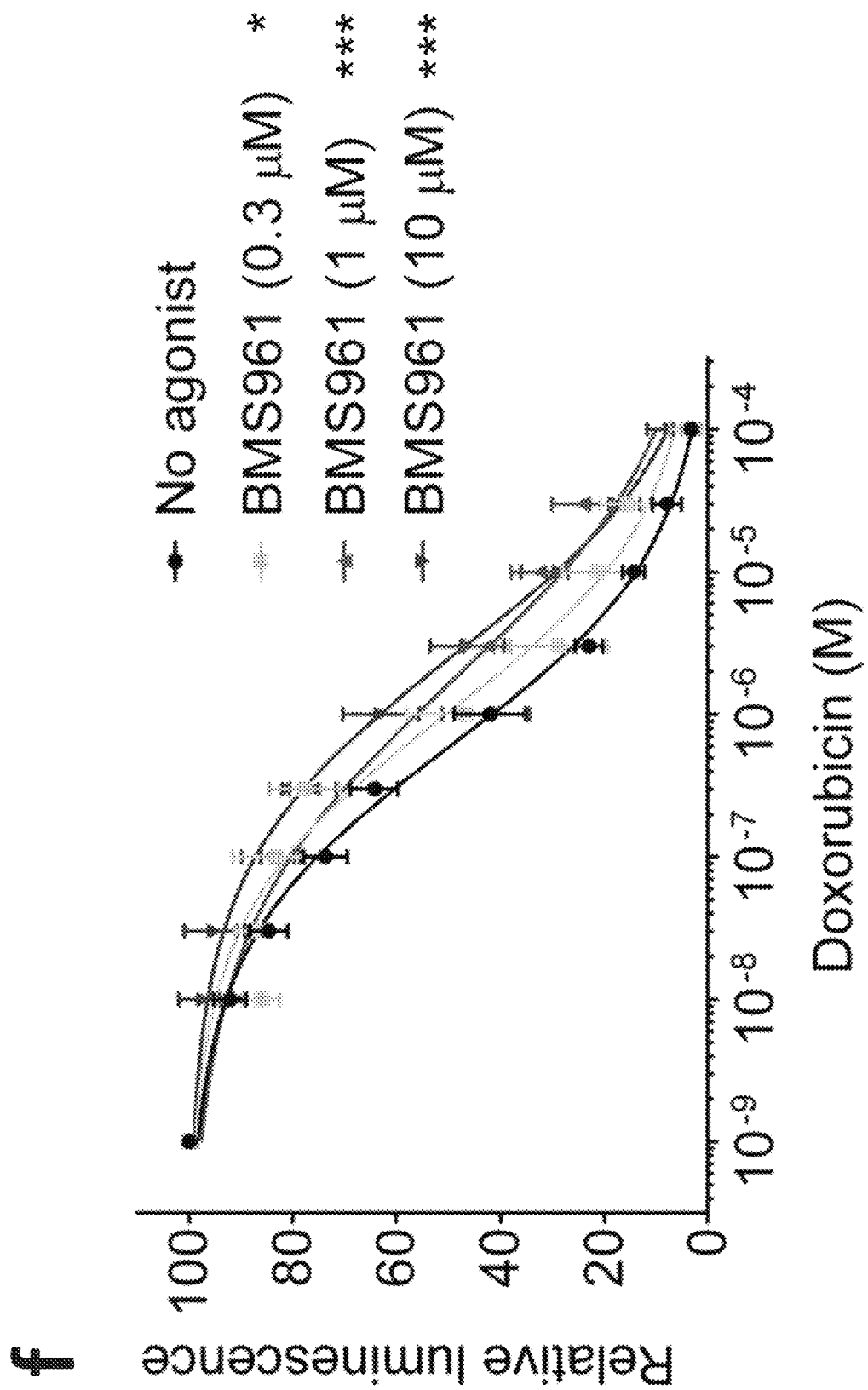
Figure 11:
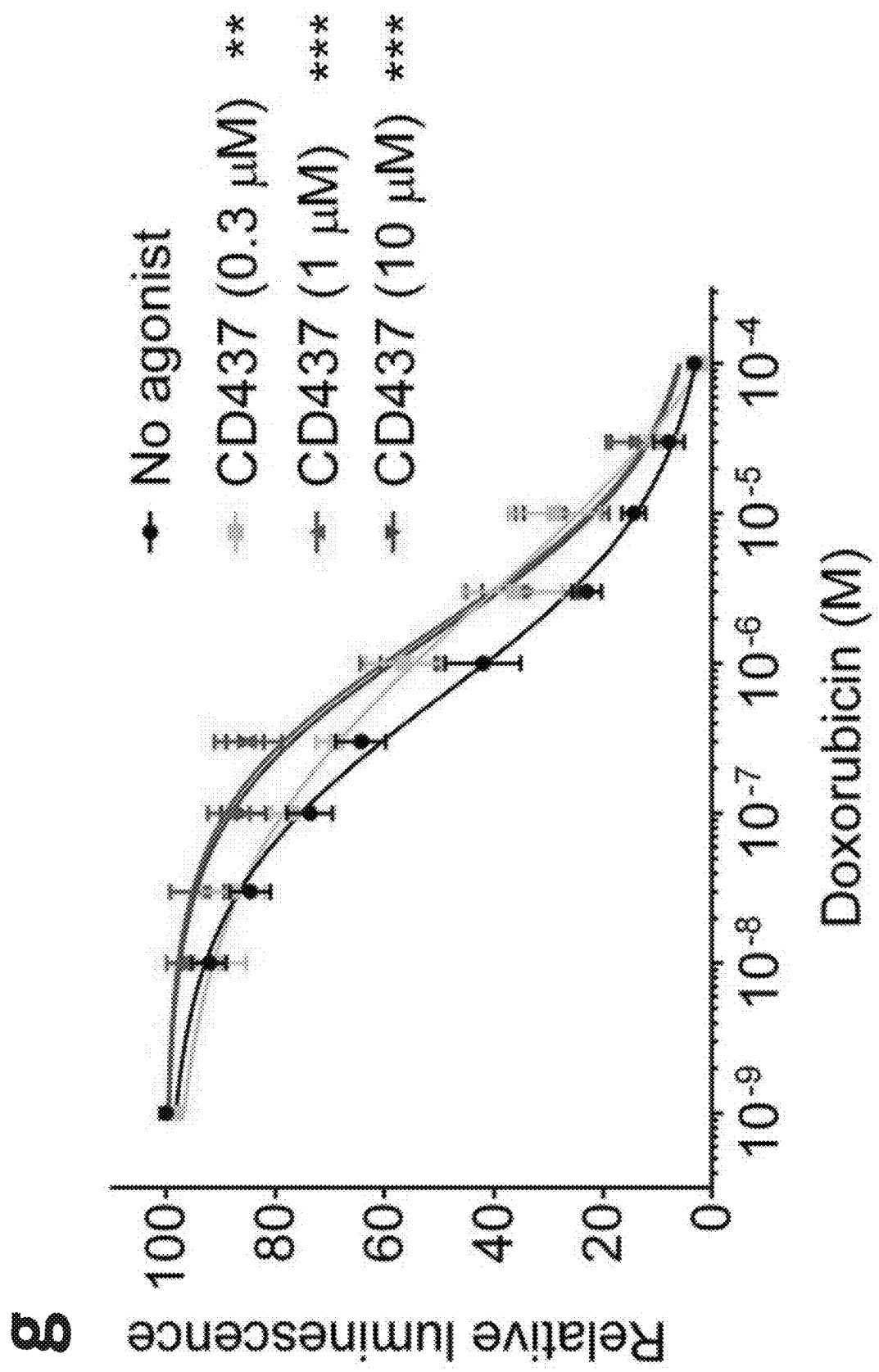
Figure 11:
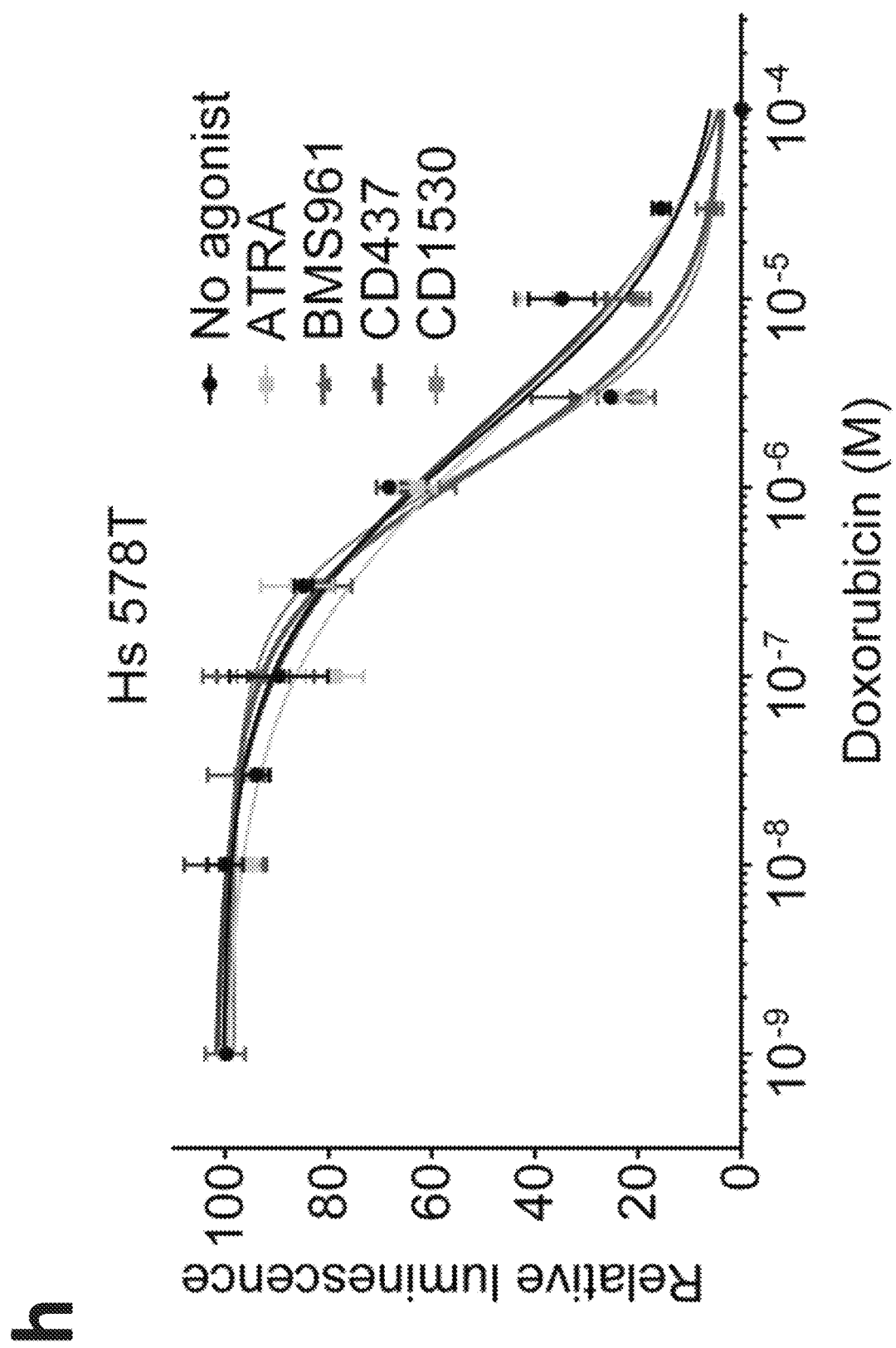
Figure 11:
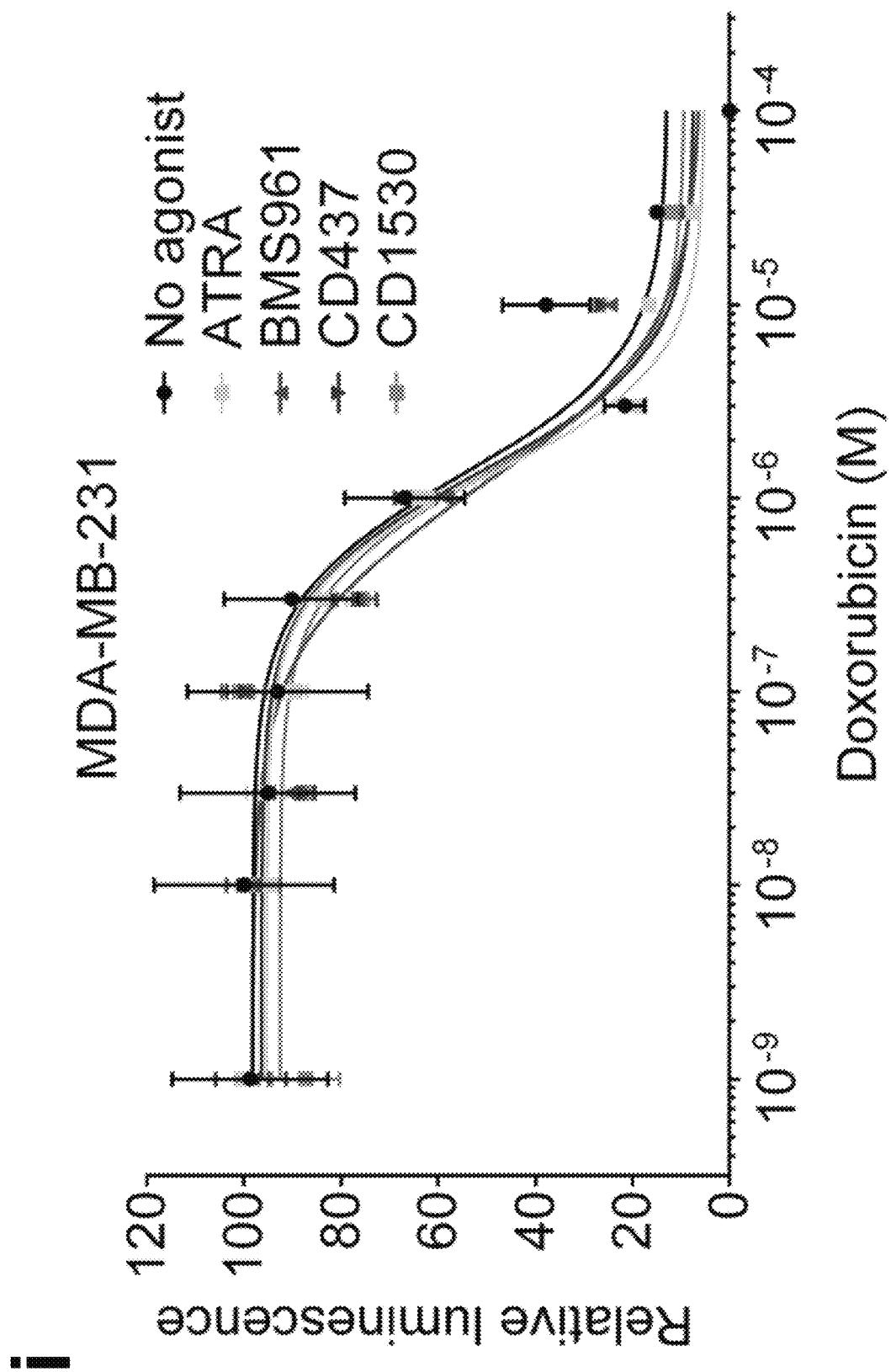
Figure 11:
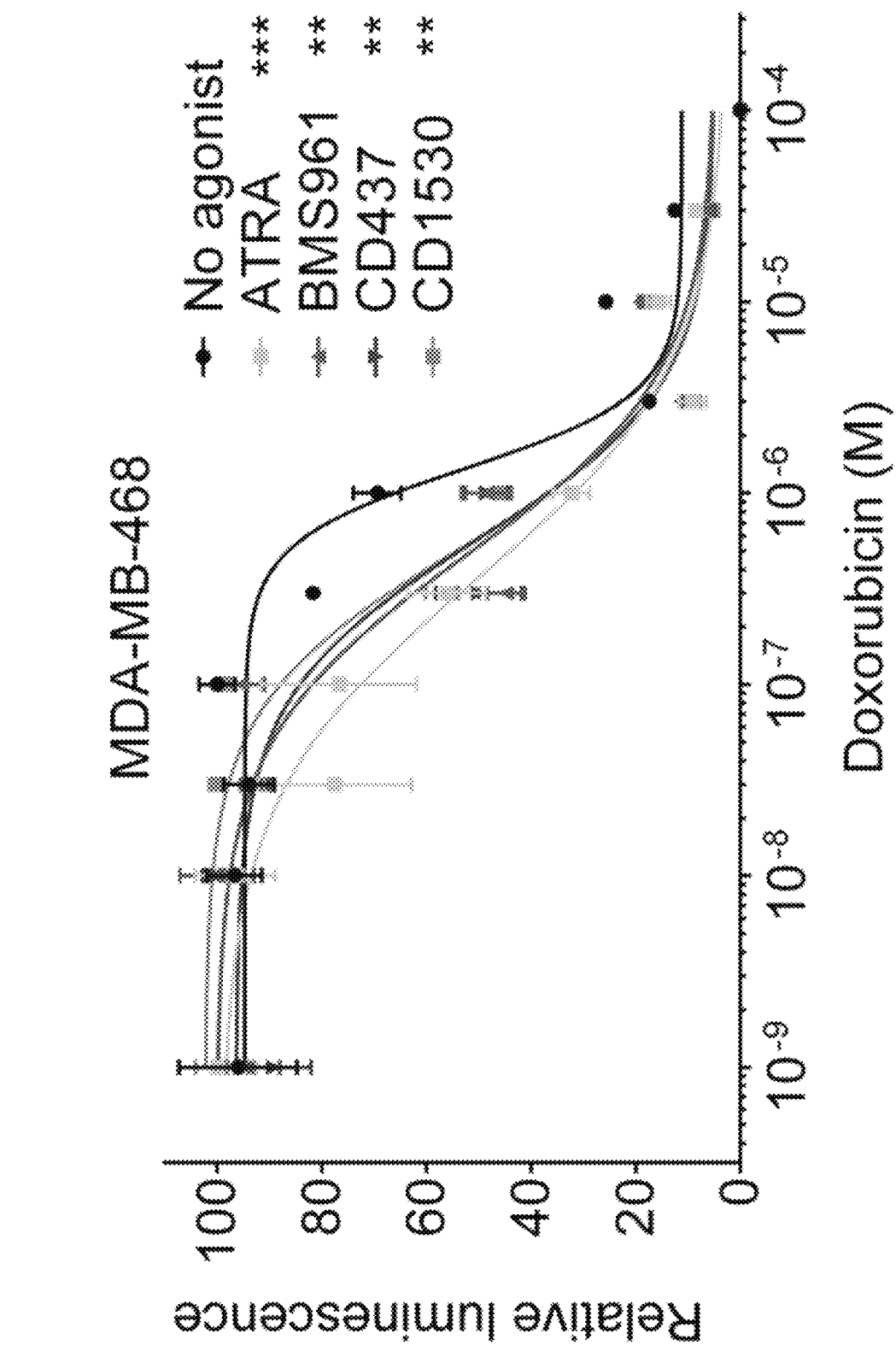

CRISPR/Cas9-mediated genome editing of hiPSC. hiPSC were cultured in E8 medium to ~80% confluence before electroporation. Cells were harvested using TrypLE Express (Gibco) for 3 min at RT and resuspended in E8Y medium. To generate RARG and TOP2B knockout hiPSCs, $5\times10^6$ cells from the isogenic RARG-WT hiPSC line were electroporated with 1 µg of each gRNA expression vector (FIG. 7a and FIG. 8d). To generate RARG overexpression hiPSCs, $5\times10^6$ cells from the same isogenic hiPSC line were electroporated with 3 µg AAVS1 gRNA expression vector (pXAT2, Addgene) and 1 µg RARG donor plasmid (FIG. 7b). For RARG SNP correction, $5\times10^6$ cells from S427L-2 hiPSC line were electroporated with 3 µg gRNA expression vector and 1 µl of 10 µM ssODN repair template (FIG. 10a). Cells were maintained for 48 h in E8Y medium (for RARG and TOP2B knockout) or in E8Y medium supplemented with 1 µM SCR7 inhibitor (Chu et al., 2015) (Xcess Biosciences) (for RARG SNP correction) on Matrigel-coated plates followed by FACS sorting (FACSAria SORP, BD Biosciences) of a single-cell suspension for cells expressing GFP, and subsequently plated at a low density (500 cells per 9.6 cm$^2$ of surface area) in E8Y medium on 1:800 diluted growth factor reduced Matrigel for the first 48 h and in E8 medium thereafter. Individual colonies were picked and expanded ~12 days after electroporation. Correctly targeted clones were identified by genomic sequencing with primers outside of the targeting region (Table 6). For RARG overexpression, cells were maintained for 48 h in E8Y medium on Matrigel-coated plates followed by E8Y medium supplemented with 100 µg ml$^{-1}$ of geneticin (Gibco) for one week of neomycin selection. Neomycin resistant colonies were subsequently validated for RARG insertion at AAVS1 locus by genomic sequencing with the P3 primer set (Table 6).

Cardiac differentiation. Differentiation into cardiomyocytes was performed as previously described (FIG. 6b) (Burridge et al., 2015; Burridge et al., 2014). All cell lines for each individual experiment were differentiated in parallel to further reduce experimental variability. Briefly, hiPSCs were split at a 1:15 ratio using 0.5 mM EDTA as above and grown in E8 medium for 4 days reaching ~80% confluence. At the start of differentiation (day 0), E8 medium was changed to CDM3 (Burridge et al., 2014), consisting of RPMI 1640 (Corning), 500 µg ml$^{-1}$ *Oryza sativa*-derived recombinant human albumin (Oryzogen), and 213 µg ml$^{-1}$ L-ascorbic acid 2-phosphate (Wako). For the first 24 h, CDM3 medium was supplemented with 6 µM of glycogen synthase kinase 3-β inhibitor CHIR99021 (LC Labs). On day 1, medium was changed to CDM3 and on day 2 medium was changed to CDM3 supplemented with 2 µM of Wnt inhibitor Wnt-C59 (Biorbyt). Medium was then changed on day 4 and every other day for CDM3. Contracting cells were noted from day 7. On day 10, medium was changed to CDM3-L consisting of RPMI 1640 no glucose (Corning), CDM3 supplement, and with 4 mM L-lactic acid (Sigma-Aldrich). On day 14, cardiomyocytes were dissociated using DPBS for 20 min at 37° C. followed by 1:200 Liberase TH (Roche) in DPBS for 20 min at 37° C., centrifuged at 300 g for 5 min, filtered through a 100 pun cell strainer (Fisherbrand). Live cells were counted using a LUNA-FL Dual Fluorescence cell counter (Logos Biosystems) then plated onto Matrigel-treated Nunc Lab-Tek II 8-chamber slides (50,000 cells per well), No 1.5 coverslips (100,000 cells per coverslip) in 12-well plates, 24-well plates ($1\times10^6$ cells per well), or 384-well white-sided µClear plates (25,000 cells per well) (all Greiner), in CDM3 medium supplemented with 40% FBS (Seradigm, VWR) for 48 h and changed back to CDM3 medium thereafter. Cardiomyocytes were used for analysis between day 20 and 30 days after differentiation.

Immunofluorescent staining. hiPSCs were dissociated with 0.5 mM EDTA and plated onto Matrigel-coated Nunc Lab-Tek II 8-chamber slides in E8 medium for three days (E8Y for the first 24 h). Cells were fixed, permeabilized, and stained for POU5F1, SSEA4, SOX2, TRA-1-60 with the PSC 4-Marker Immunocytochemistry Kit (Invitrogen) according to manufacturer's instructions. Cardiomyocytes were dissociated with Liberase TH (as above) and plated onto Matrigel-coated No 1.5 coverslips as previously described and allowed to adhere and spread for 4 days. Cells were fixed with 4% paraformaldehyde (Electron Microscopy Services) in DPBS for 15 min at RT, permeabilized with 1% saponin (MilliporeSigma) in DPBS for 15 min at RT, blocked with 3% bovine serum albumin (BSA, MilliporeSigma) in DPBS for 30 min at RT, and stained overnight in 3% BSA/DPBS at 4° C. with 1:200 polyclonal rabbit IgG anti-TNNT2 (Abcam, ab45932), 1:500 monoclonal mouse IgG$_1$ anti-ACTN2 (Sigma, A7811), 1:200 monoclonal rabbit IgG RARG (Abcam, ab187159), or 1:200 monoclonal mouse IgG$_1$ γH2AX (MilliporeSigma, 05-636). Cells were washed and then stained with secondary antibodies 1:1000 Alexa Fluor 488 goat anti-rabbit IgG, Alexa Fluor 594 goat anti-mouse IgG$_1$, or Alexa Fluor 488 goat anti-mouse IgG$_1$, Alexa Fluor 594 goat anti-rabbit IgG (all Invitrogen) in 3% BSA/DPBS for 1 h at RT in the dark. Cells were washed three times and mounted with ProLong Diamond Antifade Mountant with DAPI (Invitrogen). Slides were imaged with a Ti-E inverted fluorescent microscope (Nikon Instruments) and a Zyla sCMOS camera (Andor) using NIS-Elements 4.4 Advanced software.

Flow cytometry. hiPSCs were dissociated with TrypLE Express (Gibco) for 3 min at RT and $1\times10^6$ cells were transferred to flow cytometry tubes (Fisherbrand). For staining of surface markers, cells were incubated in 1% FBS and 0.09% sodium azide (MilliporeSigma) in DPBS using 1:20 mouse IgG$_3$ SSEA4-488 (BD Biosciences, 560308) for 30 min at RT then washed. For intracellular staining, cells were fixed and permeabilized with −20° C. methanol (Fisher Bioreagents) for 10 min, washed with DPBS, and stained using 1:20 mouse IgG$_1$ POU5F1-647 (BD Biosciences, 560307), and mouse IgG$_1$ NANOG-647 (BD Biosciences, 561300) for 30 min at RT then washed. Isotype controls mouse IgG$_3$-488 (BD Biosciences, 563636) and mouse IgG$_1$-647 (BD Biosciences, 565571) were used to establish gating. For staining of intracellular markers, cardiomyocytes were dissociated with Liberase TH (as above), fixed and permeabilized with −20° C. methanol for 10 min, washed with DPBS, and stained using 1:500 mouse monoclonal IgG$_1$ TNNT2-647 (BD Biosciences, 565744) or 1:500 mouse monoclonal IgG$_{2b}$ MYH-PE (BD Biosciences, 564408) for 30 min at RT and washed again with DPBS. Isotype controls mouse IgG$_1$-647 (BD Biosciences, 565571) and mouse IgG$_{2b}$-PE (BD Biosciences, 555743) were used to establish gating. Human dermal fibroblasts showed no positive staining under these conditions. All cells were analyzed using a CytoFLEX (Beckman Coulter) with CytExpert 2.0 software.

Doxorubicin treatment. Doxorubicin hydrochloride (HY-15142, MedChem Express) was resuspended to 10 mM in cell culture-grade water (Corning) and aliquots were stored at −20° C. Day 30 hiPSC-CMs were treated for 24 h or 72 h with doxorubicin (0.01-100 µM) diluted in RPMI 1640 medium (no phenol red, Corning) supplemented with 500 µg ml$^{-1}$ recombinant human serum albumin (Oryzogen). For RARG agonist treatment, day 30 hiPSC-CMs were treated with respective agonist (all from Tocris, resuspended in DMSO) for 24 h prior to doxorubicin administration and then a second dose was co-administered with doxorubicin as above.

384-well plate-based cell viability, caspase 3/7 activity, and reactive oxygen species (ROS) assays. To measure cell viability after 72 h of doxorubicin (0.01-100 µM) treatment, CellTiter-Glo 2.0 (Promega) was used per manufacturer's instructions. Luminescence was measured using a VarioSkan Lux Multi-Mode Reader (Thermo Scientific) with an integration time of 0.25 sec. 10 µM staurosporine (MedChemExpress) was used as a positive control. After 24 h of doxorubicin (0.01-100 µM) treatment, apoptosis and ROS was measured using Caspase 3/7-Glo and ROS-Glo H$_2$O$_2$ (both Promega) respectively according to manufacturer's instructions with an integration time of 1 sec. 10 µM staurosporine and 50 µM menadione (both MedChemExpress) was used as a positive control, respectively. Data were analyzed using Prism 7.0 software (GraphPad) using standard dose-response guidelines.

Mitochondrial membrane potential assay. hiPSC-CMs were cultured on Matrigel-coated Nunc Lab-Tek II 8-chamber slides, treated with doxorubicin for 24 h, washed and stained with JC-10 (Enzo Life Sciences) diluted to 2 µM in RPMI 1640, for 30 min at 37° C., then mounted with ProLong Diamond Antifade Mountant with NucBlue live cell stain (Invitrogen). 50 µM FCCP (MedChemExpress) was used as a positive control. Slides were imaged with a Ti-E inverted fluorescent microscope (Nikon Instruments) and a Zyla sCMOS camera (Andor) using NIS-Elements 4.4 Advanced software.

Flow cytometry-based DNA damage assay. After 24 h of doxorubicin treatment, hiPSC-CMs were dissociated with Liberase TH as described before, processed with BD Cytofix/Cytoperm fixation/permeabilization kit per manufacturer's instructions, and stained with 1:20 mouse IgG$_1$ γH2AX-647 (BD Biosciences, 560447) at 4° C. for 30 min in the dark and washed again with DPBS. Isotype control mouse IgG$_1$-647 (BD Biosciences, 565571) was used to establish gating. Cells were analyzed using a CytoFLEX (Beckman Coulter) with CytExpert 2.0 software and Prism 7.0 software (GraphPad).

RNA-seq gene expression analysis. Day 30 hiPSC-CMs from 6 patients (3 Control and 3 S427L) were treated with 1 µM doxorubicin or vehicle for 24 h. We have previously determined that this is a physiologically relevant dose (Burridge et al., 2016). RNA was extracted using TRI Reagent and Direct-zol RNA microprep kit (both Zymo) including on-column DNase digestion to remove genomic DNA. Samples were quantified using an Agilent 2100 Bioanalyzer and passed QC. Library preparation was done using a TruSeq RNA v2 kit (Illumina) and sequencing with NextSeq 500 instrument (Illumina) by Northwestern's NuSeq core facility, generating ~40 million single-end 75 bp reads for each sample. Reads were mapped to the GRCh38 reference human genome using Subread software (Liao et al., 2013). Gene expression levels and exon usage were estimated using featureCounts function in the Subread software (Liao et al., 2013). Differential gene expression analysis was done using Deseq2 package (Love et al., 2014) and R (v3.3.3). Bioinformatics script and codes for the analysis are available upon request.

Quantitative Real-time PCR. RNA was isolated using a TRI reagent and Direct-zol RNA microprep kit (Zymo) including on-column Dnase digestion to remove genomic DNA. cDNA was produced from 1 µg of total RNA using the High Capacity RNA-to-cDNA kit (Applied Biosystems). All PCR reactions were performed in triplicate in a 384-well plate format using TaqMan Gene Expression Master Mix in a QuantStudio 5 Real-Time PCR System (both Applied Biosystems) with following TaqMan Gene Expression Assays (Life Technoloiges): 18S (Hs99999901_s1), ACTB (Hs01060665_g1), GAPDH (Hs02786624_g1), NANOG (Hs02387400_g1), POU5F1 (Hs00999632_g1), SOX2 (Hs01053049_s1), KLF4 (Hs00358836_m1), LIN28 (Hs00702808_s1), MYC (Hs00153408_m1), UTF1 (Hs00747497_g1), DNMT3B (Hs01003405_m1), TERT (Hs99999022_m1), ZFP42 (Hs00399279_m1), TP53 (Hs99999147_m1), RARG (Hs01559234_m1), TOP2B (Hs00172259_m1), PPARGC1A (Hs00173304) and PPARGC1B (Hs00993805_m1). Relative quantification of gene expression was calculated using $2^{-\Delta\Delta Ct}$ method (Schmittgen and Livak, 2008), normalized to the reference 18S, ACTB, or GAPDH and untreated control samples as specified in the figure legends.

Western blot. We washed and harvested cells in cold PBS and collected them by centrifugation at 20,000 g for 10 min. at 4° C. Pellet was lysed in PBS containing 1% SDS and protease inhibitors (cOmplete, ROCHE) and sonicated (2 pulses of 12 sec at 125 Watt) to shear DNA. We centrifuged the samples at 20,000 g for 15 min. at RT to precipitate and discard the insoluble material and the protein concentration in the supernatant was quantified using BCA assay (Thermo Scientific) following manufacturer's instructions. 20 µg protein/sample were subject to SDS-PAGE in a 9% acrylamide gel for 45 min. at 180 V. and transferred to a PVDF membrane (Immobilon-P, Millipore) at 200 mA. For 90 min. Membranes were blocked in TBST containing 5% milk for 1 h. at RT and incubated at 4° C. overnight with the following primary antibodies: 1:1000 monoclonal rabbit IgG RARG (Abcam, ab187159), 1:1000 polyclonal rabbit IgG TOP2B (Abcam, ab125297), 1:5000 polyclonal rabbit IgG β-Tubulin (Sigma, T2200), 1:5000 monoclonal mouse IgG2a β-Actin (Sigma, A5316). The membrane was washed three times for 10 min with TBST and incubated with the appropriate secondary antibody: 1:5,000 HRP-goat anti-mouse IgG or HRP-goat anti-rabbit IgG (GE NA931V and NA934V) for 1 h. at RT. After three additional washes with TBST, membranes were developed by chemiluminiscence (SuperSignal West Pico, Thermo Scientific). Signals were captured using a CCD camera-based imager (Azure Biosystems) and quantified using Image J software. Mice heart tissues were harvested and homogenized using lysis buffer (80 mM NaCl, 0.05% Triton X, 1 mM EDTA, 20 mM HEPES, 0.5% sodium deoxycholate, 1 mM DTT, 20 mM β-glycerophosphate) with TissueLyser LT (Qiagen) and centrifuged at 10,000 rpm for 15 min at 4° C. Proteins were quantified with Bradford (Bio-Rad) and separated by Tris-Glycine SDS/PAGE (Bio-Rad). Transferred proteins on nitrocellulose membrane were probed against TOP2B (R&D Systems), phosphorylated ERK1/2 (Cell Signaling Technologies), BCL2 (Santa Cruz Biotechnology), and GAPDH (Advanced ImmunoChemical).

MSD analysis of phosphorylated ERK. hiPSC-CMs were collected in lysis buffer (150 mM NaCl, 1% TritonX-100, 50 mM Tris-HCl, pH 8.0) supplemented with Phosphatase Inhibitor II (1:100, Sigma-Adrich), Phosphatase Inhibitor Cocktail 3 (1:100, Sigma-Adrich), 1 mM $NaVO_4$ and protease inhibitors (cOmplete, ROCHE). We centrifuged the samples at 50,000 g for 15 min. at 4° C. to precipitate and discard the insoluble material and the protein concentration in the supernatant was quantified using BCA assay (Thermo Scientific) following manufacturer's instructions. 2.5 μg protein/sample were analyzed using the MSD Phospho (Thr202/yr204; Thr185/Tyr187)/Total ERK1/2 Assay Whole Cell Lysate Kit (Meso Scale Discovery, K15100D-1), according to manufacturer's recommendations. The ratio of phosphorylated ERK was normalized to Total ERK1/2 signal, and analyzed using Prism 7.0 software (GraphPad).

Breast cancer cell lines. Four human breast cancer cell lines were used, MCF7 (adenocarcinoma, ATCC HTB-22) and Hs 578T (carcinsarcoma, ATCC HTB-126) both cultured in RPMI 1640 (Corning) with 10% FBS (Opti-Gold, GenDEPOT), MDA-MB-231 (adenocarcinoma, ATCC HTB-26) and MDA-MB-468 (adenocarcinoma, ATCC HTB-131) both cultured in DMEM (Corning) with 10% FBS. All cells were cultured on uncoated tissue culture plates (Greiner) and passaged with TrypLE Express (Gibco).

Mouse model of doxorubicin-induced cardiomyopathy and drug administration. C57BL/6J Mice were treated with doxorubicin (NovaPlus) alone as a control (n=16), either co-treated with ATRA (all-trans retinoic acid, R2625 Sigma-Aldrich) or CD1530 (RARG-specific agonist, CAS107430-66-0, Tocris Bioscience) as experimental groups (n=8 and n=10, respectively). Mice were pretreated with CD1530 or ATRA (12 mg $kg^{-1}$ each) for 3 days (day −3~day 0) and at day 0, mice were treated with doxorubicin (3 mg $kg^{-1}$) intraperitoneally twice a week and CD1530 or ATRA once a day by oral gavage for 3 weeks (day 0-day 21). For the control group, we treated mice with corn oil in the same schedule as agonist administration. We recorded an echocardiogram once a week (day 0, day 7, day 14, and day 21) and terminated the experiment at day 21. Hearts were harvested for western blot analyses as mentioned above.

Echocardiographic evaluation. Mice were studied at baseline and weekly during the protocol under light anesthesia with isoflurane (induction 3%, maintenance 1.5%). 2D images in the parastemal short axis were obtained with a GE Vivid 7 ultrasound system (GE Healthcare) equipped with a 13 MHz transducer. Left ventricular end-systolic (LVESD) and end-diastolic (LVEDD) dimensions were measured and left ventricular fractional shortening (FS) was calculated.

Statistical methods. Data were analyzed in Excel or R and graphed in GraphPad Prism 7. Detailed statistical information is included in the corresponding figure legends. Data were presented as mean±SEM. Comparisons were conducted via one way-ANOVA test, an unpaired two-tailed Student's t-test, or F-test with significant differences defined as $P<0.05$ (*), $P<0.005$ (), and $P<0.0001$ (*). Our sample size (3 patients in each category) was based on the feasibility of handling this number of hiPSC lines. Patient exclusion criteria are outlined in Table 1. No statistical methods were used to predetermine sample size. The experiments were not randomized and the investigators were not blinded to allocation during experiments and outcome assessment.

REFERENCES

Aggarwal, S., Kim, S. W., Cheon, K., Tabassam, F. H., Yoon, J. H., and Koo, J. S. (2006). Nonclassical action of retinoic acid on the activation of the cAMP response element-binding protein in normal human bronchial epithelial cells. Mol Biol Cell 17, 566-575.

Aminkeng, F., Bhavsar, A. P., Visscher, H., Rassekh, S. R., Li, Y., Lee, J. W., Brunham, L. R., Caron, H. N., van Dalen, E. C., Kremer, L. C., et al. (2015). A coding variant in RARG confers susceptibility to anthracycline-induced cardiotoxicity in childhood cancer. Nat Genet 47, 1079-1084.

Aminkeng, F., Ross, C. J., Rassekh, S. R., Hwang, S., Rieder, M. J., Bhavsar, A. P., Smith, A., Sanatani, S., Gelmon, K. A., Bernstein, D., et al. (2016). Recommendations for genetic testing to reduce the incidence of anthracycline-induced cardiotoxicity. Br J Clin Pharmacol 82, 683-695.

Berlin, V., and Haseltine, W. A. (1981). Reduction of driamycin to a semiquinone-free radical by NADPH cytochrome P-450 reductase produces DNA cleavage in a reaction mediated by molecular oxygen. J Biol Chem 256, 4747-4756.

Blanco, J. G., Sun, C. L., Landier, W., Chen, L., Esparza-Duran, D., Leisenring, W., Mays, A., Friedman, D. L., Ginsberg, J. P., Hudson, M. M., et al. (2012). Anthracycline-related cardiomyopathy after childhood cancer: role of polymorphisms in carbonyl reductase genes—a report from the Children's Oncology Group. J Clin Oncol 30, 1415-1421.

Boyle, E. A., Li, Y. I., and Pritchard, J. K. (2017). An Expanded View of Complex Traits: From Polygenic to Omnigenic. Cell 169, 1177-1186.

Burridge, P. W., Holmstrom, A., and Wu, J. C. (2015). Chemically Defined Culture and Cardiomyocyte Differentiation of Human Pluripotent Stem Cells. Curr Protoc Hum Genet 87, 21 23 21-15.

Burridge, P. W., Li, Y. F., Matsa, E., Wu, H., Ong, S. G., Sharma, A., Holmstrom, A., Chang, A. C., Coronado, M. J., Ebert, A. D., et al. (2016). Human induced pluripotent stem cell-derived cardiomyocytes recapitulate the predilection of breast cancer patients to doxorubicin-induced cardiotoxicity. Nat Med 22, 547-556.

Burridge, P. W., Matsa, E., Shukla, P., Lin, Z. C., Churko, J. M., Ebert, A. D., Lan, F., Diecke, S., Huber, B., Mordwinkin, N. M., et al. (2014). Chemically defined generation of human cardiomyocytes. Nat Methods 11, 855-860.

Canon, E., Cosgaya, J. M., Scsucova, S., and Aranda, A. (2004). Rapid effects of retinoic acid on CREB and ERK phosphorylation in neuronal cells. Mol Biol Cell 15, 5583-5592.

Chen, G., Gulbranson, D. R., Hou, Z., Bolin, J. M., Ruotti, V., Probasco, M. D., Smuga-Otto, K., Howden, S. E., Diol, N. R., Propson, N. E., et al. (2011). Chemically defined conditions for human iPSC derivation and culture. Nat Methods 8, 424-429.

Cheng, H., Kari, G., Dicker, A. P., Rodeck, U., Koch, W. J., and Force, T. (2011). A novel preclinical strategy for identifying cardiotoxic kinase inhibitors and mechanisms of cardiotoxicity. Circ Res 109, 1401-1409.

Chou, B. K., Gu, H., Gao, Y., Dowey, S. N., Wang, Y., Shi, J., Li, Y., Ye, Z., Cheng, T., and Cheng, L. (2015). A facile method to establish human induced pluripotent stem cells from adult blood cells under feeder-free and xeno-free culture conditions: a clinically compliant approach. Stem Cells Transl Med 4, 320-332.

Chu, V. T., Weber, T., Wefers, B., Wurst, W., Sander, S., Rajewsky, K., and Kuhn, R. (2015). Increasing the efficiency of homology-directed repair for CRISPR-Cas9-induced precise gene editing in mammalian cells. Nat Biotechnol 33, 543-548.

Delacroix, L., Moutier, E., Altobelli, G., Legras, S., Poch, O., Choukrallah, M. A., Bertin, I., Jost, B., and Davidson, I. (2010). Cell-specific interaction of retinoic acid receptors with target genes in mouse embryonic fibroblasts and embryonic stem cells. Mol Cell Biol 30, 231-244.

Doench, J. G., Fusi, N., Sullender, M., Hegde, M., Vaimberg, E. W., Donovan, K. F., Smith, I., Tothova, Z., Wilen, C., Orchard, R., et al. (2016). Optimized sgRNA design to maximize activity and minimize off-target effects of CRISPR-Cas9. Nat Biotechnol 34, 184-191.

Fajardo, G., Zhao, M., Berry, G., Wong, L. J., Mochly-Rosen, D., and Bernstein, D. (2011). Beta2-adrenergic receptors mediate cardioprotection through crosstalk with mitochondrial cell death pathways. J Mol Cell Cardiol 51, 781-789.

Fryer, R. M., Pratt, P. F., Hsu, A. K., and Gross, G. J. (2001). Differential activation of extracellular signal regulated kinase isoforms in preconditioning and opioid-induced cardioprotection. J Pharmacol Exp Ther 296, 642-649.

Fusaki, N., Ban, H., Nishiyama, A., Saeki, K., and Hasegawa, M. (2009). Efficient induction of transgene-free human pluripotent stem cells using a vector based on Sendai virus, an RNA virus that does not integrate into the host genome. Proc Jpn Acad Ser B Phys Biol Sci 85, 348-362.

Granger, C. B. (2006). Prediction and prevention of chemotherapy-induced cardiomyopathy: can it be done? Circulation 114, 2432-2433.

Hasan, S., Dinh, K., Lombardo, F., and Kark, J. (2004). Doxorubicin cardiotoxicity in African Americans. J Natl Med Assoc 96, 196-199.

Hudson, M. M., Ness, K. K., Gurney, J. G., Mulrooney, D. A., Chemaitilly, W., Krull, K. R., Green, D. M., Armstrong, G. T., Nottage, K. A., Jones, K. E., et al. (2013). Clinical ascertainment of health outcomes among adults treated for childhood cancer. JAMA 309, 2371-2381.

Ichikawa, Y., Ghanefar, M., Bayeva, M., Wu, R I, Khechaduri, A., Naga Prasad, S. V., Mutharasan, R. K., Naik, T. J., and Ardehali, H. (2014). Cardiotoxicity of doxorubicin is mediated through mitochondrial iron accumulation. J Clin Invest 124, 617-630.

Ichiki, T. (2006). Role of cAMP response element binding protein in cardiovascular remodeling: good, bad, or both? Arterioscler Thromb Vasc Biol 26, 449-455.

Iulianella, A., and Lohnes, D. (2002). Chimeric analysis of retinoic acid receptor function during cardiac looping. Dev Biol 247, 62-75.

Izumi, M., Masaki, M., Hiramoto, Y., Sugiyama, S., Kuroda, T., Terai, K., Hori, M., Kawase, I., and Hirota, H. (2006). Cross-talk between bone morphogenetic protein 2 and leukemia inhibitory factor through ERK 1/2 and Smad1 in protection against doxorubicin-induced injury of cardiomyocytes. J Mol Cell Cardiol 40, 224-233.

Krischer, J. P., Epstein, S., Cuthbertson, D. D., Goorin, A. M., Epstein, M. L., and Lipshultz, S. E. (1997). Clinical cardiotoxicity following anthracycline treatment for childhood cancer: the Pediatric Oncology Group experience. J Clin Oncol 15, 1544-1552.

Lalevee, S., Anno, Y. N., Chatagnon, A., Samarut, E., Poch, O., Laudet, V., Benoit, G., Lecompte, O., and Rochette-Egly, C. (2011). Genome-wide in silico identification of new conserved and functional retinoic acid receptor response elements (direct repeats separated by 5 bp). J Biol Chem 286, 33322-33334.

Lefrak, E. A., Pitha, J., Rosenheim, S., and Gottlieb, J. A. (1973). A clinicopathologic analysis of driamycin cardiotoxicity. Cancer 32, 302-314.

Lek, M., Karczewski, K. J., Minikel, E. V., Samocha, K. E., Banks, E., Fennell, T., O'Donnell-Luria, A. H., Ware, J. S., Hill, A. J., Cummings, B. B., et al. (2016). Analysis of protein-coding genetic variation in 60,706 humans. Nature 536, 285-291.

Liao, Y., Smyth, G. K., and Shi, W. (2013). The Subread aligner: fast, accurate and scalable read mapping by seed-and-vote. Nucleic Acids Res 41, e108.

Lim, C. C., Zuppinger, C., Guo, X., Kuster, G. M., Helmes, M., Eppenberger, H. M., Suter, T. M., Liao, R., and Sawyer, D. B. (2004). Anthracyclines induce calpain-dependent titin proteolysis and necrosis in cardiomyocytes. J Biol Chem 279, 8290-8299.

Love, M. I., Huber, W., and Anders, S. (2014). Moderated estimation of fold change and dispersion for RNA-seq data with DESeq2. Genome Biol 15, 550.

Magdy, T., Burmeister, B. T., and Burridge, P. W. (2016). Validating the pharmacogenomics of chemotherapy-induced cardiotoxicity: What is missing? Pharmacol Ther 168, 113-125.

Minotti, G., Menna, P., Salvatorelli, E., Cairo, G., and Gianni, L. (2004). Anthracyclines: molecular advances and pharmacologic developments in antitumor activity and cardiotoxicity. Pharmacol Rev 56, 185-229.

Mulrooney, D. A., Yeazel, M. W., Kawashima, T., Mertens, A. C., Mitby, P., Stovall, M., Donaldson, S. S., Green, D. M., Sklar, C. A., Robison, L. L., et al. (2009). Cardiac outcomes in a cohort of adult survivors of childhood and adolescent cancer: retrospective analysis of the Childhood Cancer Survivor Study cohort. BMJ 339, b4606.

Musunuru, K., Bernstein, D., Cole, F. S., Khokha, M. K., Lee, F. S., Lin, S., McDonald, T. V., Moskowitz, I. P., Quertermous, T., Sankaran, V. G., et al. (2018). Functional Assays to Screen and Dissect Genomic Hits: Doubling Down on the National Investment in Genomic Research. Circ Genom Precis Med 11, e002178.

Oceguera-Yanez, F., Kim, S. I., Matsumoto, T., Tan, G. W., Xiang, L., Hatani, T., Kondo, T., Ikeya, M., Yoshida, Y., Inoue, H., et al. (2016). Engineering the AAVS1 locus for consistent and scalable transgene expression in human iPSCs and their differentiated derivatives. Methods 101, 43-55.

Ochoa, W. F., Corbalan-Garcia, S., Eritja, R., Rodriguez-Alfaro, J. A., Gomez-Femandez, J. C., Fita, I., and Verdaguer, N. (2002). Additional binding sites for anionic phospholipids and calcium ions in the crystal structures of complexes of the C2 domain of protein kinase calpha. J Mol Biol 320, 277-291.

Oeffinger, K. C., Mertens, A. C., Sklar, C. A., Kawashima, T., Hudson, M. M., Meadows, A. T., Friedman, D. L., Marina, N., Hobbie, W., Kadan-Lottick, N. S., et al.

(2006). Chronic health conditions in adult survivors of childhood cancer. N Engl J Med 355, 1572-1582.

Peterson, S. E., and Loring, J. F. (2014). Genomic instability in pluripotent stem cells: implications for clinical applications. J Biol Chem 289, 4578-4584.

Ran, F. A., Hsu, P. D., Wright, J., Agarwala, V., Scott, D. A., and Zhang, F. (2013). Genome engineering using the CRISPR-Cas9 system. Nat Protoc 8, 2281-2308.

Schmittgen, T. D., and Livak, K. J. (2008). Analyzing real-time PCR data by the comparative C(T) method. Nat Protoc 3, 1101-1108.

Simoncikova, P., Ravingerova, T., and Barancik, M. (2008). The effect of chronic doxorubicin treatment on mitogen-activated protein kinases and heat stress proteins in rat hearts. Physiol Res 57 Suppl 2, S97-S 102.

Singal, P. K., and Iliskovic, N. (1998). Doxorubicin-induced cardiomyopathy. N Engl J Med 339, 900-905.

Su, H. F., Samnsamshariat, A., Fu, J., Shan, Y. X., Chen, Y. H., Piomelli, D., and Wang, P. H. (2006). Oleylethanolamide activates Ras-Erk pathway and improves myocardial function in doxorubicin-induced heart failure. Endocrinology 147, 827-834.

Swain, S. M., Whaley, F. S., and Ewer, M. S. (2003). Congestive heart failure in patients treated with doxorubicin: a retrospective analysis of three trials. Cancer 97, 2869-2879.

van Dalen, E. C., Raphael, M. F., Caron, H. N., and Kremer, L. C. (2014). Treatment including anthracyclines versus treatment not including anthracyclines for childhood cancer. Cochrane Database Syst Rev, CD006647.

van der Pal, H. J., van Dalen, E. C., van Delden, E., van Dijk, I. W., Kok, W. E., Geskus, R. B., Sieswerda, E., Oldenburger, F., Koning, C. C., van Leeuwen, F. E., et al. (2012). High risk of symptomatic cardiac events in childhood cancer survivors. J Clin Oncol 30, 1429-1437.

Volonte, D., McTieman, C. F., Drab, M., Kasper, M., and Galbiati, F. (2008). Caveolin-1 and caveolin-3 form heterooligomeric complexes in atrial cardiac myocytes that are required for doxorubicin-induced apoptosis. Am J Physiol Heart Circ Physiol 294, H392-401.

Von Hoff, D. D., Layard, M. W., Basa, P., Davis, H. L., Jr., Von Hoff, A. L., Rozencweig, M., and Muggia, F. M. (1979). Risk factors for doxorubicin-induced congestive heart failure. Ann Intern Med 91, 710-717.

Wojnowski, L., Kulle, B., Schirmer, M., Schluter, G., Schmidt, A., Rosenberger, A., Vonhof, S., Bickeboller, H., Toliat, M. R., Suk, E. K., et al. (2005). NAD(P)H oxidase and multidrug resistance protein genetic polymorphisms are associated with doxorubicin-induced cardiotoxicity. Circulation 112, 3754-3762.

Xiang, P., Deng, H. Y., Li, K., Huang, G. Y., Chen, Y., Tu, L., Ng, P. C., Pong, N. H., Zhao, H., Zhang, L., et al. (2009). Dexrazoxane protects against doxorubicin-induced cardiomyopathy: upregulation of Akt and Erk phosphorylation in a rat model. Cancer Chemother Pharmacol 63, 343-349.

Yang, F., Teves, S. S., Kemp, C. J., and Henikoff, S. (2014). Doxorubicin, DNA torsion, and chromatin dynamics. Biochim Biophys Acta 1845, 84-89.

Yang, L., Luo, C., Chen, C., Wang, X., Shi, W., and Liu, J. (2016). All-trans retinoic acid protects against doxorubicin-induced cardiotoxicity by activating the ERK2 signalling pathway. Br J Pharmacol 173, 357-371.

Zhang, S., Liu, X., Bawa-Khalfe, T., Lu, L. S., Lyu, Y. L., Liu, L. F., and Yeh, E. T. (2012). Identification of the molecular basis of doxorubicin-induced cardiotoxicity. Nat Med 18, 1639-1642.

REFERENCE TO A SEQUENCE LISTING SUBMITTED VIA EFS-WEB

The content of the ASCII text file of the sequence listing named "702581_00303_ST25.txt" which is 5.09 kb in size was created on Aug. 13, 2019 and electronically submitted via EFS-Web herewith the application is incorporated herein by reference in its entirety.

I claim:

1. A method for treating cardiotoxicity in a subject having a cell proliferative disease or disorder and undergoing treatment with an anthracycline chemotherapeutic agent, wherein the subject has cardiotoxicity or is at risk for developing cardiotoxicity induced by treatment with the anthracycline chemotherapeutic agent, the method comprising administering to the subject a specific agonist of the retinoic acid receptor gamma (RARG).

2. The method of claim 1, wherein the cell proliferative disease or disorder is selected from the group consisting of bladder cancer, breast cancer, glioblastoma, lymphoma, leukemia, lung cancer, ovarian cancer, pancreatic cancer, soft tissue sarcoma, and thyroid cancer.

3. The method of claim 1, wherein the anthracycline chemotherapeutic agent intercalates within DNA and prevents the release of topoisomerase 2β (TOP2B) from DNA bound to the TOP2B.

4. The method of claim 1, wherein the anthracycline chemotherapeutic agent is selected from the group consisting of doxorubicin, daunorubicin, epirubicin, idarubicin, and aldoxorubicin.

5. The method of claim 1, wherein the anthracycline chemotherapeutic agent is doxorubicin and in the treatment method the subject is administered a maximum cumulative dose of doxorubicin that is greater than about 400 mg/m$^2$.

6. The method of claim 1, wherein the anthracycline chemotherapeutic agent is daunorubicin and in the treatment method the subject is administered a maximum cumulative dose of daunorubicin that is greater than about 500 mg/m$^2$.

7. The method of claim 1, wherein the anthracycline chemotherapeutic agent is epirubicin and in the treatment method the subject is administered a maximum cumulative dose of epirubicin that is greater than about 800 mg/m$^2$.

8. The method of claim 1, wherein the anthracycline chemotherapeutic agent is idarubicin and in the treatment method the subject is administered intravenously a maximum cumulative dose of idarubicin that is greater than about 100 mg/m$^2$.

9. The method of claim 1, wherein the anthracycline chemotherapeutic agent is idarubicin and in the treatment method the subject is administered orally a maximum cumulative dose of idarubicin that is greater than about 300 mg/m$^2$.

10. The method of claim 1, wherein the RARG agonist represses expression of TOP2B.

11. The method of claim 1, wherein the RARG agonist is selected from the group consisting of palovaroten (4-[(E)-2-[5,5,8,8-tetramethyl-3-(1H-pyrazol-1-ylmethyl)-5,6,7,8-tetrahydronaphthalen-2-yl]ethenyl]benzoic acid), BMS 961 (3-Fluoro-4-[[2-hydroxy-2(5,5,8,8-tetramethyl-5,6,7,8,-tetrahydro-2-naphthalenyl)acetyl]amino]-benzoic acid); CD1530 (4-(6-Hydroxy-7-tricyclo[3.3.1.13,7]dec-1-yl-2-naphthalenyl)benzoic acid); and CD437 (6-(4-Hydroxy-3-tricyclo[3.3.1.13,7]dec-1-ylphenyl)-2-naphthalenecarboxylic acid).

12. The method of claim 1 comprising administering the RARG agonist prior to administering the anthracycline chemotherapeutic agent.

13. The method of claim 1 comprising administering the RARG agonist concurrently with administering the anthracycline chemotherapeutic agent.

14. The method of claim 1 comprising administering the RARG agonist after administering the anthracycline chemotherapeutic agent.

15. The method of claim 1, wherein the subject is no more than 5 years of age.

16. The method of claim 1, wherein the subject has breast cancer.

17. The method of claim 1, wherein the subject is undergoing treatment with doxorubicin.

18. The method of claim 1, wherein the agonist of the retinoic acid receptor gamma (RARG) is CD1530 (4-(6-Hydroxy-7-tricyclo[3.3.1.13,7]dec-1-yl-2-naphthalenyl) benzoic acid).

19. A method for treating cardiotoxicity in a subject having a cell proliferative disease or disorder and undergoing treatment with an anthracycline chemotherapeutic agent, wherein the subject has cardiotoxicity or is at risk for developing cardiotoxicity induced by treatment with the anthracycline chemotherapeutic agent, the method comprising administering to the subject a specific agonist of the retinoic acid receptor gamma (RARG) wherein the specific agonist of the RARG is not an agonist for retinoic acid receptor alpha (RARA).

20. A method for treating cardiotoxicity in a subject having a cell proliferative disease or disorder and undergoing treatment with an anthracycline chemotherapeutic agent, wherein the subject has cardiotoxicity induced by treatment with the anthracycline chemotherapeutic agent, the method comprising administering to the subject a specific agonist of the retinoic acid receptor gamma (RARG).

* * * * *

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
gacttttgga ggcccagtgg                                                 20

<210> SEQ ID NO 2
<211> LENGTH: 19
<212> TYPE: DNA
<213> ORGANISM: Artificial Sequence
<220> FEATURE:
<223> OTHER INFORMATION: synthetic primer

<400> SEQUENCE: 2
gaggccatct ccttgggga                                                  19

<210> SEQ ID NO 3
<211> LENGTH: 20
<212> TYPE: DNA
<213> ORGANISM: Artificial Sequence
```

```
<220> FEATURE:
<223> OTHER INFORMATION: synthetic primer

<400> SEQUENCE: 3
tgccgaagca cccagataag                                                    20

<210> SEQ ID NO 4
<211> LENGTH: 20
<212> TYPE: DNA
<213> ORGANISM: Artificial Sequence
<220> FEATURE:
<223> OTHER INFORMATION: synthetic primer

<400> SEQUENCE: 4
tacctacatt gcaggctggc                                                    20

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
ggcgccggca ggaaggaaat                                                    20

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
agccagggca ttggccacac                                                    20

<210> SEQ ID NO 7
<211> LENGTH: 18
<212> TYPE: DNA
<213> ORGANISM: Artificial Sequence
<220> FEATURE:
<223> OTHER INFORMATION: synthetic

<400> SEQUENCE: 7
ctaggagtgc ggcgagtg                                                      18

<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
ccacttacca cccaggtcag                                                    20

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9
catgtgcctc tgtcctcctg                                                    20
```

```
<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
ctgggagatg gtcagtctgc                                              20

<210> SEQ ID NO 11
<211> LENGTH: 10
<212> TYPE: DNA
<213> ORGANISM: Artificial Sequence
<220> FEATURE:
<223> OTHER INFORMATION: synthetic

<400> SEQUENCE: 11
cctcgcagcc                                                         10

<210> SEQ ID NO 12
<211> LENGTH: 10
<212> TYPE: DNA
<213> ORGANISM: Artificial Sequence
<220> FEATURE:
<223> OTHER INFORMATION: synthetic

<400> SEQUENCE: 12
ccttgcagcc                                                         10

<210> SEQ ID NO 13
<211> LENGTH: 20
<212> TYPE: DNA
<213> ORGANISM: Artificial Sequence
<220> FEATURE:
<223> OTHER INFORMATION: synthetic gRNA1

<400> SEQUENCE: 13
tattcctcgc tgagaaacgc                                              20

<210> SEQ ID NO 14
<211> LENGTH: 20
<212> TYPE: DNA
<213> ORGANISM: Artificial Sequence
<220> FEATURE:
<223> OTHER INFORMATION: synthetic gRNA2

<400> SEQUENCE: 14
ggtcgcgatg tacgactgta                                              20

<210> SEQ ID NO 15
<211> LENGTH: 29
<212> TYPE: DNA
<213> ORGANISM: Homo sapiens

<400> SEQUENCE: 15
ccgggtcgcg atgtacgact gtatggaaa                                    29

<210> SEQ ID NO 16
<211> LENGTH: 29
<212> TYPE: DNA
<213> ORGANISM: Homo sapiens

<400> SEQUENCE: 16
tttccataca gtcgtacatc gcgacccgg                                    29
```

```
<210> SEQ ID NO 17
<211> LENGTH: 36
<212> TYPE: DNA
<213> ORGANISM: Homo sapiens

<400> SEQUENCE: 17
gccatggcca ccaataagga gcgactcttt gcggct                        36

<210> SEQ ID NO 18
<211> LENGTH: 36
<212> TYPE: DNA
<213> ORGANISM: Homo sapiens

<400> SEQUENCE: 18
agccgcaaag agtcgctcct tattggtggc catggc                        36

<210> SEQ ID NO 19
<211> LENGTH: 20
<212> TYPE: DNA
<213> ORGANISM: Artificial Sequence
<220> FEATURE:
<223> OTHER INFORMATION: synthetic gRNA

<400> SEQUENCE: 19
ggggccacta gggacaggat                                          20

<210> SEQ ID NO 20
<211> LENGTH: 29
<212> TYPE: DNA
<213> ORGANISM: Homo sapiens

<400> SEQUENCE: 20
agtggggcca ctagggacag gattggtga                                29

<210> SEQ ID NO 21
<211> LENGTH: 29
<212> TYPE: DNA
<213> ORGANISM: Homo sapiens

<400> SEQUENCE: 21
tcaccaatcc tgtccctagt ggccccact                                29

<210> SEQ ID NO 22
<211> LENGTH: 20
<212> TYPE: DNA
<213> ORGANISM: Artificial Sequence
<220> FEATURE:
<223> OTHER INFORMATION: synthetic gRNA

<400> SEQUENCE: 22
aagtcgggtg gctgcggcgc                                          20

<210> SEQ ID NO 23
<211> LENGTH: 35
<212> TYPE: DNA
<213> ORGANISM: Homo sapiens

<400> SEQUENCE: 23
gccatggcca agtcgggtgg ctgcggcgcg ggagc                         35

<210> SEQ ID NO 24
<211> LENGTH: 35
<212> TYPE: DNA
```

```
<213> ORGANISM: Homo sapiens

<400> SEQUENCE: 24
gctcccgcgc cgcagccacc cgacttggcc atggc                              35

<210> SEQ ID NO 25
<211> LENGTH: 20
<212> TYPE: DNA
<213> ORGANISM: Artificial Sequence
<220> FEATURE:
<223> OTHER INFORMATION: synthetic gRNA

<400> SEQUENCE: 25
ccaccccaat gcctctagcg                                               20

<210> SEQ ID NO 26
<211> LENGTH: 43
<212> TYPE: DNA
<213> ORGANISM: Homo sapiens

<400> SEQUENCE: 26
tccttgcagc ctggtcccca ccccaatgcc tctagcgagg atg                     43

<210> SEQ ID NO 27
<211> LENGTH: 43
<212> TYPE: DNA
<213> ORGANISM: Homo sapiens

<400> SEQUENCE: 27
catcctcgct agaggcattg gggtggggac caggctgcaa gga                     43

<210> SEQ ID NO 28
<211> LENGTH: 43
<212> TYPE: DNA
<213> ORGANISM: Artificial Sequence
<220> FEATURE:
<223> OTHER INFORMATION: synthetic repair oligo based on Homo sapiens
      seqeunce

<400> SEQUENCE: 28
tcctcgcagc ctggtcccca ccccaatgcc tctagcgaag atg                     43
```